United States Patent [19]
Seed et al.

[11] Patent Number: 5,849,898
[45] Date of Patent: Dec. 15, 1998

[54] CD40 CODING SEQUENCES

[75] Inventors: Brian Seed, Boston, Mass.; Janet Allen, Glasgow, Scotland; Alejandro Aruffo, Edmonds, Wash.; David Camerini, Charlottesville, Va.; Leander Lauffer; Carmen Oquendo, both of Gladenbach, Germany; David Simmons, Headington, United Kingdom; Ivan Stamenkovic, Winchester, Mass.; Siegfried Stengelin, Eppstein, Germany; Martine Amiot, Nantes, France

[73] Assignee: The General Hospital Corporation, Charlestown, Mass.

[21] Appl. No.: 485,447

[22] Filed: Jun. 7, 1995

Related U.S. Application Data

[60] Division of Ser. No. 983,647, Dec. 1, 1992, which is a continuation-in-part of Ser. No. 553,759, Jul. 13, 1990, abandoned, which is a continuation-in-part of Ser. No. 498,809, Mar. 23, 1990, abandoned, which is a continuation-in-part of Ser. No. 379,076, Jul. 13, 1989, abandoned, which is a continuation-in-part of Ser. No. 160,416, Feb. 25, 1988, abandoned.

[51] Int. Cl.$^6$ .................................................. C12N 15/12
[52] U.S. Cl. ................ 536/23.5; 435/69.1; 435/257.3; 435/320.1
[58] Field of Search .................... 536/23.5; 435/69.1, 435/252.3, 320.1

[56] References Cited

U.S. PATENT DOCUMENTS 4,675,285   6/1987   Clark et al. ................................. 435/6

FOREIGN PATENT DOCUMENTS 0 289 949   of 1988   European Pat. Off. .
2191494   12/1987   United Kingdom .
WO 88/00209   1/1988   WIPO .

OTHER PUBLICATIONS

Pezzutto et al. (1987) *The Journal of Immunology* 138:2793–2799.
Teddar et al. (1988) *Immunology* 85:208–212.
Stamenkovic et al. (1988) *J. Exp. Med.* 168:1205–1210.
Stamenkovic et al. (1989) *Cell* 56:1057–1062.
Stamenkovic et al. (1989) *EMBO J.* 8:1403–1410.
Shaw et al. (1986) *Nature* 323:262–264.
Yang et al. (1986) *Cell* 47:3–10.
Huynh et al. (1986) in *DNA Cloning vol. 1, A Practical Approach*, Glover, D.M. (ed.) IRL Press, Oxford, UK, pp. 49–78.
Rieber et al. (1986) in *Leukocyte Typing II*, vol. 1, pp. 233–242.
Kawata et al. (1984) *J. Exp. Med.* 160:633–651.
Seed et al. (1987) *Proc. Natl. Acad. Sci. USA* 84:3365–3369.
Palker et al. (1985) in *Leukocyte Typing II*, Springer–Verlag, New York, pp. 303–313.
Lazarovits et al. (1987) in *Leukocyte Typing III*, McMichael (ed.) Oxford University Press, Oxford, UK, pp. 219–223.
Sandrin et al. (1987) in *Leukocyte Typing III*, McMichael (ed.) Oxford University Press, Oxford, UK, pp. 216–219.
Valentine et al. (1987) in *Leukocyte Typing III*, McMichael (ed.) Oxford University Press, Oxford, UK, pp. 440–443.
Rothlein et al. (1987) *Exp. Med.* 163:1132–1149.
Hynes, R.O. (2987) *Cell* 48:549–554.
Williams, A.F. (1987) *Immunol. Today* 8:293–303.

(List continued on next page.)

*Primary Examiner*—John Ulm
*Attorney, Agent, or Firm*—Greenlee, Winner and Sullivan, PC

[57] ABSTRACT

A simple and highly efficient method for cloning cDNAs from mammalian expression libraries based on transient expression in mammalian host cells has been discovered. The present invention specifically provides the CD40 cDNA sequence.

2 Claims, 32 Drawing Sheets

```
  1  GCCTCGCTCG GGCGCCCAGT GGTCCTGCCG CCTGGTCTCA CCTCGCCATG
 51  GTTCGTCTGC CTCTGCAGTG CGTCCTCTGG GGCTGCTTGC TGACCGCTGT
101  CCATCCAGAA CCACCCACTG CATGCAGAGA AAAACAGTAC CTAATAAACA
151  GTCAGTGCTG TTCTTTGTGC CAGCCAGGAC AGAAACTGGT GAGTGACTGC
201  ACAGAGTTCA CTGAAACGGA ATGCCTTCCT TGCGGTGAAA GCGAATTCCT
251  AGACACCTGG AACAGAGAGA CACACTGCCA CCAGCACAAA TACTGCGACC
301  CCAACCTAGG GCTTCGGGTC CAGCAGAAGG GCACCTCAGA AACAGACACC
351  ATCTGCACCT GTGAAGAAGG CTGGCACTGT ACGAGTGAGG CCTGTGAGAG
401  CTGTGTCCTG CACCGCTCAT GCTCGCCCGG CTTTGGGGTC AAGCAGATTG
451  CTACAGGGGT TTCTGATACC ATCTGCGAGC CCTGCCCAGT CGGCTTCTTC
501  TCCAATGTGT CATCTGCTTT CGAAAAATGT CACCCTTGGA CAAGCTGTGA
551  GACCAAAGAC CTGGTTGTGC AACAGGCAGGC ACAAACAAGA CTGATGTTGT
601  CTGTGGTCCC CAGGATCGGC TGAGAGCCCT GGTGGTGATC CCCATCATCT
651  TCGGGATCCT GTTTGCCATC CTCTTGGTGC TGGTCTTTAT CAAAAAGGTG
701  GCCAAGAAGC CAACCAATAA GGCCCCCCAC CCCAAGCAGG AACCCCAGGA
751  GATCAATTTT CCCGACGATC TTCCTGGCTC CAACACTGCT GCTCCAGTGC
801  AGGAGACTTT ACATGGATGC CAACCGGTCA CCCAGGAGGA TGGCAAAGAG
851  AGTCGCATCT CAGTGCAGGA GAGACAGTGA GGCTGCACCC ACCCAGGAGT
901  GTGGCCACGT GGGCAAACAG GCAGTTGGCC AGAGAGCCTG GTGCTGCTGC
951  TGCAGGGGTG CAGGCAGAAG CGGGGAGCTA TGCCCAGTCA GTGCCAGCCC
     CTC
```

OTHER PUBLICATIONS

Aruffo, A. and Seed, B. (1987) *Proc. Natl. Acad. Sci. USA* 84:8573–8577.
McMichael et al. (1987) *Leukocyte Typing III, White Cell Differentiation Antigen,* McMichael (ed.) Oxford University Press, Oxford, UK, pp. 31–62.
Aruffo, A. and Seed, B. (1987) *EMBO J.* 6:3313–3316.
Seed, B. (1987) *Nature* 329:840–842.
Simmmons et al. (1988) *Nature* 331:624–627.
Sleckman et al. (1987) *Nature* 328:351–353.
Simmons, D. and Seed, B. (1988) *Nature* 333:568–570.
Stuve et al. (1987) *J. Virol.* 61:327–335.
Oshima et al. (1987) *Proc. Natl. Acad. Sci. USA* 84:685–689.
Gerald et al. (1986) *J. Gen. Virol.* 67:2695–2703.
Bernstein et al. (1982) *J. immunol.* 128:876–881.
Tandon et al. (1989) *J. Biol. Chem.* 264:7570–7575.
Ockenhouse et al. (1989) *Science* 243:1469–1471.
Allen, J.M. and Seed, B. (1989) *Science* 243:378–381.
Stengelin et al. (1988) *EMBO J.* 7:1053–1059.
Andrews et al. (1984) in *Leukocyte Typing,* pp. 398–404.
Johnson et al. (1986) *Cell* 545–554.
Seigelman et al. (1989) *Science* 243:1165–1172.
Lasky et al. (1989) *Cell* 56:1045–1055.
Hotta et al. (1988) *Cancer Res.* 48:2955–2962.
Siegelman, M. and Weissman, I. (1989) *Proc. Natl. Acad. Sci. USA* 86:5562–5566.
Tedder et al. (1989) *J. Cell Biol.* 170:123–133.
Bowen et al. (1989) *J. Cell Biol.* 109:421–427.
Allen, J.M. and Seed, B. (1988) *Nucl. Acids Res.* 16:11824.
Pohl, T. (1990) *Meth. Enzymol.* 182:68–83.
Stryer, L. (1988) *Biochemistry* (3rd Ed.) p. 24.
Johnson et al. (1985) *Hybridoma Technology in the Biosciencs & Medicine* (T.A. Springer, ed.) Plenum, NY, 163–175.
Stuart et al. (1987) *J. Exp. Med.* 166(6):1668–1684.
Dang, L. and Rock, K. (1991) *J. Immunol.* 146:3273–3279.
Ross, L. et al. (1992) *J. Biol. Chem.* 267:8537–8543.
Hibbs, M. et al. (1991) *Science* 251:1611–1613.
Berendt, A. et al. (1992) *Cell* 68:71–81.
Ockenhouse, C. et al. (1992) *Cell* 68:63–69.
Diamond, M. et al. (1991) *Cell* 65:961–971.
Cabanas, C. and Hogg, N. (1991) *FEBS Lett.* 292:284–288.
Staunton, D. et al. (1990) *Cell* 61:243–254 (errata at Cell (1990) 61:1157 and Cell (1991) 67:1312).
Piela–Smith, T. et al. (1992) *J. Immunol.* 148:1375–1381.
Greve, J. et al. (1989) *Cell* 56:839–847.
Staunton, D. et al. (1992) *J. Immunol.* 148:3271–3274.
Register, R. et al. (1991) *J. Virol.* 65:6589–6596.
Greve, J. et al. (1991) *J. Virol.* 65:6015–6023.
Lineberger, D. et al. (1992) *Virus Res.* 24:173–186.
Oppenheimer–Marks, N. et al. (1991) *J. Immunol.* 147:2913–2921.
Perry, M. et al. (1992) *Cell Tissue Res.* 268:317–326.
Dustin, M. et al. (1992) *J. Immunol.* 148:2654–2663.
Webb, D. et al. (1991) *J. Immunol.* 146:3682–3686.
Ockenhouse, C. et al. (1991) *J. Infect. Dis.* 164:163–169.
Gruber, M. et al. (1991) *AIDS Res. Hum. Retroviruses* 7:45–53.
Dohlsten, M. et al. (1991) *Eur. J. Immunol.* 21:131–135.
Staunton, D. et al. (1989) *Cell* 56:849–853.
Moretta, A. et al. (1987) *Proc. Natl. Acad. Sci. USA* 84:1654–1658.
Canonica, G.W. et al. (1988) *Mech. Ageing Dev.* 42:27–35.
Damle, N.K. et al. (1988) *J. Immunol.* 140:1753–1761.
Ledbetter, J.A. et al. (1986) *J. Immunol.* 137:3299–3305.
Ledbetter, J.A. et al. (1985) *J. Immunol.* 135:2331–2336.
Poggi, A. et al. (1987) *Eur. J. Immunol.* 17:1065–1068.
Martin et al. (1986) *J. Immunol.* 136:3282–3287.
Tomassini et al. (1986) *J. Virol.* 58:290–295.
Smith et al. (1987) *Science* 238:1704–1706.
Treiger et al. (1986) *J. Immunol.* 136:4094–4105.
Hunkapiller et al. (1983) *Meth. Enzymol.* 91:227–236.
Dustin et al. (1986) *J. Immunol.* 137:245–254.
Rothlein et al. (1986) *J. Immunol.* 137:1270–1274.
Marlin et al. (1985) *Cell* 51:813–819.
Jacobs et al. (1985) *Nature* 313:806–810.
Hedman, H. and Ludman, E. (1991) *J. Immunol.* 149:2295–2299.
Moretta, A. et al. (1985) *J. Exp. Med.* 162:823–838.
June, C.H. et al. (1987) *Mol. Cell. Biol.* 7:4472–4481.
Kozbor, D. et al. (1987) *J. Immunol.* 138:4128–4132.
Pantaleo, G. et al. (1986) *Eur. J. Immunol.* 16:1639–1642.
Weiss, A. et al. (1986) *J. immunol.* 137:819–825.

```
   1 GGCGTAATCT GCTGCTTGCA AACAAAAAAA CCACCGCTAC CAGCGGTGGT
  51 TTGTTTGCCG GATCAAGAGC TACCAACTCT TTTTCCGAAG GAACTGGCTT
 101 CAGCAGAGCG CAGATACCAA ATACTGTCCT TCTAGTGTAG CCGTAGTTAG
 151 GCCACCACTT CAAGAACTCT GTAGCACCGC CTACATACCT CGCTCTGCTA
 201 ATCCTGTTAC CAGTGGCTGC TGCCAGTGGC GATAAGTCGT GTCTTACCGG
 251 GTTGGACTCA AGACGATAGT TACCGGATAA GGCGCAGCGG TCGGGCTGAA
 301 CGGGGGGTTC GTGCACACAG CCCAGCTTGG AGCGAACGAC CTACACCGAA
 351 CTGAGATACC TACAGCGTGA GCTATGAGAA AGCGCCACGC TTCCCGAAGG
 401 GAGAAAGGCG GACAGGTATC CGGTAAGCGG CAGGGTCGGA ACAGGAGAGC
 451 GCACGAGGGA GCTTCCAGGG GGAAACGCCT GGTATCTTTA TAGTCCTGTC
 501 GGGTTTCGCC ACCTCTGACT TGAGCGTCGA TTTTTGTGAT GCTCGTCAGG
 551 GGGGCGGAGC CTATGGAAAA ACGCCAGCAA CGCCGAATTA CCGCGGTCTT
 601 TCTCAACGTA ACACTTTACA GCGGCGCGTC ATTTGATATG ATGCGCCCCG
 651 CTTCCCGATA AGGGAGCAGG CCAGTAAAAG CATTACCCGT GGTGGGGTTC
 701 CCGAGCGGCC AAAGGGAGCA GACTCTAAAT CTGCCGTCAT CGACTTCGAA
 751 GGTTCGAATC CTTCCCCCAC CACCATCACT TTCAAAAGTC CGAAAGAATC
 801 TGCTCCCTGC TTGTGTGTTG GAGGTCGCTG AGTAGTGCGC GAGTAAAATT
 851 TAAGCTACAA CAAGGCAAGG CTTGACCGAC AATTGCATGA AGAATCTGCT
 901 TAGGGTTAGG CGTTTTGCGC TGCTTCGCGA TGTACGGGCC AGATATACGC
 951 GTTGACATTG ATTATTGACT AGTTATTAAT AGTAATCAAT TACGGGGTCA
1001 TTAGTTCATA GCCCATATAT GGAGTTCCGC GTTACATAAC TTACGGTAAA
1051 TGGCCCGCCT GGCTGACCGC CCAACGACCC CCGCCCATTG ACGTCAATAA
1101 TGACGTATGT TCCCATAGTA ACGCCAATAG GGACTTTCCA TTGACGTCAA
1151 TGGGTGGACT ATTTACGGTA AACTGCCCAC TTGGCAGTAC ATCAAGTGTA
1201 TCATATGCCA AGTACGCCCC CTATTGACGT CAATGACGGT AAATGGCCCG
1251 CCTGGCATTA TGCCCAGTAC ATGACCTTAT GGGACTTTCC TACTTGGCAG
1301 TACATCTACG TATTAGTCAT CGCTATTACC ATGGTGATGC GGTTTTGGCA
1351 GTACATCAAT GGGCGTGGAT AGCGGTTTGA CTCACGGGGA TTTCCAAGTC
1401 TCCACCCCAT TGACGTCAAT GGGAGTTTGT TTTGGCACCA AAATCAACGG
1451 GACTTTCCAA AATGTCGTAA CAACTCCGCC CCATTGACGC AAATGGGCGG
1501 AATTCCTGGG CGGGACTGGG GAGTGGCGAG CCCTCAGATG CTGCATATAA
1551 GCAGCTGCTT TTTGCCTGTA CTGGGTCTCT CTGGTTAGAC CAGATCTGAG
1601 CCTGGGAGCT CTCTGGCTAA CTAGAGAACC CACTGCTTAA GCCTCAATAA
1651 AGCTTCTAGA GATCCCTCGA CCTCGAGGGA TCTTCCATAC CTACCAGTTC
```

FIG. 1A

```
1701  TGCGCCTGCA GGTCGCGGCC GCGACTCTAG AGGATCTTTG TGAAGGAACC
1751  TTACTTCTGT GGTGTGACAT AATTGGACAA ACTACCTACA GAGATTTAAA
1801  GCTCTAAGGT AAATATAAAA TTTTTAAGTG TATAATGTGT TAAACTACTG
1851  ATTCTAATTG TTTGTGTATT TTAGATTCCA ACCTATGGAA CTGATGAATG
1901  GGAGCAGTGG TGGAATGCCT TTAATGAGGA AAACCTGTTT TGCTCAGAAG
1951  AAATGCCATC TAGTGATGAT GAGGCTACTG CTGACTCTCA ACATTCTACT
2001  CCTCCAAAAA AGAAGAGAAA GGTAGAAGAC CCCAAGGACT TTCCTTCAGA
2051  ATTGCTAAGT TTTTTGAGTC ATGCTGTGTT TAGTAATAGA ACTCTTGCTT
2101  GCTTTGCTAT TTACACCACA AAGGAAAAAG CTGCACTGCT ATACAAGAAA
2151  ATTATGGAAA AATATTCTGT AACCTTTATA AGTAGGCATA ACAGTTATAA
2201  TCATAACATA CTGTTTTTTC TTACTCCACA CAGGCATAGA GTGTCTGCTA
2251  TTAATAACTA TGCTCAAAAA TTGTGTACCT TTAGCTTTTT AATTTGTAAA
2301  GGGGTTAATA AGGAATATTT GATGTATAGT GCCTTGACTA GAGATCATAA
2351  TCAGCCATAC CACATTTGTA GAGGTTTTAC TTGCTTTAAA AAACCTCCCA
2401  CACCTCCCCC TGAACCTGAA ACATAAAATG AATGCAATTG TTGTTGTTAA
2451  CTTGTTTATT GCAGCTTATA ATGGTTACAA ATAAAGCAAT AGCATCACAA
2501  ATTTCACAAA TAAAGCATTT TTTTCACTGC ATTCTAGTTG TGGTTTGTCC
2551  AAACTCATCA ATGTATCTTA TCATGTCTGG ATCCTGTGGA ATGTGTGTCA
2601  GTTAGGGTGT GGAAAGTCCC CAGGCTCCCC AGCAGGCAGA AGTATGCAAA
2651  GCATGCATCT CAATTAGTCA GCAACCAGGT GTGGAAAGTC CCCAGGCTCC
2701  CCAGCAGGCA GAAGTATGCA AAGCATGCAT CTCAATTAGT CAGCAACCAT
2751  AGTCCCGCCC CTAACTCCGC CCATCCCGCC CTAACTCCG  CCCAGTTCCG
2801  CCCATTCTCC GCCCCATGGC TGACTAATTT TTTTTATTTA TGCAGAGGCC
2851  GAGGCCGCCT CGGCCTCTGA GCTATTCCAG AAGTAGTGAG GAGGCTTTTT
2901  TGGAGGCCTA GGCTTTTGCA AAAAGCTAAT TC
```

FIG. 1B

```
CCTAAGATGAGCTTTCCATGTAAATTTGTAGCCAGCTTCCTTCTGATTTTCAATGTTTCT         (60)
     MetSerPheProCysLysPheValAlaSerPheLeuLeuIlePheAsnValSer

TCCAAAGGTGCAGTCTCCAAAGAGATTACGAATGCCTTGGAAACCTGGGGTGCCTTGGGT        (120)
SerLysGlyAlaValSerLysGluIleThrAsnAlaLeuGluThrTrpGlyAlaLeuGly
                                                            1
CAGGACATCAACTTGGACATTCCTAGTTTTCAAATGAGTGATGATATTGACGATATAAAA        (180)
GlnAspIleAsnLeuAspIleProSerPheGlnMetSerAspAspIleAspAspIleLys

TGGGAAAAAACTTCAGACAAGAAAAAGATTGCACAATTCAGAAAAGAGAAAGAGACTTTC        (240)
TrpGluLysThrSerAspLysLysLysIleAlaGlnPheArgLysGluLysGluThrPhe

AAGGAAAAAGATACATATAAGCTATTTAAAAAATGGAACTCTGAAAATTAAGCATCTGAAG       (300)
LysGluLysAspThrTyrLysLeuPheLysAsnGlyThrLeuLysIleLysHisLeuLys

ACCGATGATCAGGATATCTACAAGGTATCAATATATGATACAAAAGGAAAAAATGTGTTG       (360)
ThrAspAspGlnAspIleTyrLysValSerIleTyrAspThrLysGlyLysAsnValLeu

GAAAAAATATTTGATTTGAAGATTCAAGAGAGGGTCTCAAAACCAAAGATCTCCTGGACT       (420)
GluLysIlePheAspLeuLysIleGlnGluArgValSerLysProLysIleSerTrpThr

TGTATCAACACAACCCTGACCTGTGAGGTAATGAATGGAACTGACCCCGAATTAAACCTG       (480)
CysIleAsnThrThrLeuThrCysGluValMetAsnGlyThrAspProGluLeuAsnLeu
    ---CHO---                    ---CHO---

TATCAAGATGGGAAACATCTAAAACTTTCTCAGAGGGTCATCACACACAAGTGGACCACC       (540)
TyrGlnAspGlyLysHisLeuLysLeuSerGlnArgValIleThrHisLysTrpThrThr

AGCCTGAGTGCAAAATTCAAGTGCACAGCAGGGAACAAAGTCAGCAAGGAATCCAGTGTC       (600)
SerLeuSerAlaLysPheLysCysThrAlaGlyAsnLysValSerLysGluSerSerVal

GAGCCTGTCAGCTGTCCAGAGAAAGGTCTGGACATCTATCTCATCATTGGCATATGTGGA       (660)
GluProValSerCysProGluLysGlyLeuAspIleTyrLeuIleIleGlyIleCysGly

GGAGGCAGCCTCTTGATGGTCTTTGTGGCACTGCTCGTTTTCTATATCACCAAAAGGAAA       (720)
GlyGlySerLeuLeuMetValPheValAlaLeuLeuValPheTyrIleThrLysArgLys
         ----------TM----------

AAACAGAGGAGTCGGAGAAATGATGAGGAGCTGGAGACAAGAGCCCACAGAGTAGCTACT       (780)
LysGlnArgSerArgArgAsnAspGluGluLeuGluThrArgAlaHisArgValAlaThr

GAAGAAAGGGGCCGGAAGCCCCAACAAATTCCAGCTTCAACCCCTCAGAATCCAGCAACT       (840)
GluGluArgGlyArgLysProGlnGlnIleProAlaSerThrProGlnAsnProAlaThr

TCCCAACATCCTCCTCCACCACCTGGTCATCGTTCCCAGGCACCTAGTCATCGTCCCCCG       (900)
SerGlnHisProProProProProGlyHisArgSerGlnAlaProSerHisArgProPro

CCTCCTGGACACCGTGTTCAGCACCAGCCTCAGAAGAGGCCTCCTGCTCCGTCGGGCACA       (960)
ProProGlyHisArgValGlnHisGlnProGlnLysArgProProAlaProSerGlyThr
```

FIG. 2A

```
    CAAGTTCACCAGCAGAAAGGCCCGCCCCTCCCCAGACCTCGAGTTCAGCCAAAACCTCCC   (1020)
300 GLNVALHISGLNGLNLYSGLYPROPROLEUPROARGPROARGVALGLNPROLYSPROPRO

CATGGGGCAGCAGAAAACTCATTGTCCCCTTCCTCTAATTAAAAAAGATAGAAACTGTCT   (1080)
320 HISGLYALAALAGLUASNSERLEUSERPROSERSERASNEND

TTTTCAATAAAAAGCACTGTGGATTTCTGCCCTCCTGATGTGCATATCCGTACTTCCATG   (1140)

AGGTGTTTTCTGTGTGCAGAACATTGTCACCTCCTGAGGCTGTGGGCCACAGCCACCTCT   (1200)

GCATCTTCGAACTCAGCCATGTGGTCAACATCTGGAGTTTTTGGTCTCCTCAGAGAGCTC   (1260)

CATCACACCAGTAAGGAGAAGCAATATAAGTGTGATTGCAAGAATGGTAGAGGACCGAGC   (1320)

ACAGAAATCTTAGAGATTTCTTGTCCCCTCTCAGGTCATGTGTAGATGCGATAAATCAAG   (1380)

TGATTGGTGTGCCTGGGTCTCACTACAAGCAGCCTATCTGCTTAAGAGACTCTGGAGTTT   (1440)

CTTATGTGCCCTGGTGGACACTTGCCCACCATCCTGTGAGTAAAAGTGAAATAAAAGCTT   (1500)

TGAC   (1504)
```

```
  1 GCCCGACGAGCCATGGTTGCTGGGAGGACGCGGGGCGGGCCCTGGGGTCCTCCAGCGTGCTGCCTCTGCCTGCACTGCTTCATC                  90
  1                  MetValAlaGlySerAspAlaGlyArgAlaLeuGlyValSerValValCysLeuLeuHisCysPheGlyPheIle          26

91 AGCTGTTTTCCCACCAACAAATATGGTGTTGTTGTATGGGAATGTAACTTTCCATGTACCAAGCAATGTGCCTTAAAAGAGGTCCTATGG           180
 27    SerCysPheSerGlnGlnIleTyrGlyValValTyrGlyAsnValThrPheHisValProSerAsnValProLeuLysGluValLeuTrp         56
                                          ---CHO---

181 AAAAAACAAAGGATAAAGTTGCAGAACTGGAAAATTCTGAATTCAGAGCTTTCTCATCTTTAAAAATAGGTTTATTTAGACACTGTG              270
 57 LysLysGlnLysAspLysAspLysValAlaGluLeuGluAsnSerGlnPheArgAlaPheSerSerPheLysAsnArgValTyrLeuAspThrVal      86

271 TCAGGTAGCCTCACTATCTACAACATCATCAGATGAAGATGAGTATGAAATGGAATCGCCAAATATTACTGATACCATGAAGTTC                360
 87 SerGlySerLeuThrIleTyrAsnLeuThrSerSerAspGluAspGluTyrGluMetGluSerProAsnIleThrAspThrMetLysPhe           116
                                                              ---CHO---

361 TTTCTTTATGTGCTTGAGTCTCTTCCATCTCCCACACTAACTGTGCATTGACTAATGGAAGTCCAATGCATGATACCAGAG                    450
117 PheLeuTyrValLeuGluSerLeuProSerProThrLeuThrValHisLeuThrAsnGlySerProMetHisAspThrArgGlu                 146
                                                                              ---CHO---

451 CATTACAACAGCCATCGAGGACTTATAATGTACTCTTATGGAGATTGTCCTATGGAGCAATGTAAACGTAACTCAACAGTATATATTTAAG           540
147 HisTyrAsnSerHisArgGlyLeuIleMetTyrSerTyrTrpAspCysProMetGluGlnCysLysArgAsnSerThrSerIleTyrPheLys         176
                                                                      ---CHO---

541 ATGGAAAATGATCTTCCACAAAAAATACAGTGTACTCTTAGCAATCCATTATTTAATACAACATCATCAATCATTTTGACAACCTGTATC           630
177 MetGluAsnAspLeuProGlnLysIleGlnCysThrLeuSerAsnProLeuPheAsnThrThrSerSerIleIleLeuThrThrCysIle          206
                                                                    ---CHO---

631 CCAAGCAGGGTCATTCAAGACACAGATATGCCACTTATACCCATAATTACACAGTAATTACAACATGTATTGTCTGTATATGAATGTT             720
207 ProSerSerGlyHisSerArgHisArgTyrAlaLeuIleProIleProLeuAlaValIleThrThrCysIleValLeuTyrMetAsnVal           236

721 CTTTAATTGAGAAGACAATTTCTTCATTTTTAGGTATTCTGAAATGTGACAGAACCAGAACCAACTCCAATTGATTGGTAACAG                 810
237 LeuEnd

811 AAGATGAAGACAACAGCATAACTAAATTATTTTAAAAACTAAAAAGCCATCTGATTTCTCATT                                      874
```

```
   1  GGCGTAATCT GCTGCTTGCA AACAAAAAAA CCACCGCTAC CAGCGGTGGT
  51  TTGTTTGCCG GATCAAGAGC TACCAACTCT TTTTCCGAAG GTAACTGGCT
 101  TCAGCAGAGC GCAGATACCA AATACTGTCC TTCTAGTGTA GCCGTAGTTA
 151  GGCCACCACT TCAAGAACTC TGTAGCACCG CCTACATACC TCGCTCTGCT
 201  AATCCTGTTA CCAGTGGCTG CTGCCAGTGG CGATAAGTCG TGTCTTACCG
 251  GGTTGGACTC AAGACGATAG TTACCGGATA AGGCGCAGCG GTCGGGCTGA
 301  ACGGGGGGTT CGTGCACACA GCCCAGCTTG GAGCGAACGA CCTACACCGA
 351  ACTGAGATAC CTACAGCGTG AGCATTGAGA AAGCGCCACG CTTCCCGAAG
 401  GGAGAAAGGC GGACAGGTAT CCGGTAAGCG GCAGGGTCGG AACAGGAGAG
 451  CGCACGAGGG AGCTTCCAGG GGGAAACGCC TGGTATCTTT ATAGTCCTGT
 501  CGGGTTTCGC CACCTCTGAC TTGAGCGTCG ATTTTTGTGA TGCTCGTCAG
 551  GGGGGCGGAG CCTATGGAAA AACGCCAGCA ACGCAAGCTA GCTTCTAGCT
 601  AGAAATTGTA AACGTTAATA TTTTGTTAAA ATTCGCGTTA AATTTTTGTT
 651  AAATCAGCTC ATTTTTTAAC CAATAGGCCG AAATCGGCAA AATCCCTTAT
 701  AAATCAAAAG AATAGCCCGA GATAGGGTTG AGTGTTGTTC CAGTTTGGAA
 751  CAAGAGTCCA CTATTAAAGA ACGTGGACTC CAACGTCAAA GGGCGAAAAA
 801  CCGTCTATCA GGGCGATGGC CGCCCACTAC GTGAACCATC ACCCAAATCA
 851  AGTTTTTTGG GGTCGAGGTG CCGTAAAGCA CTAAATCGGA ACCCTAAAGG
 901  GAGCCCCCGA TTTAGAGCTT GACGGGGAAA GCCGGCGAAC GTGGCGAGAA
 951  AGGAAGGGAA GAAAGCGAAA GGAGCGGGCG CTAGGGCGCT GGCAAGTGTA
1001  GCGGTCACGC TGCGCGTAAC CACCACACCC GCCGCGCTTA ATGCGCCGCT
1051  ACAGGGCGCG TACTATGGTT GCTTTGACGA GCACGTATAA CGTGCTTTCC
```

FIG. 6A

```
1101  TCGTTGGAAT CAGAGCGGGA GCTAAACAGG AGGCCGATTA AAGGGATTTT
1151  AGACAGGAAC GGTACGCCAG CTGGATCACC GCGGTCTTTC TCAACGTAAC
1201  ACTTTACAGC GGCGCGTCAT TTGATATGAT GCGCCCCGCT TCCCGATAAG
1251  GGAGCAGGCC AGTAAAAGCA TTACCCGTGG TGGGGTTCCC GAGCGGCCAA
1301  AGGGAGCAGA CTCTAAATCT GCCGTCATCG ACTTCGAAGG TTCGAATCCT
1351  TCCCCCACCA CCATCACTTT CAAAAGTCCG AAAGAAtCTG CTCCCTGCTT
1401  GTGTGTTGGA GGTCGCTGAG TAGTGCGCGA GTAAAATTTA AGCTACAACA
1451  AGGCAAGGCT TGACCGACAA TTGCATGAAG AATCTGCTTA GGGTTAGGCG
1501  TTTTGCGCTG CTTCGCGATG TACGGGCCAG ATATACGCGT TGACATTGAT
1551  TATTGACTAG TTATTAATAG TAATCAATTA CGGGGTCATT AGTTCATAGC
1601  CCATATATGG AGTTCCGCGT TACATAACTT ACGGTAAATG GCCCGCCTGG
1651  CTGACCGCCC AACGACCCCC GCCCATTGAC GTCAATAATG ACGTATGTTC
1701  CCATAGTAAC GCCAATAGGG ACTTTCCATT GACGTCAATG GGTGGACTAT
1751  TTACGGTAAA CTGCCCACTT GGCAGTACAT CAAGTGTATC ATATGCCAAG
1801  TACGCCCCCT ATTGACGTCA ATGACGGTAA ATGGCCCGCC TGGCATTATG
1851  CCCAGTACAT GACCTTATGG GACTTTCCTA CTTGGCAGTA CATCTACGTA
1901  TTAGTCATCG CTATTACCAT GGTGATGCGG TTTTGGCAGT ACATCAATGG
1951  GCGTGGATAG CGGTTTGACT CACGGGGATT TCCAAGTCTC CACCCCATTG
2001  ACGTCAATGG GAGTTTGTTT TGGCACCAAA ATCAACGGGA CTTTCCAAAA
2051  TGTCGTAACA ACTCCGCCCC ATTGACGCAA ATGGGCGGAA TTCCTGGGCG
2101  GGACTGGGGA GTGGCGAGCC CTCAGATGCT GCATATAAGC AGCTGCTTTT
2151  TGCCTGTACT GGGTCTCTCT GGTTAGACCA GATCTGAGCC TGGGAGCTCT
2201  CTGGCTAACT AGAGAACCCA CTGCTTAAGC CTCAATAAAG CTTCTAGAGA
2251  TCCCTCGACC TCGAGATCCA TTGTGCTGGC GCGGATTCTT TATCACTGAT
```

FIG. 6B

```
2301  AAGTTGGTGG ACATATTATG TTTATCAGTG ATAAAGTGTC AAGCATGACA
2351  AAGTTGCAGC CGAATACAGT GATCCGTGCC GCCCTAGACC TGTTGAACGA
2401  GGTCGGCGTA GACGGTCTGA CGACACGCAA ACTGGCGGAA CGGTTGGGGG
2451  TTCAGCAGCC GGCGCTTTAC TGGCACTTCA GGAACAAGCG GGCGCTGCTC
2501  GACGCACTGG CCGAAGCCAT GCTGGCGGAG AATCATAGCA CTTCGGTGCC
2551  GAGAGCCGAC GACGACTGGC GCTCATTTCT GACTGGGAAT GCCCGCAGCT
2601  TCAGGCAGGC GCTGCTCGCC TACCGCCAGC ACAATGGATC TCGAGGGATC
2651  TTCCATACCT ACCAGTTCTG CGCCTGCAGG TCGCGGCCGC GACTCTAGAG
2701  GATCTTTGTG AAGGAACCTT ACTTCTGTGG TGTGACATAA TTGGACAAAC
2751  TACCTACAGA GATTTAAAGC TCTAAGGTAA ATATAAAATT TTTAAGTGTA
2801  TAATGTGTTA AACTACTGAT TCTAATTGTT TGTGTATTTT AGATTCCAAC
2851  CTATGGAACT GATGAATGGG AGCAGTGGTG GAATGCCTTT AATGAGGAAA
2901  ACCTGTTTTG CTCAGAAGAA ATGCCATCTA GTGATGATGA GGCTACTGCT
2951  GACTCTCAAC ATTCTACTCC TCCAAAAAAG AAGAGAAAGG TAGAAGACCC
3001  CAAGGACTTT CCTTCAGAAT TGCTAAGTTT TTTGAGTCAT GCTGTGTTTA
3051  GTAATAGAAC TCTTGCTTGC TTTGCTATTT ACACCACAAA GGAAAAAGCT
3101  GCACTGCTAT ACAAGAAAAT TATGGAAAAA TATTCTGTAA CCTTTATAAG
3151  TAGGCATAAC AGTTATAATC ATAACATACT GTTTTTTCTT ACTCCACACA
3201  GGCATAGAGT GTCTGCTATT AATAACTATG CTCAAAAATT GTGTACCTTT
3251  AGCTTTTTAA TTTGTAAAGG GGTTAATAAG GAATATTTGA TGTATAGTGC
3301  CTTGACTAGA GATCATAATC AGCCATACCA CATTTGTAGA GGTTTTACTT
3351  GCTTTAAAAA ACCTCCCACA CCTCCCCCTG AACCTGAAAC ATAAAATGAA
3401  TGCAATTGTT GTTGTTAACT TGTTTATTGC AGCTTATAAT GGTTACAAAT
3451  AAAGCAATAG CATCACAAAT TTCACAAATA AAGCATTTTT TTCACTGCAT
```

FIG. 6C

```
3501  TCTAGTTGTG GTTTGTCCAA ACTCATCAAT GTATCTTATC ATGTCTGGAT
3551  CCTGTGGAAT GTGTGTCAGT TAGGGTGTGG AAAGTCCCCA GGCTCCCCAG
3601  CAGGCAGAAG TATGCAAAGC ATGCATCTCA ATTAGTCAGC AACCAGGTGT
3651  GGAAAGTCCC CAGGCTCCCC AGCAGGCAGA AGTATGCAAA GCATGCATCT
3701  CAATTAGTCA GCAACCATAG TCCCGCCCCT AACTCCGCCC ATCCCGCCCC
3751  TAACTCCGCC CAGTTCCGCC CATTCTCCGC CCCATGGCTG ACTAATTTTT
3801  TTTATTTATG CAGAGGCCGA GGCCGCCTCG GCCTCTGAGC TATTCCAGAA
3851  GTAGTGAGGA GGCTTTTTTG GAGGCCTAGG CTTTTGCAAA AAGCTAATTC
```

FIG. 6D

```
AGACTCTCAGGCCTTGGCAGGTGCGTCTTTCAGTTCCCCTCACACTTCGGGTTCCTCGGG          (60)

GAGGAGGGGCTGGAACCCTAGCCCATCGTCAGGACAAAGATGCTCAGGCTGCTCTTGGCT          (120)
                                     MetLeuArgLeuLeuLeuAla
                                         -18
CTCAACTTATTCCCTTCAATTCAAGTAACAGGAAACAAGATTTTGGTGAAGCAGTCGCCC          (180)
LeuAsnLeuPheProSerIleGlnValThrGlyAsnLysIleLeuValLysGlnSerPro
                                                         +1
     ATGCTTGTAGCGTACGACAATGCGGTCAACCTTAGCTGCAAGTATTCCTACAATCTCTTC     (240)
 10  MetLeuValAlaTyrAspAsnAlaValAsnLeuSerCysLysTyrSerTyrAsnLeuPhe
                                          ---CHO---
     TCAAGGGAGTTCCGGGCATCCCTTCACAAGGACTGGATAGTGCTGTGGAAGTCTGTGTT      (300)
 30  SerArgGluPheArgAlaSerLeuHisLysGlyLeuAspSerAlaValGluValCysVal
     GTATATGGAATTACTCCCAGCAGCTTCAGGTTTACTCAAAAACGGGGTTCAACTGTGAT      (360)
 50  ValTyrGlyAsnTyrSerArgGlnAsnLeuGlnValTyrSerLysThrGlyPheAsnCysAsp
                ---CHO---
     GGGAAATTGGGCAATGAATCAGTGACATTCTACCTCCAGAATTTGTATGTTAACCAAACA     (420)
 70  GlyLysLeuGlyAsnGluSerValThrPheTyrLeuGlnAsnLeuTyrValAsnGlnThr
             ---CHO---                                 ---CHO---
     GATATTTACTTCTGCAAAATTGAAGTTATGTATCCTCCTCCTTACCTAGACAATGAGAAG     (480)
 90  AspIleTyrPheCysLysIleGluValMetTyrProProProTyrLeuAspAsnGluLys
     AGCAATGGAACCATTATCCATGTGAAAGGGAAACACCTTTGTCCAAGTCCCCTATTTCCC     (540)
110  SerAsnGlyThrIleIleHisValLysGlyLysHisLeuCysProSerProLeuPhePro
         ---CHO---
     GGACCTTCTAAGCCCTTTTGGGTGCTGGTGGTGGTTGGTGGAGTCCTGGCTTGCTATAGC     (600)
130  GlyProSerLysProPheTrpValLeuValValValGlyGlyValLeuAlaCysTyrSer
                                             ------------TM-------
     TTGCTAGTAACAGTGGCCTTTATTATTTTCTGGGTGAGGAGTAAGAGGAGCAGGCTCCTG     (660)
150  LeuLeuValThrValAlaPheIleIlePheTrpValArgSerLysArgSerArgLeuLeu
     CACAGTGACTACATGAACATGACTCCCCGCCGCCCCGGGCCCACCCGCAAGCATTACCAG     (720)
170  HisSerAspTyrMetAsnMetThrProArgArgProGlyProThrArgLysHisTyrGln
     CCCTATGCCCCACCACGCGACTTCGCAGCCTATCGCTCCTGACACGGACGCCTATCCAGA     (780)
190  ProTyrAlaProProArgAspPheAlaAlaTyrArgSerEnd
                                           202.
     AGCCAGCCGGCTGGCAGCCCCCATCTGCTCAATATCACTGCTCTGGATAGGAAATGACCG     (840)

CCATCTCCAGCCGGCCACCTCAGCCCCTGTTGGGCCACCAATGCCAATTTTTCTCGAGTG     (900)

ACTAGACCAAATATCAAGATCATTTTGAGACTCTGAAATGAAGTAAAAGAGATTTCCTGT     (960)

GACAGGCCAAGTCTTACAGTGCCATGGCCCACATTCCAACTTACCATGTACTTAGTGACT     (1020)

TGACTGAGAAGTTAGGGTAGAAAACAAAAAGGGAGTGGATTCTGGGAGCCTCTTCCCTTT     (1080)
```

FIG. 7A

```
CTCACTCACCTGCACACATCTCAGTCAAGCAAAGTGTGGTATCCACAGACATTTTAGTTGCA   (1140)
GAAGAAAGGCTAGGAAATCATTCCTTTTGGTTAAATGGGTGTTTAATCTTTTGGTTAGTG    (1200)
GGTTAAACGGGGTAAGTTAGAGTAGGGGGAGGGATAGGAAGACATATTTAAAAACCATTA    (1260)
AAACACTGTCTCCCACTCATGAAATGAGCCACGTAGTTCCTATTTAATGCTGTTTTCCTT    (1320)
TAGTTTAGAAATACATAGACATTGTCTTTTATGAATTCTGATCATATTTAGTCATTTTGA    (1380)
CCAAATGAGGGATTTGGTCAAATGAGGGATTCCCTCAAAGCAATATCAGGTAAACCAAGT    (1440)
TGCTTTCCTCACTCCCTGTCATGAGACTTCAGTGTTAATGTTCACAATATACTTTCGAAA    (1500)
GAATAAAATAGTTC   (1514)
```

FIG. 7B

```
TAGACCCAGAGAGGCTCAGCTGCACTCGCCCGGCTGGGAGAGCTGGGTGTGGGGAACATG     (60)
                                                            MET

GCCGGGCCTCCGAGGCTCCTGCTGCTGCCCCTGCTTCTGGCGCTGGCTCGCGGCCTGCCT    (120)
AlaGlyProProArgLeuLeuLeuLeuProLeuLeuLeuAlaLeuAlaArgGlyLeuPro

GGGGCCCTGGCTGCCCAAGGTAAGAGCTTCCCAGGCTCTCCATGGCCACAGCTCCGGAGC    (180)
GlyAlaLeuAlaAlaGln /

TCTCCCTGCCCCATGAGCTCAGAGCCCCCAGTCTGAGCCACAGCACAGCCCCCAGGAAGC    (240)

GGGTGGGGTGCTGAGCGGCCTCCAGTGTCTGAGGACTCATTTAAGAGAAGGAAAAAGGGT    (300)

GGACCCGGTGGGGAGTGGCCGGGGCTGTCCAGGCAGGGCCGCTGCTTTGGGAGGAAGAAG    (360)

CCCACAGTCTCGGAACACGAGGACAGCACCTCCCCCAACACCACAGCCGGTGCCCAGATC    (420)

TGCTCCATGCCCCGTAAGGCACCGTGTCTTTGGCGACATGTCAGCCCTGGGCTGTCTCAG    (480)

GGCCCCACCATCCCCACCACTGTCCCCTGCAGGGAGGACATTCTCTGTCCTTCTGGCCAG    (540)
                          /
ACTGATGGTGACAGCCCAGGTCCTCCCAGAGGTGCAGCAGTCTCCCCACTGCACGACTGT    (600)
                                    GluValGlnGlnSerProHisCysThrThrVa

CCCCGTGGGAGCCTCCGTCAACATCACCTGCTCCACCAGCGGGGGCCTGCGTGGGATCTA    (660)
lProValGlyAlaSerValAsnIleThrCysSerThrSerGlyGlyLeuArgGlyIleTy
                                      ---CHO---
CCTGAGGCAGCTCGGGCCACAGCCCCAAGACATCATTTACTACGAGGACGGGGTGGTGCC    (720)
rLeuArgGlnLeuGlyProGlnProGlnAspIleIleTyrTyrGluAspGlyValValPr

CACTACGGACAGACGGTTCCGGGGCCGCATCGACTTCTCAGGGTCCCAGGACAACCTGAC    (780)
oThrThrAspArgArgPheArgGlyArgIleAspPheSerGlySerGlnAspAsnLeuTh
                                                    ---CHO--
TATCACCATGCACCGCCTGCAGCTGTCGGACACTGGCACCTACACCTGCCAGGCCATCAC    (840)
rIleThrMetHisArgLeuGlnLeuSerAspThrGlyThrTyrThrCysGlnAlaIleTh

GGAGGTCAATGTCTACGGCTCCGGCACCCTGGTCCTGGTGACAGAGGAACAGTCCCAAGG    (900)
rGluValAsnValTyrGlySerGlyThrLeuValLeuValThrGluGluGlnSerGlnGl

ATGGCACAGATGCTCGGACGCCCCACCAAGGGCCTCTGCCCTCCCTGCCCCACCGACAGG    (960)
yTrpHisArgCysSerAspAlaProProArgAlaSerAlaLeuProAlaProProThrGl

CTCCGCCCTCCCTGACCCGCAGACAGCCTCTGCCCTCCCTGACCCGCCAGCAGCCTCTGC    (1020)
ySerAlaLeuProAspProGlnThrAlaSerAlaLeuProAspProProAlaAlaSerAl

CCTCCCTGCGGCCCTGGCGGTGATCTCCTTCCTCCTCGGGCTGGGCCTGGGGGTGGCGTG    (1080)
aLeuProAlaAlaLeuAlaValIleSerPheLeuLeuGlyLeuGlyLeuGlyValAlaCy
------------------------------------TM------------------*
```

FIG. 8A

```
TGTGCTGGCGAGGACACAGATAAAGAAACTGTGCTCGTGGCGGGATAAGAATTCGGCGGC     (1140)
 sValLeuAlaArgThrGlnNIleLysLysLeuCysSerTrpArgAspLysAsnSerAlaAl
ATGTGTGGTGTACGAGGACATGTCGCACAGCCGCTGCAACACGCTGTCCTCCCCCAACCA     (1200)
 aCysValValTyrGluAspMetSerHisSerArgCysAsnThrLeuSerSerProAsnGl
GTACCAGTGACCCAGTGGGCCCCTGCACGTCCCGCCTGTGGTCCCCCCAGCACCTTCCCT    (1260)
 nTyrGlnEnd
GCCCCACCATGCCCCCCACCCTGCCACACCCCTCACCCTGCTGTCCTCCCACGGCTGCAG     (1320)
CAGAGTTTGAAGGGCCCAGCCGTGCCCAGCTCCAAGCAGACACACAGGCAGTGGCCAGGC     (1380)
CCCACGGTGCTTCTCAGTGGACAATGATGCCTCCTCCGGGAAGCCTTCCCTGCCCAGCCC     (1440)
ACGCCGCCACCGGGAGGAAGCCTGACTGTCCTTTGGCTGCATCTCCCGACCATGGCCAAG     (1500)
GAGGGCTTTTCTGTGGGATGGGCCTGGCACGCGGCCCTCTCCTGTCAGTGCCGGCCCACC     (1560)
CACCAGCAGGCCCCCAACCCCCAGGCAGCCCGGCAGAGGACGGGAGGAGACCAGTCCCCC    (1620)
ACCCAGCCGTACCAGAAATAAAGGCTTCTGTGCTTCAAAAAAAAA  (1665)
```

FIG. 8B

```
      CCCAAATGTCTCAGAATGTATGTCCCAGAAACCTGTGGCTGCTTCAACCATTGACAGTTT      (60)
          METSERGLNASNVALCYSPROARGASNLEUTRPLEULEUGLNPROLEUTHRVALL
          -29
      TGCTGCTGCTGGCTTCTGCAGACAGTCAAGCTGCAGCTCCCCCAAAGGCTGTGCTGAAAC      (120)
          EULEULEULEUALASERALAASPSERGLNALAALAALAPROPROLYSALAVALLEULYSL
                                                               -1 +1
      TTGAGCCCCCGTGGATCAACGTGCTCCAGGAGGACTCTGTGACTCTGACATGCCAGGGGG      (180)
10    EUGLUPROPROTRPILEASNVALLEUGLNGLUASPSERVALTHRLEUTHRCYSGLNGLYA
                                                                 *
      CTCGCAGCCCTGAGAGCGACTCCATTCAGTGGTTCCACAATGGGAATCTCATTCCCACCC      (240)
30    LAARGSERPROGLUSERASPSERILEGLNTRPPHEHISASNGLYASNLEUILEPROTHRH
      ACACGCAGCCCAGCTACAGGTTCAAGGCCAACAACAATGACAGCGGGGAGTACACGTGCC      (300)
50    ISTHRGLNPROSERTYRARGPHELYSALAASNASNASNASPSERGLYGLUTYRTHRCYSG
                                      ---CHO---                 *
      AGACTGGCCAGACCAGCCTCAGCGACCCTGTGCATCTGACTGTGCTTTCCGAATGGCTGG      (360)
70    LNTHRGLYGLNTHRSERLEUSERASPPROVALHISLEUTHRVALLEUSERGLUTRPLEUV
      TGCTCCAGACCCCTCACCTGGAGTTCCAGGAGGGAGAAACCATCATGCTGAGGTGCCACA      (420)
90    ALLEUGLNTHRPROHISLEUGLUPHEGLNGLUGLYGLUTHRILEMETLEUARGCYSHISS
                                                              *
      GCTGGAAGGACAAGCCTCTGGTCAAGGTCACATTCTTCCAGAATGGAAAATCCCAGAAAT      (480)
110   ERTRPLYSASPLYSPROLEUVALLYSVALTHRPHEPHEGLNASNGLYLYSSERGLNLYSP
      TCTCCCGTTTGGATCCCACCTTCTCCATCCCACAAGCAAACCACAGTCACAGTGGTGATT      (540)
130   HESERARGLEUASPPROTHRPHESERILEPROGLNALAASNHISSERHISSERGLYASPT
                                                  ---CHO---
      ACCACTGCACAGGAAACATAGGCTACACGCTGTTCTCATCCAAGCCTGTGACCATCACTG      (600)
150   YRHISCYSTHRGLYASNILEGLYTYRTHRLEUPHESERSERLYSPROVALTHRILETHRV
                                                                *
      TCCAAGTGCCCAGCATGGGCAGCTCTTCACCAATGGGGATCATTGTGGCTGTGGTCATTG      (660)
170   ALGLNVALPROSERMETGLYSERSERSERPROMETGLYILEILEVALALAVALVALILEA
                                  ------------------------------
      CGACTGCTGTAGCAGCCATTGTTGCTGCTGTAGTGGCCTTGATCTACTGCAGGAAAAAGC      (720)
190   LATHRALAVALALAALAILEVALALAALAVALVALALALEUILETYRCYSARGLYSLYSA
      ----------TM-----------------------------------------*-
      GGATTTCAGCCAATTCCACTGATCCTGTGAAGGCTGCCCAATTTGAGCCACCTGGACGTC      (780)
210   RGILESERALAASNSERTHRASPPROVALLYSALAALAGLNPHEGLUPROPROGLYARGG
      AAATGATTGCCATCAGAAAGAGACAACTTGAAGAAACCAACAATGACTATGAAACAGCTG      (840)
230   LNMETILEALAILEARGLYSARGGLNLEUGLUGLUTHRASNASNASPTYRGLUTHRALAA
      ACGGCGGCTACATGACTCTGAACCCCAGGGCACCTACTGACGATGATAAAAACATCTACC      (900)
250   SPGLYGLYTYRMETTHRLEUASNPROARGALAPROTHRASPASPASPLYSASNILETYRL
```

FIG. 9A

```
          TGACTCTTCCTCCCAACGACCATGTCAACAGTAATAACTAAAGAGTAACGTTATGCCATG     (960)
   270    EuThrLeuProProAsnAspHisValAsnSerAsnAsnEnd
                                            282
          TGGTCATACTCTCAGCTTGCTGAGTGGATGACAAAAAGAGGGGAATTGTTAAAGGAAAAT    (1020)
          TTAAATGGAGACTGGAAAAATCCTGAGCAAACAAAACCACCTGGCCCTTAGAAATAGCTT    (1080)
          TAACTTTGCTTAAACTACAAACACAAGCAAAACTTCACGGGGTCATACTACATACAAGCA    (1140)
          TAAGCAAAACTTAACTTGGATCATTTCTGGTAAATGCTTATGTTAGAAATAAGACAACCC    (1200)
          CAGCCAATCACAAGCAGCCTACTAACATATAATTAGGTGACTAGGGACTTTCTAAGAAGA    (1260)
          TACCTACCCCCAAAAAACAATTATGTAATTGAAAACCAACCGATTGCCTTTATTTTGCTT    (1320)
          CCACATTTTCCCAATAAATACTTGCCTGTGACATTTTGCCACTGGAACACTAAACTTCAT    (1380)
          GAATTGCGCCTCAGATTTTTCCTTTAACATCTTTTTTTTTTTTGACAGAGTCTCAATCTG    (1440)
          TTACCCAGGCTGGAGTGCAGTGGTGCTATCTTGGCTCACTGCAAACCCGCCTCCCAGGTT    (1500)
          TAAGCGATTCTCATGCCTCAGCCTCCCAGTAGCTGGGATTAGAGGCATGTGCCATCATAC    (1560)
          CCAGCTAATTTTTGTATTTTTTATTTTTTTTTTTTAGTAGAGACAGGGTTTCGCAATGTT    (1620)
          GGCCAGGCCGATCTCGAACTTCTGGCCTCTAGCGATCTGCCCGCCTCGGCCTCCCAAAGT    (1680)
          GCTGGGATGACCAGCATCAGCCCCAATGTCCAGCCTCTTTAACATCTTCTTTCCTATGCC    (1740)
          CTCTCTGTGGATCCCTACTGCTGGTTTCTGCCTTCTCCATGCTGAGAACAAAATCACCTA    (1800)
          TTCACTGCTTATGCAGTCGGAAGCTCCAGAAGAACAAAGAGCCCAATTACCAGAACCACA    (1860)
          TTAAGTCTCCATTGTTTTGCCTTGGGATTTGAGAAGAGAATTAGAGAGGTGAGGATCTGG    (1920)
          TATTTCCTGGACTAAATTCCCCTTGGGGAAGACGAAGGGATGCTGCAGTTCCAAAAGAGA    (1980)
          AGGACTCTTCCAGAGTCATCTACCTGAGTCCCAAAGCTCCCTGTCCTGAAAGCCACAGAC    (2040)
          AATATGGTCCCAAATGACTGACTGCACCTTCTGTGCCTCAGCCGTTCTTGACATCAAGAA    (2100)
          TCTTCTGTTCCACATCCACACAGCCAATACAATTAGTCAAACCACTGTTATTAACAGATG    (2160)
          TAGCAACATGAGAAACGCTTATGTTACAGGTTACATGAGAGCAATCATGTAAGTCTATAT    (2220)
          GACTTCAGAAAATGTTAAAATAGACTAACCTCTAACAACAAATTAAAAGTGATTGTTTCAA    (2280)
          GGTGAAAAAA    (2290)
```

FIG. 9B

```
  1 AAAGACAAACTGCACCCACTGAACTCCGCAGCTAGCATCCAAATCAGCCCTTGAGATTTGAGGACTCAGGAGTTTGAGAGC

91 AAAATGACAACACCCAGAAATTCAGTAAATGGGACTTTCCGGCAGAGCCAATGAAAGCCCTATTGCTATGCAATCTGGTCCAAAACCA
  1 MetThrThrProArgAsnSerValAsnGlyThrPheProAlaGluProMetLysGlyProMetLysGlnSerGlyProLysPro
                                                 ---CHO---

181 CTCTTCAGGAGGATGTCTTCACTGGTGGGCCCCACGCCAAAGCTTCTTCATGAGGAATCTAAGACTTTGGGGGCTGTCCAGATTATGAAT
 30 LeuPheArgArgMetSerSerLeuValGlyProThrGlnSerPhePheMetArgGlnSerLysThrLeuGlyAlaValGlnIleMetAsn
                                                                    ===================

271 GGGCTCTTCCACATTGCCCTGGGGGTCTTCTGATGATCCCAGCAGGATCTATGCACCATCTGTGTGTGTACCCTCTGG
 60 GlyLeuPheHisIleAlaLeuGlyValPheLeuMetIleProAlaGlyIleTyrAlaProIleCysValThrValTrpTyrProLeuTrp
    ==============================================================================

361 GGAGGCATTATGTATATTATTTCCGGATCACTCCTGGCAGCAACGGAGAAAAACTCCAGGAAGTGTTGGTCAAAGGAAAATGATAATG
 90 GlyGlyIleMetTyrIleIleSerGlyIleLeuLeuLeuAlaAlaThrGluLysAsnSerArgLysCysLeuValLysGlyLysMetIleMet
    ==========================================================================================

451 AATTCATTGAGCCTCTTTGCTGCCATTTCTGGAATGATTCTTCAATCATGGACATACTTAATATTAAATTTCCATTTTTTAAAAATG
120 AsnSerLeuSerLeuPheAlaAlaIleSerGlyMetIleLeuSerIleMetAspIleLeuAsnIleLeuSerHisPheLeuLysMet
    =================================================================

541 GAGAGTCTGAATTTTATTAGAGCTCACACAACCATATATTAACATATACAACTGTGAACCAGTGAATCCCCTCTGAGAAAACTCCCCATCT
150 GluSerLeuAsnPheIleArgAlaHisThrProTyrIleAsnIleTyrAsnCysGluProAlaAsnProSerGluLysAsnProSer

631 ACCCAATACTGTTACAGCATACAATCTCTGTTCTTGGGCATTTGTCAGTGATGCTGATCTTTGCCTTCTTCCAGGAACTTGTAATAGCT
180 ThrGlnTyrCysTyrSerIleGlnSerLeuPheLeuGlyIleLeuPheAlaPhePheGlnGluLeuValIleAla
```

FIG. 10A

```
721  GGCATCGTTGAGAATGAATGGAAAGAACGTGCTCCAGACCCAAATCTAACATAGTTCTCCTGTCAGCAGAAGAAAAAGAACAGACT
210  GlyIleValGluAsnGluTrpLysArgThrCysSerArgProLysSerAsnIleValLeuLeuSerAlaGluLysLysGluGlnThr

811  ATTGAAATAAAAGAGAAGAAGTGGTTGGGCTAACTGAAACATCTTCCAACCAAAGAATGAAGAGACATTGAAATTATTCCAAGAA
240  IleGluIleLysGluLysGluValValGlyLeuThrGluThrSerSerGlnProLysAsnGluGluAspIleGluIleIleProIleGluGln Glu

901  GAGGAAGAAGAAGAAACAGAGACGAACTTTCCAGAACCTCCCCAAGATCAGGAATCCTCACCAATAGAAAATGACAGCTCTCCTTAAGTG
270  GluGluGluGluGluThrGluThrAsnPheProGluProProGlnAspGlnGluSerProIleGluAsnAspSerSerProEnd 297
                                                                   ---CHO---

991  ATTTCTCTGTTTCTGTTTCCTTTTTAAACATTAGTGTTCATAGCTTCCAAGAGACATGCTGACTTTCATTTCTTGAGGTACTCTGCA
                                                      *

1081 CATACGCGCACCACATCTCTATCTGGCCTTTGCATGGAGTGACCATAGCTCCTCTCTCCTTACATTGAATGTAGAGAATGTAGCCATTGTAG

1171 CAGCTTGTGTTGTCACGCTTCTTCTTTTGAGCAACTTTCTTACACTGAAGAAAGGCAGAATGAGTGCTTCAGAATGTGATTTCCTACTAA

1261 CCTGTTCCTTGGATAGGCTTTTTAGTATAGTATTTTTTTGTCATTTTCTCCATCAGCAACCAGGGAGACTGCACCTGATGGAAAAGAT

1351 ATATGACTGCTTCATGACATTCCTAAACTATCTTTTTTTATTCCACATCTACGTTTTGGTGGAGTCCCTTTTATCATCCTAAAACA

1441 ATGATGCAAAAGGGCTTTAGAGCACAATGGATCT  1474
```

FIG. 10B

```
  1   CTCAGCCTCGCTATGGCTCCCAGCAGCCCCGGCCCCGGCCACTCCTGGTCCTGCTCGGGCTCTGTTCCA
                   MetAlaProSerSerProArgProAlaLeuProAlaLeuLeuGlyAlaLeuPhePro
                   (-25)
      GGACCTGGCAATGCCCAGACATCTGTGTCCCCTCAAAAGTC
      GlyProGlyAsnAlaGlnThrSerValSerProSerLysVal
                                               (+1)
121   ATCCTGCCCCGGGGAGGCTCCGTGCTGGTGACATGCAGCACCTCCTGTGACCAGCCCAAGTTGTGGGCATAGAGACC
      IleLeuProArgGlyGlySerValLeuValThrCysSerThrSerCysAspGlnProLysLeuLeuGlyIleGluThr
                                                                                 (+11)
      CCGTTGCCTAAAAAGGAGTTGCTCCTGCCTGGGAACAACCGG
      ProLeuProLysLysGluLeuLeuLeuProGlyAsnAsnArg
                                               (+51)
241   AAGGTGTATGAACTGAGCAATGTGCAAGAAGATAGCAACCAATGTCTATTCAAACTGCCCTGATGGCAGTCAACA
      LysValTyrGluLeuSerAsnValGlnGluAspSerAsnGlnCysTyrSerAsnCysProAspGlySerThr
      GCTAAAACCTTCTCACCGTGTACTGGACTCCAGAACGGGTG
      AlaLysThrPheLeuThrValTyrTrpThrProGluArgVal
                                               (+91)
361   GAACTGGCACCCCTCCCCTCTTGGCCAAGAACCTTACCCTACGCTGCCAGGTGGAGGTGGGCCACCC
      GluLeuAlaProLeuProSerTrpProValGlyLysAsnLeuThrLeuArgCysGlnValGlyGlyAlaPro
                                                                 ---CHO---
      CGGGCCAACCTCACCGTGTCTTCCTGCTCCTGTGGGGAGAAGGAG
      ArgAlaAsnLeuThrValValLeuLeuArgGlyGluLysGlu
                                               (+131)
481   CTGAAACGGGAGCCAGCTGTGGGGAGCCGCTGAGCTGAGGTGGTGAGGAGAGATCACCATGGAGCC
      LeuLysArgGluProAlaValGlyProAlaGluValThrThrThrValLeuValArgArgAspHisHisGlyAla
      AATTTCTGCCCACTGAACTGACCTGCGGCCCCAAGGG
      AsnPheSerCysArgProLeuAspLeuArgProGlnGly
                                               (+171)
601   CTGGAGCTGTTGAGAACACCTCGGCCCCTACCAGTCCAGACCTTGTCCTGCCAGCGACTCCCCACAACTTGTC
      LeuGluLeuPheGluAsnThrSerAlaProTyrGlnLeuGlnThrPheValLeuProAlaThrProGlnLeuVal
                                            ---CHO---
      AGCCCCCGGGTCCTAGAGGTGGACACGCAGGGACCGGTGTC
      SerProArgValLeuGluValAspThrGlnGlyThrValVal
                                               (+211)
```

FIG. 11A

```
721   TGTTCCCTGGACGGGGCTGTGTTCCCAGTCTCGGAGGCCCAGGTCCACCTGGGGGACCAGAGGTTGAACCCCACA
      CysSerLeuAspGlyLeuPheProValSerGluAlaGlnValHisLeuAlaLeuGlyAspGlnArgLeuAsnProThr

GTCACCTATGGCAACGACTCCTTCTCGGCCAGGCCTCAGTC
      ValThrTyrGlyAsnAspSerPheSerAlaLysSerVal
            ---CHO---                     (+251)

841   AGTGTGACCGCAGAGGACGAGGGCACCCAGCGGCTGACGTGTGCAGTAATACTGGGGAACCAGAGCCAGGAGACACTG
      SerValThrAlaGluAspGluGlyThrGlnArgLeuThrCysAlaValIleLeuGlyAsnGlnSerGlnGluThrLeu
                                                                      ---CHO---

CAGACAGTGACCATCTACAGCTTTCCGGCCCCCAACGTGATT
      GlnThrValThrIleTyrSerPheProAlaProAsnValIle
                                                (+291)

961   CTGACGAAGCCAGAGGTCTCAGAAGGGACCGAGTGACAGTGAAGTGTGAGGCCCACCCTAGAGCCAAGGTGACGCTG
      LeuThrLysProGluValSerGluGlyThrGluValThrValLysCysGluAlaHisProArgAlaLysValThrLeu

AATGGGGTTCCAGCCCAGCAGCCACTGGGCCCGAGGGCCCAGCTC
      AsnGlyValProAlaGlnProLeuGlyProArgAlaGlnLeu
                                                  (+331)

1081  CTGCTGAAGGCCACCCAGAGGACAACCCCTGGAGCCAGCTTCTCCTGCTCTGCAACCCTGAGGTGGCCGGCCAGCTTATA
      LeuLeuLysAlaThrProGluAspAsnProGluSerPheSerCysSerAlaThrLeuGluValAlaGlyGlnLeuIle

CACAAGAACAGAGACCCCGGAGCTTCGTGTCCTGTCCTGTATGGCCCC
      HisLysAsnGlnThrArgLeuArgValLeuArgValLeuTyrGlyPro
                                                      (+371)

1201  CGACTGGACGAGAGGGATTGTCCGGGAAACTGGACGTGGCCAGAAAATTCCCAGCAGACTCCAATGTGCCAGGCTTGG
      ArgLeuAspAspGluArgAspCysProGlyAsnTrpThrTrpProGluAsnSerGlnThrProMetCysGlnAlaTrp
                                                                ---CHO---

GGGAACCCATTGCCCGAGCTCAAGTGTCTAAAGGATGGCACT
      GlyAsnProLeuProGluLeuLysCysLeuLysAspGlyThr
                                                (+411)

1321  TTCCCACTGCCCATCGGGGAATCAGTGACTGTCACTGAGATCTTGAGGGCACTTACCTCTGTGGGCCAGGAGCACT
      PheProLeuProIleGlyGluSerValThrValThrArgAspLeuGlyThrTyrLeuCysArgAlaArgSerThr

CAAGGGGAGGTCACCCGCGAGGTGACCGTGAATGTGCTCTCC
      GlnGlyGluValThrArgGluValThrValAsnValLeuSer
                                                (+451)
```

FIG. 11B

1441 CCCCGGTATGAGATTGTCATCATCACTGTGTAGCAGCCAGTCATAATGGGCACTGCAGGCCTCAGCACGTACCTC
ProArgTyrGluIleValIleIleThrValValAlaAlaAlaValIleMetGlyThrAlaGlyLeuSerThrTyrLeu
--------------------------------------TM------------

TATAACCGCCAGCGGAAGATCAAGAAATACAGACTACAACAG
TyrAsnArgGlnArgLysIleLysTyrArgLeuGlnGln
(+491)

1561 GCCCAAAAAGGGACCCCCATGAACCGAACACACAAGCCACGCCCTCCCTGAACCTATCCCGGGACAGGGCCTCTTCCT
AlaGlnLysGlyThrProMetLysProAsnThrGlnAlaThrProPro
(+507)

CGGCCTTCCCATATTGGTGGCAGTGGTGCCACACTGAACAGA

1681 GTGGAAGACATATGCCATGCAGCTACACCTACCGGCCCTGGGACGCCGGAGGACAGGGCATTGTCCCTCAGTCAGATAC
1801 GGCCACGCCATCTGATCTGTAGTCACATGACTAAGCCAAGAGGAAGG
AACAGCATTTGGGGCCATGGTACCTGCACACCTAAAACACTA

FIG. 11C

```
   1 ..GGAGAGTC TGACCACCAT GCCACCTCCT CGCCTCCTCT TCTTCCTCCT
  51 CTTCCTCACC CCCATGGAAG TCAGGCCCGA GGAACCTCTA GTGGTGAAGG
 101 TGGAAGAGGG AGATAACGCT GTGCTGCAGT GCCTCAAGGG GACCTCAGAT
 151 GGCCCCACTC AGCAGCTGAC CTGGTCTCGG GAGTCCCCGC TTAAACCCTT
 201 CTTAAAACTC AGCCTGGGGC TGCCAGGCCT GGGAATCCAC ATGAGGCCCC
 251 TGGcCATCTG GCTTTTCATC TTCAACGTCT CTCAACAGAT GGGGGGCTTC
 301 TACCTGTGCC AGCCGGGGCC CCCCTCTGAG AAGGCCTGGC AGCCTGGCTG
 351 GACAGTCAAT GTGGAGGGCA GCGGGGAGCT GTTCCGGTGG AATGTTTCGG
 401 ACCTAGGTGG CCTGGGCTGT GGCCTGAAGA ACAGGTCCTC AGAGGGCCCC
 451 AGCTCCCCTT CCGGGAAGCT CATGAGCCCC AAGCTGTATG TGTGGGCCAA
 501 AGACCGCCCT GAGATCTGGG AGGGAGAGCC TCCGTGTGTC CCACCGAGGG
 551 ACAGCCTGAA CCAGAGCCTC AGCCAGGACC TCACCATGGC CCCTGGCTCC
 601 ACACTCTGGC TGTCCTGTGG GGTACCCCCT GACTCTGTGT CCAGGGGCCC
 651 CCTCTCCTGG ACCCATGTGC ACCCCAAGGG GCCTAAGTCA TTGCTGAGCC
 701 TAGAGCTGAA GGACGATCGC CCGGCCAGAG ATATGTGGGT AATGGAGACG
 751 GGTCTGTTGT TGCCCCGGGC CACAGCTCAA GACGCTGGAA AGTATTATTG
 801 TCACCGTGGC AACCTGACCA TGTCATTCCA CCTGGAGATC ACTGCTCGGC
 851 CAGTACTATG GCACTGGCTG CTGAGGACTG GTGGCTGGAA GGTCTCAGCT
 901 GTGACTTTGG CTTATCTGAT CTTCTGCCTG TGTTCCCTTG TGGGCATTCT
 951 TCATCTTCAA AGAGCCCTGG TCCTGAGGAG GAAAAGAAAG CGAATGACTG
1001 ACCCCACCAG GAGATTCTTC AAAGTGACGC CTCCCCCAGG AAGCGGGCCC
1051 CAGAACCAGT ACGGGAACGT GCTGTCTCTC CCCACACCCA CCTCAGGCCT
1101 CGGACGCGCC CAGCGTTGGG CCGCAGGCCT GGGGGGCACT GCCCCGTCTT
1151 ATGGAAACCC GAGCAGCGAC GTCCAGGCGG ATGGAGCCTT GGGGTCCCGG
```

FIG. 12A

```
1201  AGCCGCCGGG AGTGGGCCCA GAAGAAGAGG AAGGGGAGGG CTATGAGGAA
1251  CCTGACAGTG AGGAGGACTC CGAGTTCTAT GAGAACGACT CCAACCTTGG
1301  GCAGGACCAG CTCTCCCAGG ATGGCAGCGG CTACGAGAAC CCTGAGGATG
1351  AGCCCCTGGG TCCTGAGGAT GAAGACTCCT TCTCCAACGC TGAGTCTTAT
1401  GAGAACGAGG ATGAAGAGCT GACCCAGCCG GTCGCCAGGA CAATGGACTT
1451  CCTGAGCCCT CATGGGTCAG CCTGGGACCC CAGCCGGGAA GCAACCTCCC
1501  TGGGGTCCCA GTCCTATGAG GATATGAGAG GAATCCTGTA TGCAGCCCCC
1551  CAGCTCCGCT CCATTCGGGG CCAGCCTGGA CCCAATCATG AGGAAGATGC
1601  AGACTCTTAT GAGAACATGG ATAATCCCGA TGGGCCAGAC CCAGCCTGGG
1651  GAGGAGGGGG CCGCATGGGC ACCTGGAGCA CCAGGTGATC CTCAGGTGGC
1701  CAGCCTGGAT CTCCTCAAGT CCCCAAGATT CACACCTGAC TCTGAAATCT
1751  GAAGACCTCG AGCAGATGAT GCCAACCTCT GGAGCAATGT TGCTTAGGAT
1801  GTGTGCATGT GTGTAAGTGT GTGTGTGTGT GTGTGTGTGT GTGTGTGTGT
1851  ATACATGCCA GTGACACTTC CAGTCCCCTT TGTATTCCTT AAATAAACTC
1901  AATGAGCTCT TCCAAAAAAA AAAA
```

FIG. 12B

```
   1  ACAAAGACAA ACTGCACCCA CTGAACTCCG CAGCTAGCAT CCAAATCAGC
  51  CCTTGAGATT TGAGGCCTTG GAGACTCAGG AGTTTTGAGA GCAAAATGAC
 101  AACACCCAGA AATTCAGTAA ATGGGACTTT CCCGGCAGAG CCAATGAAAG
 151  GCCCTATTGC TATGCAATCT GGTCCAAAAC CACTCTTCAG GAGGATGTCT
 201  TCACTGGTGG GCCCCACGCA AAGCTTCTTC ATGAGGGAAT CTAAGACTTT
 251  GGGGGCTGTC CAGATTATGA ATGGGCTCTT CCACATTGCC CTGGGGGGTC
 301  TTCTGATGAT CCCAGCAGGG ATCTATGCAC CCATCTGTGT GACTGTGTGG
 351  TACCCTCTCT GGGGAGGCAT TATGTATATT ATTTCCGGAT CACTCCTGGC
 401  AGCAACGGAG AAAAACTCCA GGAAGTGTTT GGTCAAAGGA AAAATGATAA
 451  TGAATTCATT GAGCCTCTTT GCTGCCATTT CTGGAATGAT TCTTTCAATC
 501  ATGGACATAC TTAATATTAA AATTTCCCAT TTTTTAAAAA TGGAGAGTCT
 551  GAATTTTATT AGAGCTCACA CACCATATAT TAACATATAC AACTGTGAAC
 601  CAGCTAATCC CTCTGAGAAA AACTCCCCAT CTACCCAATA CTGTTACAGC
 651  ATACAATCTC TGTTCTTGGG CATTTTGTCA GTGATGCTGA TCTTTGCCTT
 701  CTTCCAGGAA CTTGTAATAG CTGGCATCGT TGAGAATGAA TGGAAAAGAA
 751  CGTGCTCCAG ACCCAAATCT AACATAGTTC TCCTGTCAGC ACAAGAAAAA
 801  AAAGAACAGA CTATTGAAAT AAAAGAAGAA GTGGTTGGGC TAACTGAAAC
 851  ATCTTCCCAA CCAAAGAATG AAGAAGACAT TGAAATTATT CCAATCCAAG
 901  AAGAGGAAGA AGAAGAAACA GAGACGAACT TTCCAGAACC TCCCCAAGAT
 951  CAGGAATCCT CACCAATAGA AAATGACAGC TCTCCTTAAG TGATTTCTTC
1001  TGTTTTCTGT TTCCTTTTTT AAACATTAGT GTTCATAGCT TCCAAGAGAC
1051  ATGCTGACTT TCATTTCTTG AGGTACTCTG CACATACGCA CCACATCTCT
```

FIG. 13A

```
1101  ATCTGGCCTT TGCATGGAGT GACCATAGCT CCTTCTCTCT TACATTGAAT
1151  GTAGAGAATG TAGCCATTGT AGCAGCTTGT GTTGTCACGC TTCTTCTTTT
1201  GAGCAACTTT CTTACACTGA AGAAAGGCAG AATGAGTGCT TCAGAATGTG
1251  ATTTCCTACT AACCTGTTCC TTGGATAGGC TTTTTAGTAT AGTATTTTTT
1301  TTTGTCATTT TCTCCATCAG CAACCAGGGA GACTGCACCT GATGGAAAAG
1351  ATATATGACT GCTTCATGAC ATTCCTAAAC TATCTTTTTT TTATTCCACA
1401  TCTACGTTTT TGGTGGAGTC CCTTTTTATC ATCCTTAAAA CAATGATGCA
1451  AAAGGGCTTT AGAGCACAAT GGATCT
```

FIG. 13B

```
   1  CCCAAATGTC TCAGAATGTA TGTCCCAGAA ACCTGTGGCT GCTTCAACCA
  51  TTGACAGTTT TGCTGCTGCT GGCTTCTGCA GACAGTCAAG CTGCAGCTCC
 101  CCCAAAGGCT GTGCTGAAAC TTGAGCCCCC GTGGATCAAC GTGCTCCAGG
 151  AGGACTCTGT GACTCTGACA TGCCAGGGGG CTCGCAGCCC TGAGAGCGAC
 201  TCCATTCAGT GGTTCCACAA TGGGAATCTC ATTCCCACCC ACACGCAGCC
 251  CAGCTACAGG TTCAAGGCCA CAACAATGA CAGCGGGGAG TACACGTGCC
 301  AGACTGGCCA GACCAGCCTC AGCGACCCTG TGCATCTGAC TGTGCTTTCC
 351  GAATGGCTGG TGCTCCAGAC CCCTCACCTG GAGTTCCAGG AGGGAGAAAC
 401  CATCATGCTG AGGTGCCACA GCTGGAAGGA CAAGCCTCTG GTCAAGGTCA
 451  CATTCTTCCA GAATGGAAAA TCCCAGAAAT CTCCCGTTT GGATCCCACC
 501  TTCTCCATCC CACAAGCAAA CCACAGTCAC AGTGGTGATT ACCACTGCAC
 551  AGGAAACATA GGCTACACGC TGTTCTCATC CAAGCCTGTG ACCATCACTG
 601  TCCAAGTGCC CAGCATGGGC AGCTCTTCAC CAATGGGGAT CATTGTGGCT
 651  GTGGTCATTG CGACTGCTGT AGCAGCCATT GTTGCTGCTG TAGTGGCCTT
 701  GATCTACTGC AGGAAAAAGC GGATTTCAGC CAATTCCACT GATCCTGTGA
 751  AGGCTGCCCA ATTTGAGCCA CCTGGACGTC AAATGATTGC CATCAGAAAG
 801  AGACAACTTG AAGAAACCAA CAATGACTAT GAAACAGCTG ACGGCGGCTA
 851  CATGACTCTG AACCCCAGGG CACCTACTGA CGATGATAAA AACATCTACC
 901  TGACTCTTCC TCCCAACGAC CATGTCAACA GTAATAACTA AGAGTAACG
 951  TTATGCCATG TGGTCATACT CTCAGCTTGC TGAGTGGATG ACAAAAAGAG
1001  GGGAATTGTT AAAGGAAAAT TTAAATGGAG ACTGGAAAAA TCCTGAGCAA
1051  ACAAAACCAC CTGGCCCTTA GAAATAGCTT TAACTTTGCT TAAACTACAA
1101  ACACAAGCAA AACTTCACGG GGTCATACTA CATACAAGCA TAAGCAAAAC
1151  TTAACTTGGA TCATTTCTGG TAAATGCTTA TGTTAGAAAT AAGACAACCC
1201  CAGCCAATCA CAAGCAGCCT ACTAACATAT AATTAGGTGA CTAGGGACTT
1251  TCTAAGAAGA TACCTACCCC CAAAAAACAA TTATGTAATT GAAAACCAAC
1301  CGATTGCCTT TATTTTGCTT CCACATTTTC CCAATAAATA CTTGCCTGTG
1351  ACATTTTGCC ACTGGAACAC TAAACTTCAT GAATTGCGCC TCAGATTTTT
1401  CCTTTAACAT CTTTTTTTTT TTTGACAGAG TCTCAATCTG TTACCCAGGC
1451  TGGAGTGCAG TGGTGCTATC TTGGCTCACT GCAAACCCGC CTCCCAGGTT
1501  TAAGCGATTC TCATGCCTCA GCCTCCCAGT AGCTGGGATT AGAGGCATGT
1551  GCCATCATAC CCAGCTAATT TTTGTATTTT TTATTTTTTT TTTTTAGTAG
1601  AGACAGGGTT TCGCAATGTT GGCCAGGCCG ATCTCGAACT TCTGGCCTCT
1651  AGCGATCTGC CCGCCTCGGC CTCCCAAAGT GCTGGGATGA CCAGCATCAG
```

FIG. 14A

```
1701  CCCCAATGTC CAGCCTCTTT AACATCTTCT TTCCTATGCC CTCTCTGTGG
1751  ATCCCTACTG CTGGTTTCTG CCTTCTCCAT GCTGAGAACA AAATCACCTA
1801  TTCACTGCTT ATGCAGTCGG AAGCTCCAGA AGAACAAAGA GCCCAATTAC
1851  CAGAACCACA TTAAGTCTCC ATTGTTTTGC CTTGGGATTT GAGAAGAGAA
1901  TTAGAGAGGT GAGGATCTGG TATTTCCTGG ACTAAATTCC CCTTGGGGAA
1951  GACGAAGGGA TGCTGCAGTT CCAAAAGAGA AGGACTCTTC CAGAGTCATC
2001  TACCTGAGTC CCAAAGCTCC CTGTCCTGAA AGCCACAGAC AATATGGTCC
2051  CAAATGACTG ACTGCACCTT CTGTGCCTCA GCCGTTCTTG ACATCAAGAA
2101  TCTTCTGTTC CACATCCACA CAGCCAATAC AATTAGTCAA ACCACTGTTA
2151  TTAACAGATG TAGCAACATG AGAAACGCTT ATGTTACAGG TTACATGAGA
2201  GCAATCATGT AAGTCTATAT GACTTCAGAA ATGTTAAAAT AGACTAACCT
2251  CTAACAACAA ATTAAAAGTG ATTGTTTCAA GGTGAAAAAA
```

FIG. 14B

```
   1  GCTGTGACTG CTGTGCTCTG GGCGCCACTC GCTCCAGGGA GTGATGGGAA
  51  TCCTGTCATT CTTACCTGTC CTTGCCACTG AGAGTGACTG GGCTGACTGC
 101  AAGTCCCCCC AGCCTTGGGG TCATATGCTT CTGTGGACAG CTGTGCTATC
 151  CCTGGCTCCT GTTGCTGGGA CACCTGCAGC TCCCCCAAAG GCTGTGCTGA
 201  AACTCGAGCC CCAGTGGATC AACGTGCTCC AGGAGGACTC TGTGACTCTG
 251  ACATGCCGGG GGACTCACAG CCCTGAGAGC GACTCCATTC AGTGGTTCCA
 301  CAATGGGAAT CTCATTCCCA CCCACACGCA GCCCAGCTAC AGGTTCAAGG
 351  CCAACAACAA TGACAGCGGG GAGTACACGT GCCAGACTGG CCAGACCAGC
 401  CTCAGCGACC CTGTGCATCT GACTGTGCTT TCTGGTCAGT GGAGGAAGGC
 451  CCCAGGGTGG ACCTGGGAGG CCAGGACGG ATGAAATCTG CTTTCAGGCA
 501  GAGGTTTGCA GGAAAGGGGG GTGGCCTGCT TACTGGGAAG TATCGCTGTG
 551  AGTTGCCTCA GCACATATCA GTGGTTGTTT TTGCCTCAGT TCTGATTGAA
 601  CAGAAGAAGG TTTCAAGGCC AAAAACAGGC AGCCAAGTGT GAGAGAAGCA
 651  GAAGGAAATC CCTACTGCAT AAAACCCATT TCCATTTTAA TGGCAGAATT
 701  GAAAAGCACA GACCACAACT GAATCCTAGC CCTGGAAATG ACTCACTATA
 751  CAACATGATG AATTCATTTA ACCCTTGAGT TTCCATTTCT TCACCTGCTC
 801  CGTGGGGCAC TAACGCCTCC CTCAGAGGCT TCTGGTGAGA ATCAGTGTTT
 851  CCCTGCCCCC GCCCCGCCCT CCATGCCCCT TCTCCACGTT CTCACTGTGC
 901  TAGGTGCTCT TCTCTGTCTT TCTCTTCCAC CAGCCTGTGG GAAACCTGAG
 951  ATGAAAGTCG TGTCTTACCC ATCTTTGTAT TTCCAGCATC TGAAACTGGG
1001  CAGAGCTTAA TAAATATTTT GCTGGAGAGG TTGATGATCT TACAAAGCTC
1051  CCATTGAAAG GTGGCTCTCT GTAAAGCAAA GTTACAATGA GATTGTGATG
1101  AACATTGTCC TTGTGGCTTT TCACTTAGTC CCCTCCCTTC ACCTGAAGAG
1151  CAAATTTTCC TCAAAAGTAC ACAGCAAACG AATGACCCAC TGGTGACACT
1201  GTTGCCTTTA GACCCTGCTG GAAAGAAGCT CCACATTTAT TAACATTCCC
1251  GAAGTAAATT TATCAGGTAG CATTCATCAG GTAACATTTG TTGCACATTC
1301  ATGACTTTTC TACTGTCCAC AAAGGCATAT GTCCTTATCA TATGCGGACT
1351  CCTCGGTCAC ACTGGATTCT TCCTTCCCTC CTCGACATGG AAGAGATGGC
1401  ATCTTAGGGT CTCTTGTGTT CTTCCTGCAG AGGCCTGTCG GGCAGGAAAA
1451  GGCTGCAGCT GCCTTCCTGG GAGAAGGAGG AGATGAGTGT ATCCTGAACA
1501  CCTATTATGT GCTAGGGGCT ATTGTAGATA CATGACACTA TCATGCTCAT
1551  TTTCACGAAT GAGGAAACTG AGGCTCAGAA GACTTAAATT ATTTGCCCAA
1601  GAGTTATAAA TGACAGAGCC AGCATTAGAG TCCAGGACTG TCTGATTTCA
1651  GACCTAAGCT GTTCCCTCTG CACATCGTGT CCCACCAGTA AGGAAGATCT
```

FIG. 15A

```
1701  GGGTCTCAGA GCTGAGCCAA GACCTCCCGG GTCCTCTGCG GTTTTTTGTG
1751  TCTTTCAGAG TGGCTGGTGC TCCAGACCCC TCACCTGGAG TTCCAGGAGG
1801  GAGAAACCAT CGTGCTGAGG TGCCACAGCT GGAAGGACAA GCCTCTGGTC
1851  AAGGTCACAT TCTTCCAGAA TGGAAAATCC AAGAAATTTT CCCGTTCGGA
1901  TCCCAACTTC TCCATCCCAC AAGCAAACCA CAGTCACAGT GGTGATTACC
1951  ACTGCACAGG AAACATAGGC TACACGCTGT ACTCATCCAA GCCTGTGACC
2001  ATCACTGTCC AAGCTCCCAG CTCTTCACCG ATGGGGATCA TTGTGGCTGT
2051  GGTCACTGGG ATTGCTGTAG CGGCCATTGT TGCTGCTGTA GTGGCCTTGA
2101  TCTACTGCAG GAAAAAGCGG ATTTCAGGTT TGTAGCTCCT CCCGGTCCCT
2151  TTTGTTATCA GTTTCCACTT T
```

FIG. 15B

```
  1  GCCTCGCTCG GGCGCCCAGT GGTCCTGCCG CCTGGTCTCA CCTCGCCATG
 51  GTTCGTCTGC CTCTGCAGTG CGTCCTCTGG GGCTGCTTGC TGACCGCTGT
101  CCATCCAGAA CCACCCACTG CATGCAGAGA AAAACAGTAC CTAATAAACA
151  GTCAGTGCTG TTCTTTGTGC CAGCCAGGAC AGAAACTGGT GAGTGACTGC
201  ACAGAGTTCA CTGAAACGGA ATGCCTTCCT TGCGGTGAAA GCGAATTCCT
251  AGACACCTGG AACAGAGAGA CACACTGCCA CCAGCACAAA TACTGCGACC
301  CCAACCTAGG GCTTCGGGTC CAGCAGAAGG GCACCTCAGA AACAGACACC
351  ATCTGCACCT GTGAAGAAGG CTGGCACTGT ACGAGTGAGG CCTGTGAGAG
401  CTGTGTCCTG CACCGCTCAT GCTCGCCCGG CTTTGGGGTC AAGCAGATTG
451  CTACAGGGGT TTCTGATACC ATCTGCGAGC CCTGCCCAGT CGGCTTCTTC
501  TCCAATGTGT CATCTGCTTT CGAAAAATGT CACCCTTGGA CAAGCTGTGA
551  GACCAAAGAC CTGGTTGTGC AACAGGCAGC ACAAACAAGA CTGATGTTGT
601  CTGTGGTCCC CAGGATCGGC TGAGAGCCCT GGTGGTGATC CCCATCATCT
651  TCGGGATCCT GTTTGCCATC CTCTTGGTGC TGGTCTTTAT CAAAAAGGTG
701  GCCAAGAAGC CAACCAATAA GGCCCCCCAC CCCAAGCAGG AACCCCAGGA
751  GATCAATTTT CCCGACGATC TTCCTGGCTC CAACACTGCT GCTCCAGTGC
801  AGGAGACTTT ACATGGATGC CAACCGGTCA CCCAGGAGGA TGGCAAAGAG
851  AGTCGCATCT CAGTGCAGGA GAGACAGTGA GGCTGCACCC ACCCAGGAGT
901  GTGGCCACGT GGGCAAACAG GCAGTTGGCC AGAGAGCCTG GTGCTGCTGC
951  TGCAGGGGTG CAGGCAGAAG CGGGGAGCTA TGCCCAGTCA GTGCCAGCCC
     CTC
```

FIG. 16

CD40 CODING SEQUENCES

This application is a divisional of co-pending U.S. patent application Ser. No. 07/983,647, filed Dec. 1, 1992, which is a continuation-in-part of U.S. patent application Ser. No. 553,759, filed Jul. 13, 1990, now abandoned; which is a continuation-in-in-part of U.S. Ser. No. 07/498,809 filed Mar. 23, 1990, now abandoned; which is a continuation-in-part of U.S. Ser. No. 379,076, filed Jul. 13, 1989, now abandoned; which is a continuation-in-part of U.S. Ser. No. 160,416, filed Feb. 25, 1988, now abandoned. Each of these predecessor applications and all references cited herein are incorporated by reference in their entirety.

BACKGROUND

A basic tool in the field of recombinant genetics is the conversion of poly(A)$^+$ mRNA to double-stranded (ds) cDNA, which then can be inserted into a cloning vector and expressed in an appropriate host cell. Molecular cloning methods for ds cDNA have been reviewed, for example, by Williams, "The Preparation and Screening of a cDNA Clone Bank," in Williamson, ed., *Genetic Engineering*, Vol. 1, p. 2, Academic Press, New York (1981); Maniatis, "Recombinant DNA", in Prescott, ed., *Cell Biology*, Academic Press, New York (1980); and Efstratiadis et al., "Cloning of Double-Stranded DNA," in Stelo et al., *Genetic Engineering*, Vol. 1, p. 15, Plenum Press, New York (1979).

A substantial number of variables affect the successful cloning of a particular gene and cDNA cloning strategy thus must be chosen with care. A method common to many cDNA cloning strategies involves the construction of a "cDNA library" which is a collection of cDNA clones derived from the total poly(A)$^+$ mRNA derived from a cell of the organism of interest.

A mammalian cell may contain up to 30,000 different mRNA sequences, and the number of clones required to obtain low-abundance mRNAs, for example, may be much greater. Methods of constructing genomic eukaryotic DNA libraries in different expression vectors, including bacteriophage lambda, cosmids, and viral vectors, are known. Some commonly used methods are described, for example, in Maniatis et al., *Molecular Cloning: A Laboratory Manual*, Cold Spring Harbor Laboratory, publisher, Cold Spring Harbor, N.Y. (1982).

Once a genomic cDNA library has been constructed, it is necessary to isolate from the thousands of host cells the cell containing the particular human gene of interest. Many different methods of isolating target genes from cDNA libraries have been utilized, with varying success. These include, for example, the use of nucleic acid probes, which are labeled mRNA fragments having nucleic acid sequences complementary to the DNA sequence of the target gene. When this method is applied to cDNA clones of abundant mRNAs in transformed bacterial hosts, colonies hybridizing strongly to the probe are likely to contain the target DNA sequences. The identity of the clone then may be proven, for example, by in situ hybridization/selection (Goldberg et al., *Methods Enzymol.*, 68:206 (1979)) hybrid-arrested translation (Paterson et al., *Proceedings of the National Academy of Sciences*, 74:4370 (1977)), or direct DNA sequencing (Maxam and Gilbert, *Proceedings of the National Academy of Sciences*, 74:560 (1977); Maat and Smith, *Nucleic Acids Res.*, 5:4537 (1978)).

Such methods, however, have major drawbacks when the object is to clone mRNAs of relatively low abundance from cDNA libraries. For example, using direct in situ colony hybridization, it is very difficult to detect clones containing cDNA complementary to mRNA species present in the initial library population at less than one part in 200. As a result, various methods for enriching mRNA in the total population (e.g. size fractionation, use of synthetic oligodeoxynucleotides, differential hybridization, or immunopurification) have been developed and are often used when low abundance mRNAs are cloned. Such methods are described, for example, in Maniatis et al., *Molecular Cloning: A Laboratory Manual*, supra.

Many functional eukaryotic proteins initially exist in the form of precursor molecules which contain leader or signal sequences at their N-terminal ends. These leader sequences bind to the cell membrane and draw the remainder of the protein through the lipid bilayer, after which the signal sequence is cleaved from the protein by a signal peptidase enzyme. The protein thus functions only after secretion from the cells (for example, insulin, serum albumin, antibodies, and digestive tract enzymes), or after the proteins have been anchored to the outer surface of a cell membrane (for example, histocompatibility antigens).

The cell surface antigens characteristic of mammalian T lymphocytes are additional examples of proteins that anchor to the cell surface. In mammals, certain cells derived from bone marrow mature into lymphocytes, which are present in the lymphoid organs, including the thymus, spleen, lymph nodes, and lymphoid aggregates, and also circulate actively through the blood and lymph systems. Mature lymphocyte cells may be divided into two populations: thymus-dependent (T) lymphocytes and thymus-independent (B) lymphocytes. T lymphocytes migrate to the interior of the thymus, where they undergo differentiative proliferation. During their differentiation process, they express characteristic cell surface membrane alloantigens, including Thy-1, TLA, gv-1, Ly-1, Ly-2, Ly-3, and Ly-5. As they mature, T lymphocytes lose the TLA antigens and some of the Thy-1 antigens, and gain histocompatibility antigens, acquiring the membrane conformation typical of the recirculating T lymphocytes. This is described, for example, by Mota, "Activity of Immune Cells," in Bier et al., eds., *Fundamentals of Immunology*, 2d Ed., Springer-Verlag, Berlin, pp. 35–62 (1986).

T lymphocytes are involved indirectly in the formation of antibodies and their activities thus have required complex analysis of cell function, rather than simple antibody titer measurement. Partly due to this, their importance in development of immunologic competence was not recognized until relatively recently. Mature T lymphocytes synthesize and express an unique pattern of surface glycoprotein antigens which serve as markers for identification of different T lymphocyte subpopulations, including T helper cells, T suppressor cells, and T cytotoxic cells. Each of these subpopulations plays a very important role in regulating the immune system. (Mota, supra).

In humans, the functional and phenotypic heterogeneity of T lymphocytes is well accepted. Two major subpopulations are known: effector T cells mediating cellular immunity; and regulator T cells containing helper and suppressor T lymphocytes. These two subpopulations have been defined with heteroantisera, autoantibodies, and monoclonal antibodies directed at cell surface antigens. For example, earlier in their development, human lymphoid cells in the thymus express an antigen designated T11 which reacts strongly to a monoclonal antibody designated Cluster of Differentiation 2 (CD2), and react slightly with monoclonal antibody CD5 to cell surface antigen T1. During maturation, these cells lose T11 (CD2) and acquire three new antigens defined by monoclonal antibodies CD4, CD8, and CD1. With further maturation, the thymocytes cease to express cell surface antigens reactive with monoclonal antibody CD1, express the T3 antigen reactive with monoclonal antibody CD3, and then segregate into two subpopulations which express either T4 (CD4) or T8 (CD8) antigen. Immunologic competence is acquired at this stage, but is not completely developed until thymic lymphocytes migrate outside the thymus. (Mota, supra.) In contrast with the majority of thymocytes, circulating T lymphocytes express the T1 (CD5) and T3 (CD3) antigens. The T4 (CD4) antigen is present on approximately 55–65% of peripheral T lymphocytes, whereas the T8 (CD8) antigen is expressed on 20–30%. These two subpopulations correspond to helper and to suppressor and cytotoxic T cells, respectively.

In addition to providing a convenient means of distinguishing T lymphocyte subpopulations, these cell surface antigens are important for mature T cell activation and effector function. T cell activation involves a complex series of cell surface interactions between the T cell and the target cell or stimulator cell in addition to binding of the T cell receptor to its specific antigen.

For example, CD2, the human T cell erythrocyte receptor, allows thymocytes and T-lymphocytes to adhere to target cells (e.g., erythrocytes) and to thymic epithelium. This occurs via a specific molecular ligand for CD2, designated LFA-3, in humans, which is a widely distributed surface antigen. This phenomenon has long been employed to detect, assay and purify human cells producing antibodies to sheep erythrocytes and serves as the basis for the E-rosette test, first described by Zaalberg, *Nature* 202:1231 (1964). CD2LFA-3 interactions also have been shown to mediate cytolytic target conjugation (Shaw et al., *Nature* 323:262–264 (1986), and the mixed lymphocyte reaction (Martin et al., *J. Immunol.* 131:180–185 (1983). Anti-CD2 monoclonal antibodies can directly activate peripheral T-lymphocytes via an antigen-independent pathway (Meuer et al., *Cell* 36:897–906 (1984)), indicating an even wider immunoregulatory role for CD2.

Recognition that T lymphocytes are the main effectors of cell-mediated immunity and also are involved as helper or suppressor cells in modulating the immune response has resulted in a significant contribution to the increasing practical application of clinical immunology to medicine. The scope of this application includes defense against infections, prevention of diseases by immunization, organ transplantation, blood banking, and treatment of deficiencies of the immune system and a variety of disorders that are mediated by immunologic mechanisms. Moreover, immunologic techniques frequently are used in the clinical laboratory, as in the measurement of hormones and drugs. Clinical immunology is described, for example, in Weir, ed., *Handbook of Experimental Immunology in Four Volumes: Volume 4: Applications of Immunological Methods in Biomedical Sciences,* 4th Ed., Blackwell Scientific Publications, Oxford (1986); Boguslaski et al., eds., *Clinical Immunochemistry: Principles of Methods and Applications,* Little, Brown & Co., Boston (1984); Holborow et al., eds., *Immunology in Medicine: A Comprehensive Guide to Clinical Immunology,* 2d Ed., Grune & Stratton, London (1983); and Petersdorf et al., eds., *Harrison's Principles of Internal Medicine,* 10th ed., McGraw-Hill, New York, publisher, pp. 344–391 (1983). Clearly, a more thorough understanding of the proteins which mediate the immune system would be of significant value in clinical immunology.

Use of mammalian expression libraries to isolate cDNAs encoding mammalian proteins such as those described above would offer several advantages. For example, the protein expressed in a mammalian host cell should be functional and should undergo any normal posttranslational modification. A protein ordinarily transported through the intracellular membrane system to the cell surface should undergo the complete transport process. A mammalian expression system also would allow the study of intracellular transport mechanisms and of the mechanism that insert and anchor cell surface proteins to membranes.

One common mammalian host cell, called a "COS" cell, is formed by infecting monkey kidney cells with a mutant viral vector, designated simian virus strain 40 (SV40), which has functional early and late genes, but lacks a functional origin of replication. In COS cells, any foreign DNA cloned on a vector containing the SV40 origin of replication will replicate because SV40 T antigen is present in COS cells. The foreign DNA will replicate transiently, independently of the cellular DNA.

With the exception of some recent lymphokine cDNAs isolated by expression in COS cells (Wong, G. G., et al., *Science* 228:810–815 (1985); Lee, F. et al., *Proceedings of the National Academy of Sciences, USA* 83:2061–2065 (1986); Yokota, T., et al., *Proceedings of the National Academy of Sciences, USA* 83:5894–5898 (1986); Yang, Y., et al., *Cell* 47:3–10 (1986)), however, few cDNAs in general are isolated from mammalian expression libraries. There appear to be two principal reasons for this: First, the existing technology (Okayama, H. et al., *Mol. Cell. Biol.* 2:161–170 (1982)) for construction of large plasmid libraries is difficult to master, and library size rarely approaches that accessible by phage cloning techniques. (Huynh, T. et al., *In: DNA Cloning Vol. I, A Practical Approach,* Glover, D. M. (ed.), IRL Press, Oxford (1985), pp. 49–78). Second, the existing vectors are, with one exception (Wong, G. G., et al., *Science* 228:810–815 (1985)), poorly adapted for high level expression, particularly in COS cells. The reported successes with lymphokine cDNAs do not imply a general fitness of the methods used, since these cDNAs are particularly easy to isolate from expression libraries. Lymphokine bioassays are very sensitive ((Wong, G. G., et al., *Science* 228:810–815 (1985); Lee, F. et al., *Proceedings of the National Academy of Sciences, USA* 83:2061–2065 (1986); Yokota, T. et al., *Proceedings of the National Academy of Sciences, USA* 83:5894–5898 (1986); Yang, Y. et al., *Cell* 47:3–10 (1986)) and the mRNAs are typically both abundant and short (Wong, G. G. et al., *Science* 228:810–815 (1985); Lee, F., et al., *Proceedings of the National Academy of Sciences, USA* 83:2061–2065 (1986); Yokota, T., et al., *Proceedings of the National Academy of Sciences, USA* 83:5894–5898 (1986); Yang, Y., et al., *Cell* 47:3–10 (1986)).

Thus, expression in mammalian hosts previously has been most frequently employed solely as a means of verifying the identity of the protein encoded by a gene isolated by more traditional cloning methods. For example, Stuve et al., *J. Virol.* 61(2):327–335 (1987), cloned the gene for glycoprotein gB2 of herpes simplex type II strain 333 by plaque hybridization of M13-based recombinant phage vectors used to transform competent *E. coli* JM101. The identity of the protein encoded by the clone thus isolated was verified by transfection of mammalian COS and Chinese hamster ovary (CHO) cells. Expression was demonstrated by immunofluorescence and radioimmunoprecipitation.

Oshima et al. used plaque hybridization to screen a phage lambda gt11 cDNA library for the gene encoding human placental beta-glucuronidase. Oshima et al., *Proceedings of the National Academy of Sciences, U.S.A.* 84:685–689 (1987). The identity of isolated cDNA clones was verified by immunoprecipitation of the protein expressed by COS-7 cells transfected with cloned inserts using the SV40 late promoter.

Transient expression in mammalian cells has been employed as a means of confirming the identity of genes previously isolated by other screening methods. Gerald et al., *Journal of General Virology* 67:2695–2703(1986). Mackenzie, *Journal of Biological Chemistry* 261:14112–14117 (1986); Seif et al., *Gene* 43:1111–1121 (1986); Orkin et al., *Molecular and Cellular Biology* 5(4):762–767 (1985). These methods often are inefficient and tedious and require multiple rounds of screening to identify full-length or overlapping clones. Prior screening methods based upon expression of fusion proteins are inefficient and require large quantities of monoclonal antibodies. Such drawbacks are compounded by use of inefficient expression vectors, which result in protein expression levels that are inadequate to enable efficient selection.

SUMMARY OF THE INVENTION

The present invention relates to a powerful new method for cloning cDNA encoding cell surface antigens, to a method of constructing cDNA libraries, to high efficiency expression vectors particularly suited for high level expression in eukaryotic host cells, and to the isolated nucleotide sequences and their encoded products.

The highly efficient cloning technique of the present invention is based upon transient expression of antigen in eukaryotic cells and physical selection of cells expressing the antigen by adhesion to an antibody-coated substrate, such as a culture dish. The methods of the present invention are useful for the isolation and molecular cloning of any protein which can be expressed and transported to the cell surface membrane of a eukaryotic cell.

The method for cloning cDNA encoding a cell surface antigen of the present invention comprises preparing a cDNA library; introducing this cDNA library into eukaryotic mammalian cells, preferably tissue culture cells; culturing these cells under conditions allowing expression of the cell surface antigen; exposing the cells to a first antibody or antibodies directed against the cell surface antigen, thereby allowing the formation of a cell surface antigen-first antibody complex; subsequently exposing the cells to a substrate coated with a second antibody directed against the first antibody, thereby causing cells expressing the cell surface antigen to adhere to the substrate via the formation of a cell surface antigen-first antibody-second antibody complex; and separating adherent from non-adherent cells.

By means of the cloning method of the present invention, isolation and molecular cloning of genes encoding such cell surface antigens as the following have been accomplished: the CD1a, CD1b, CD1c, CD2, CD6, CD7, CD13, CD14, CD16, CD19, CD20, CD22, CD26, CD27, CD28, CD31, CDw32a, CDw32b, CD33, CD34, CD36, CD37, CD38, CD39, CD40, CD43, CD44, CD53, ICAM, LFA-3, FcRIa, FcRIb, TLiSa, and Leu8 antigens. The nucleotide sequences of genes cloned by the method of the present invention have been determined and the amino acid sequences of the encoded proteins have been identified. A cloned gene, such as that encoding CD1a, CD1b, CD1c, CD2, CD6, CD7, CD13, CD14, CD16, CD19, CD20, CD22, CD26, CD27, CD28, CD31, CDw32a, CDw32b, CD33, CD34, CD36, CD37, CD38, CD39, CD40, CD43, CD44, CD53, ICAM, LFA-3, FcRIa, FcRIb, TLiSa, and Leu8, is also the subject of the present invention.

Once the gene encoding an antigen has been cloned according to the method of the present invention, that gene can be expressed in a prokaryotic or a eukaryotic host cell to produce the encoded protein or portion thereof in substantially pure form such as it does not exist in nature. Another aspect of the present invention relates to substantially pure cell surface antigens, particularly: CD1a, CD1b, CD1c, CD2, CD6, CD7, CD13, CD14, CD16, CD19, CD20, CD22, CD26, CD27, CD28, CD31, CDw32a, CDw32b, CD33, CD34, CD36, CD37, CD38, CD39, CD40, CD43, CD44, CD53, ICAM, LFA-3, FcRIa, FcRIb, TLiSa, and Leu8 antigens and their functional analogues and equivalents. The primary amino acid sequences of the CD1a, CD1b, CD2, CD7, CD14, CD16, CD19, CD20, CD22, CD27, CD28, CDw32a, CDw32b, CD33, CD34, CD40, CD44, CD53, ICAM, LFA-3, FcRIa, FcRIb, TLiSa and Leu8 antigens have been determined. The invention thus also relates to the amino acid sequences of those antigens and their functional equivalents and to the nucleotide sequences encoding those antigens.

This invention also relates to high efficiency cDNA expression vectors which allow the generation of very large mammalian expression libraries and yield large amounts of protein in mammalian host cells, resulting in efficient selection. In a particular embodiment of this invention, a cDNA expression vector comprises a suppressor tRNA gene; an SV40 origin; a synthetic transcription unit, comprising a chimeric promoter composed of human cytomegalovirus AD169 immediate early enhancer sequence fused to the HIV LTR −60 to +80 sequences, inserted between the suppressor tRNA gene and the SV40 origin; a polylinker comprising two BstXI sites separated by a replaceable DNA sequence and flanked by XbaI sites; and an SV40 small t antigen splice and early region polyadenylation signals.

A further aspect of the present invention comprises a synthetic transcription unit for use in a cDNA expression vector, comprising a chimeric promoter composed of human cytomegalovirus AD169 immediate early enhancer sequences fused to HIV LTR −60 to +80 sequences. The small size and particular arrangement of the sequences of the cDNA expression vector of the present invention allow highly efficient replication in host mammalian tissue culture cells, such as COS cells. Moreover, this vector employs a polylinker containing two inverted BstXI sites separated by a short replaceable DNA segment, which allows the use of very efficient oligonucleotide-based cDNA insertion strategy.

In another aspect, the present invention comprises a vector comprising two identical BstXI sites in inverted orientation each with respect to the other, which BstXI sites are separated by a short replaceable DNA fragment. Another aspect of the invention is a polylinker as described above.

A further aspect of the invention relates to an oligonucleotide-based cDNA insertion method, comprising ligating synthetic DNA oligonucleotides to the cDNA segment desired to be inserted into a vector, the synthetic DNA oligonucleotides giving the same terminal sequences as those of the short replaceable DNA fragment of the polylinker of the invention, and inserting the resulting cDNA segment plus synthetic DNA oligonucleotide terminal sequences into the polylinker of the vector, from which the short replaceable DNA fragment previously has been removed.

In preparing cDNA libraries according to the present invention, it has been discovered that many tumors are heavily infiltrated by macrophages and lymphocytes, and thus may be employed as a source of macrophage or lymphocyte transcripts to good effect, instead of tumor cell lines commonly used. In another aspect, then, the present invention relates to the use of tumor cells, particularly human tumor cells, to prepare cDNA libraries for use according to the methods of the present invention.

Another advantage of the powerful selection system of the present invention is that directional insertion of the cDNA is not necessary. The method of the present invention results in library construction efficiencies which are on a par with those described for phage vectors such as lambda gt10 and lambda gt11, with the additional advantage that clones generated according to the methods of the present invention are easier to manipulate.

The immunoselection technique of the present invention allows efficient use of antibodies, which may be monoclonal or polyclonal, in relatively small absolute amounts. The method of the present invention also is quite rapid. Generally, three or fewer cycles of immunoselection and rescue are required to isolate a target cDNA clone. Thus, the method of the present invention also results in the efficient use of labor and materials when cloning genes encoding cell surface antigens. As described above, this method has been employed to successfully clone genes encoding cell surface antigens associated with mammalian T lymphocytes (e.g. antigens CD1a, CD1b, CD1c, CD2, CD6, CD7, CD13, CD14, CD16, CD19, CD20, CD22, CD26, CD27, CD28, CD31, CDw32a, CDw32b, CD33, CD34, CD36, CD37, CD38, CD39, CD40, CD43, CD44, CD53, ICAM, LFA-3, FcRIa, FcRIb, TLiSa, and Leu8).

The purified genes and proteins of the present invention are useful for immunodiagnostic and immunotherapeutic applications, including the diagnosis and treatment of immune-mediated infections, diseases, and disorders in animals, including humans. They can also be used to identify, isolate and purify other antibodies and antigens. Such diagnostic and therapeutic uses comprise yet another aspect of the present invention. Moreover, the substantially pure proteins of the present invention may be prepared as medicaments or pharmaceutical compositions for therapeutic administration. The present invention further relates to such medicaments and compositions.

BRIEF DESCRIPTION OF THE DRAWINGS

FIGS. 1A–1B.
Nucleotide sequence of expression vector piH3
Nucleotides 1–589 are derived from pMB1 origin (pBR322 ori); nucleotides 590–597 are derived from the SacII linker (ACCGCGT); nucleotides 598–799 are derived from the synthetic tyrosine suppressor tRNA gene (supF gene); nucleotides 800–947 are derived from a remnant of the ASV LTR fragment (PvuII to MluI); nucleotides 948–1500 are derived from the human cytomegalovirus AD169 enhancer; nucleotides 1501–1650 are derived from HIV TATA and tat-responsive elements; nucleotides 1651–1716 are derived from the piLNXAN polylinker (HindIII to Xba); nucleotides 1717–2569 are derived from pSV to splice and poly-Addition signals; nucleotides 2570–2917 are derived from the SV40 origin of replication (PvuII to (HindIII); and nucleotides 2918–2922 are derived from piVX, remnant of R1 site from polylinker.

FIGS. 2A–2B.
Nucleotide sequence of the CD2cDNA insert
Nucleotide numbering is given in parentheses at right, amino acid numbering, left. Locations of the potential sites for addition of asparagine-linked carbohydrate (CHO) are shown, as well as the predicted transmembrane (TM) sequence. The amino acid sequence is numbered from the projected cleavage site of the secretory signal sequence.

FIGS. 4A–4B.
Nucleotide sequence and corresponding amino acid sequence of the LFA-3 antigen
WOP cells transfected with a clone encoding the LFA-3 antigen were detected by indirect immunofluorescence, amplified and sequenced. FIG. 4A shows the 874 base pair insert containing an open reading frame of 237 residues originating at a methionine codon, and terminating in a series of hydrophobic residues. Hydrophobic and hydrophilic regions within this open reading frame are shown in FIG. 4B.

FIGS. 6A–6D.
Nucleotide sequence of the piH3M vector
There are 7 segments. Residues 1–587 are from the pBR322 origin of replication, 588–1182 from the M13 origin, 1183–1384 from the supF gene, 1385–2238 are from the chimeric cytomegalovirus/human immunodeficiency virus promoter, 2239–2647 are from the replaceable fragment, 2648–3547 from plasmid pSV2 (splice and polyadenylation signals), and 3548–3900 from the SV40 virus origin.

FIGS. 7A–7B.
Nucleotide sequence of the CD28 cDNA
Nucleotide numbering is given in parentheses at right, amino acid numbering, center and left. Location of the potential sites for addition of asparagine-linked carbohydrate (CHO) are shown, as well as the predicted transmembrane (TM) sequence. The amino acid sequence is numbered from the projected cleavage site of the secretory signal sequence.

FIGS. 8A–8B.
Nucleotide sequence of the CD7 cDNA insert
Nucleotide numbering is given in parentheses at right. Splice donor and acceptor sites indicated by (/). The location of the potential sites for addition of asparagine-linked carbohydrate (CHO) are shown, the potential fatty acid esterification site is denoted (*), and the predicted transmembrane domain (TM) is underlined. Nucleotide sequences potentially involved in hairpin formation are denoted by (.). The presumed polyadenylation signal is underlined.

FIGS. 9A–9B.
Nucleotide sequence of the CDw32 cDNA
Nucleotide number is given in the parenthesis at right, amino acid numbering, center and left. Locations of the potential sites for addition of asparagine-linked carbohydrate (CHO) are shown, as well as the predicted transmembrane (TM) sequence. The amino acid sequence is numbered from the projected cleavage site of the secretory signal sequence. Cysteine residues are underscored with asterisks.

Sequence of the CD20.4 cDNA

Figure 3:
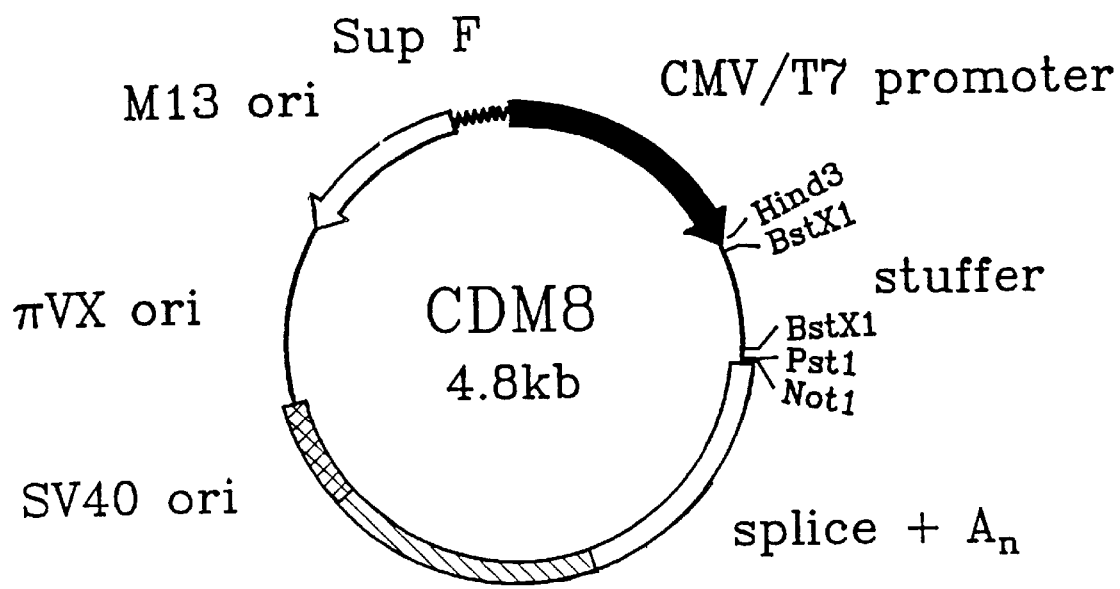
FIG. 3.
Restriction map of the CDM8 expression vector
The CDM8 vector includes a deleted version of a mutant polyoma virus early region selected for high efficiency expression in both murine and monkey cells. Substantially all of the human immunodeficiency promoter region has been replaced with the cognate sequences of the human cytomegalovirus immediate early promoter, and by inclusion of a bacteriophage T7 promoter between the eukaryotic promoter and the site of cDNA insertion. Arrows indicate the direction of transcription.

The sites of potential N-linked glycosylation are denoted by the symbol —CHO—; the hydrophobic regions are underscored. The site of the poly(A)$^+$ tail in clone CD20.6 is denoted by an asterisk.

FIG. 10C.

Hydrophobicity profile of the amino acid sequence in A.

FIGS. 11A–11C.

Sequence of ICAM-1

Complete nucleotide sequence of ICAM-1 cDNA insert and predicted protein sequence. Nucleotide numbering is at left, amino acid numbering, center. The RGE motif at position 128 is underlined, the potential N-linked glycosylation sites are indicated by —CHO— and the transmembrane domain by -TM-. The amino acid sequence is numbered from the projected cleavage site of the signal peptide. Sequencing was by dideoxy-chain termination (Sanger, F., et al., *Proc. Natl. Acad. Sci. USA* 74:5463–5467 (1977)), using a combination of subclones, and specific oligonucleotides.

FIGS. 12A–12B.

Nucleotide sequence of CD19

FIGS. 13A–13B.

Nucleotide sequence of CD20

FIGS. 14A–14B.

Nucleotide sequence of CDw32a

FIGS. 15A–15B.

Nucleotide sequence of CDw32b

FIG. 16.

Nucleotide sequence of CD40

DETAILED DESCRIPTION OF THE INVENTION

This invention relates to a novel method for cloning cDNA encoding a cell surface antigen and to a method of constructing cDNA libraries. It also relates to particular cDNA expression vectors and components thereof, nucleotide sequences or genes isolated by the method, substantially pure cell surface antigens encoded by the cDNA segments, and methods of using the isolated nucleotide sequences and encoded products.

In the following description, reference will be made to various methodologies known to those of skill in the art of recombinant genetics. Publications and other materials setting forth such known methodologies to which reference is made are incorporated herein by reference in their entireties. Standard reference works setting forth the general principles of recombinant DNA technology include Darnell, J. E. et al., *Molecular Cell Biology*, Scientific American Books, Inc., publisher, New York, N.Y. (1986); Lewin, B. M., *Genes II*, John Wiley & Sons, publisher, New York, N.Y. (1985); Old, R. W. et al., *Principles of Gene Manipulation: An Introduction to Genetic Engineering*, 2d edition, University of California Press, Berkeley, Calif. (1981); and Maniatis, T. et al., *Molecular Cloning: A Laboratory Manual*, Cold Spring Harbor, N.Y. (1982).

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which together comprise the entire genome of an organism. Such a cDNA library may be prepared by art-recognized methods described, for example, in Maniatis et al., *Molecular Cloning: A Laboratory Manual,* supra. Generally, RNA is first isolated from the cells of an organism from whose genome it is desired to clone a particular gene. Preferred for the purposes of the present invention are mammalian, and particularly human, cell lines. More preferred are the human tumor cell line HPB-ALL and the human lymphoblastoid cell line JY. Alternatively, RNA can be isolated from a tumor cell, derived from an animal tumor, and preferably from a human tumor. Thus, a library may be prepared from, for example, a human adrenal tumor, but any tumor may be used.

The immunoselection cloning method of the present invention comprises the preparation of a cDNA library by extracting total RNA including a particular gene from a cell, synthesizing a series of complementary double-stranded cDNA fragments from the RNA and introducing these cDNA fragments into mammalian cells in tissue culture. The mammalian cells are maintained under conditions which allow them to express the protein (i.e. the cell surface antigen). The resulting cells are exposed to a first antibody or pool (group) of antibodies directed against the cell surface antigen. This results in formation of a cell surface antigen-first antibody complex. The complexes are exposed to a substrate to which is coated or bound a second antibody directed against the first antibody. Cells expressing the cell surface antigen adhere to the substrate (because of formation of a cell surface antigen-first antibody-second antibody complex). Adherent cells are separated from nonadherent cells.

Isolation of total RNA

The guanidium thiocyanate/CsCl method of isolating total RNA is preferred. More preferred is a guanidium thiocyanate/LiCl variant of the GuSCN/CsCl method, which has added capacity and speed. Briefly, for each ml of mix desired, 0.5 g GuSCN are dissolved in 0.58 ml of 25% LiCl (stock filtered through 0.45 micron filter) and 20 $\mu$l of mercaptoethanol is added. Cells are spun out and the pellet is dispersed on walls by flicking, add 1 ml of Solution up to $5 \times 10^7$ cells. The resulting combination is sheared by polytron until nonviscous. For small scale preps (less than $10^8$ cells) layer 2 ml of sheared mix on 1.5 ml of 5.7M CsCl (RNase free; 1.26 g CsCl added to every ml 10 mM EDTA pH 8), overlay with RNase-free water and spin SW55 50 k rpm 2 h. For large scale preps, layer 25 ml on 12 ml CsCl in a SW28 tube, overlay, and spin 24 k rpm 8 h. Aspirate contents carefully with a sterile pasteur pipet connected to a vacuum flask. Once past the CsCl interface, scratch a band around the tube with the pipet tip to prevent the layer on the wall of the tube from creeping down. The remaining CsCl solution is aspirated. The pellets are taken up in water (do not try to redissolve). 1/10 vol. NaOAc and 3 vol. EtOH are added and the resulting combination is spun. If necessary, the pellet is resuspended in water (e.g., at 70°). Adjust concentration to 1 mg/ml and freeze. Small RNA (e.g. 5 S) does not come down. For small amounts of cells, scale down volumes and overlay GuSCN with RNase-free water on gradient (precipitation is inefficient when RNA is dilute).

Preparation of poly A+ RNA

Next, polyA+ RNA may be prepared, preferably by the oligo dT selection method. Briefly, a disposable polypropylene column is prepared by washing with 5M NaOH and then rinsing with RNase-free water. For each milligram total RNA about 0.3 ml (final packed bed) oligo dT cellulose is used. Oligo dT cellulose is prepared by resuspending about 0.5 ml of dry powder in 1 ml of 0.1M NaOH and transferring it into the column, or by percolating 0.1 NaOH through a previously used column (columns can be reused many times). This is washed with several column volumes of RNase-free water, until pH is neutral, and rinsed with 2–3 ml of loading buffer. The column bed is then removed into a sterile 15 ml tube using 4–6 ml of loading buffer. The total RNA is heated to 70° C. for 2–3 min., LiCl from RNase-free stock is added (to 0.5M), and combined with oligo dT cellulose in a 15 ml tube. This is followed by vortexing or agitation for 10 min. The result is poured into a column and washed with 3 ml loading buffer and then 3 ml of middle wash buffer. mRNA is eluted directly into an SW55 tube with 1.5 ml of 2 mM EDTA, 0.1% SDS; the first two or three drops are discarded.

Eluted mRNA is precipitated by adding 1/10 vol. 3M NaOAc and filling the tube with EtOH. This is then mixed, chilled for 30 minutes at −20° C., and spun at 50 k rpm at 5° C. for 30 min. The EtOH is poured off and the tube is air dried. The mRNA pellet is resuspended in 50–100 $\mu$l of RNase-free water. Approximately 5 $\mu$l is melted at 70° C. in MOPS/EDTA/formaldehyde and run on an RNase-free 1 % agarose gel to check quality.

cDNA Synthesis

From this, cDNA is synthesized. A preferred method of cDNA synthesis is a variant of that described by Gubler and Hoffman (*Gene*, 25:263–269 (1982)). This is carried out as follows:

a. First Strand. 4 $\mu$g of mRNA and heated to about 100° C. in a microfuge tube for 30 seconds and quenched on ice. The volume is adjusted to 70 $\mu$l with RNase-free water. The following are added: 20 $\mu$l of RT1 buffer, 2 $\mu$l of RNAse inhibitor (Boehringer 36 U/$\mu$l), 1 ul of 5 $\mu$g/$\mu$l of oligo dT (Collaborative Research), 2.5 $\mu$l of 20 mM dXTP's (ultrapure), 1 $\mu$l of 1M DTT and 4 l of RT-LX (Life Science, 24 U/$\mu$l). The resulting combination is incubated at 42° C. for 40 min. It is heated to inactivate (70° C. 10 min).

b. Second Strand. 320 $\mu$l of RNAse free water, 80 $\mu$l of RT2 buffer, 5 $\mu$l of DNA Polymerase I (Boehringer, 5 U/$\mu$l), 2 $\mu$l RNAse H (BRL 2 U/$\mu$l). Incubate at 15° C. for 1 hr and 22° C. for 1 hr. Add 20 $\mu$l of 0.5M EDTA pH 8.0, phenol extract and EtOH precipitate by adding NaCl to 0.5M, linear polyacrylamide (carrier) to 20 $\mu$g/ml, and filling tube with EtOH. Spin 2–3 minutes in microfuge, remove, vortex to dislodge precipitate high up on wall of tube, and respin 1 minute.

c. Adaptors. Resuspend precipitated cDNA in 240 $\mu$l of TE (10/1). Add 30 $\mu$l of 10× low salt buffer, 30 $\mu$l of 10× low salt buffer, 30 $\mu$l of 10× ligation additions, 3 $\mu$l (2.4 $\mu$g) of kinased 12-mer adaptor, 2 $\mu$l (1.6 $\mu$g) of kinased 8-mer adaptor, and 1 $\mu$l of T4 DNA ligase (BioLabs, 400 U/$\mu$l, or Boehringer, 1 Weiss unit/ml). Incubate at 15° C. overnight. Phenol extract and EtOH precipitate as above (no extra carrier now needed), and resuspend in 100 $\mu$l of TE.

Use of cDNA fragments in expression vectors

For use with the BstXI-based cDNA expression vectors of the invention (see infra), oligonucleotide segments containing terminal sequences corresponding to BstXI sites on the vectors are ligated to the cDNA fragment desired to be inserted. The resulting fragments are pooled by fractionation. A preferred method is as follows:

Prepare a 20% KOA, 2 mM EDTA, 1 $\mu$g/ml EthBr solution and a 5% KOAc, 2 mM EDTA, 1 $\mu$g/ml EthBr solution. Add 2.6 ml of 20% KOAc solution to back chamber of a small gradient maker. Remove air bubble from tube connecting the two chambers by allowing solution to flow into the front chamber and then tilt back. Close passage between chambers, and add 2.5 ml. of the 5% solution to the front chamber. If there is liquid in the tubing from a previous run, allow the 5% solution to run just to the end of the tubing, and then return to chamber. Place the apparatus on a stirplate, set the stir bar moving as fast as possible, open the stopcock connecting the two chambers and then open the front stopcock. Fill a polyallomer SW55 tube from the bottom with the KOAc solution. Overlay the gradient with 100 $\mu$l of cDNA solution. Prepare a balance tube and spin the gradient for 3 hrs at 50 k rpm at 22° C. To collect fractions from the gradient, pierce the SW55 tube with a butterfly infusion set (with the luer hub clipped off) close to the bottom of the tube and collect three 0.5 ml fractions and then 6 0.25 ml fractions into microfuge tubes (about 22 and 11 drops respectively). EtOH precipitate the fractions by adding linear polyacrylamide to 20 $\mu$g/ml and filling the tube to the top with EtOH. After cooling tubes, spin them in a microfuge for 3 min. Vortex and respin 1 min. Rinse pellets with 70% EtOH (respin). Do not dry to completion. Resuspend each 0.25 ml fraction in 10 $\mu$l of TE. Run 1 $\mu$l on a 1% agarose minigel. Pool the first three fractions, and those of the last six which contain no material smaller than 1 kb.

Suppressor tRNA plasmids may be propagated by known methods. In a preferred method according to the present invention, supF plasmids can be selected in nonsuppressing hosts containing a second plasmid, p3, which contains amber mutated ampicillin and tetracycline drug resistance elements (Seed, 1983). The p3 plasmid is derived from PR1, is 57 kb in length, and is a stably maintained, single copy episome. The ampicillin resistance of this plasmid reverts at a high rate, so that amp$^r$ plasmids usually cannot be used in p3-containing strains. Selection for tet resistance alone is almost as good as selection for amp+tet resistance. However, spontaneous appearance of chromosomal suppressor tRNA mutations presents an unavoidable background (frequency about 10$^{-9}$) in this system. Colonies arising from spontaneous suppressor mutations are usually bigger than colonies arising from plasmid transformation. Suppressor plasmids typically are selected for in LB medium containing amp at 12.5 $\mu$g/ml and tet at 7.5 $\mu$g/ml. For large plasmid preps, M9 casamino acids medium containing glycerol (0.8%) may be used as a carbon source, and the bacteria grown to saturation.

Vector DNA may be isolated by known methods. The following method is preferred for plasmid from 1 liter of saturated cells:

Spin down cells in 1 liter J6 bottles, 4.2 k rpm, 25 minutes. Resuspend in 40 ml 10 mM EDTA pH 8 (Thump on soft surface). Add 80 ml 0.2M NaOH, 1% SDS, swirl until clearish, viscous. Add 40 ml 5M KOAc, pH 4.7 (2.5M KOAc, 2.5M HOAc) shake semi-vigorously (until lumps are 2–3 mm in size). Spin (same bottle) 4.2K rpm, 5 min. Pour supernatant through cheesecloth into 250 ml bottle. Fill bottle with isopropyl alcohol. Spin J6, 4.2 k rpm, 5 min. Drain bottle, rinse gently with 70% EtOH (avoid fragmenting the pellet). Invert bottle, and remove traces of EtOH with Kimwipe. Resuspend in 3.5 ml Tris base/EDTA 20 mM/10 mM. Add 3.75 ml of resuspended pellet to 4.5 g CsCl. Add 0.75 ml 10 mg/ml ethidium bromide, mix. Fill VTi80 tubes with solution. Run at a speed of 80 rpm for 2.5 hours or longer. Extract bands by visible light with 1 ml syringe and 20 gauge or lower needle. Cut top off tube, insert the needle upwards into the tube at an angle of about 30° with respect to the tube, (i.e., as shallowly possible) at a position about 3 mm beneath the band, with the bevel of the needle up. After the band is removed, pour tube contents into bleach. Deposit extracted bands in 13 ml Sarstedt tube. Fill tube to top with n-butanol saturated with 1M NaCl, extract. If a very large quantity of DNA is obtained, reextract. Aspirate butanol into trap containing 5M NaOH (to destroy ethidium). Add about equal volume 1M ammonium acetate to DNA (squirt bottle). Add about 2 volumes 95% ethanol (squirt bottle). Spin 10K rpm, 5 min. J2–21. Rinse pellet carefully with 70% ethanol. Dry with swab, or lyophilizer.

The vector may be prepared for cloning by known methods. A preferred method begins with cutting 20 $\mu$g of vector in a 200 $\mu$l reaction with 100 units of BstXI (New York Biolabs), cutting at 50° C. overnight in a well-thermostatted water bath (i.e., circulating water bath). Prepare 2 KOAc 5–20% gradients in SW55 tubes as described above. Add 100 $\mu$l of the digested vector to each tube and run for 3 hrs, 50K rpm at 22° C. Examine the tube under 300 nm UV light. The desired band will have migrated ⅔ of the length of the tube. Forward trailing of the band means the gradient is overloaded. Remove the band with a 1 ml syringe and 20 gauge needle. Add linear polyacrylamide and precipitate the plasmid by adding 3 volumes of EtOH. Resuspend in 50 $\mu$l of TE. Set up ligations using a constant amount of vector and increasing amounts of cDNAs. On the basis of these trial ligations, set up large scale ligation, which can be accomplished by known methods. Usually the entire cDNA prep requires 1–2 $\mu$g of cut vector.

Adaptors may be prepared by known methods, but it is preferred to resuspend crude adaptors at a concentration of 1 $\mu$g/$\mu$l, add MgSO$_4$ to 10 mM, and precipitate by adding 5 volumes of EtOH. Rinse with 70% EtOH and resuspend in TE at a concentration of 1 $\mu$g/$\mu$l. To kinase take 25 $\mu$l of resuspended adaptors, add 3 $\mu$l of 10× kinasing buffer and 20 units of kinase; incubate 37° C. overnight.

Preparation of buffers mentioned in the above description of preferred methods according to the present invention will be evident to those of skill. For convenience, preferred buffer compositions are as follows:

Loading Buffer: 0.5M LiCl, 10 mM Tris pH 7.5, 1 mM EDTA 0.1% SDS.
Middle Wash Buffer: 0.15M LiCl, 10 mM Tris pH 7.5, 1 mM EDTA 0.1% SDS.
Rt1 Buffer: 0.25M Tris pH 8.8 (8.2 at 42°), 0.25M KCl, 30 mM MgCl$_2$.
RT2 Buffer: 0.1M Tris pH 7.5, 25 mM MgCl$_2$, 0.5M KCl, 0.25 mg/ml BSA, 50 mM DTT.
10× Low Salt: 60 mM Tris pH 7.5, 60 mM MgCl$_2$, 50 mM NaCl, 2.5 mg/ml BSA, 70 mM Me.
10× Ligation Additions: 1 mM ATP, 20 mM DTT, 1 mg/ml BSA, 10 mM spermidine.
10× Kinasing Buffer: 0.5M Tris pH 7.5, 10 mM ATP, 20 mM DTT, 10 mM spermidine, 1 mg/ml BSA 100 mM MgCl$_2$.

By "vector" is meant a DNA molecule, derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible. Thus, by "DNA expression vector" is meant any autonomous element capable of replicating in a host independently of the host's chromosome, after additional sequences of DNA have been incorporated into the autonomous element's genome. Such DNA expression vectors include bacterial plasmids and phages.

Preferred for the purposes of the present invention, however, are viral vectors, such as those derived from simian virus strain 40 (SV40). SV40 is a papovavirus having a molecular weight of 28Mdal, and containing a circular double-stranded DNA molecule having a molecular weight of 3Mdal, which comprises the entire genome of the virus. The entire nucleotide sequence of this single, small, covalently closed circular DNA molecule has been determined. Fiers et al., *Nature* 273:113–120 (1978); Reddy et al., *Science* 200:494–502 (1978). The viral DNA of SV40 may be obtained in large quantities, and the genomic regions responsible for various viral functions have been accurately located with respect to a detailed physical map of the DNA. Fiers et al., supra; Reddy et al., supra. The viral genome of SV40 can multiply vegetatively or as an integral part of cellular chromosomes, and a wealth of information exists on the replication and expression of this genome.

Also preferred for the purposes of the present invention is a single-stranded bacteriophage cloning vehicle, designated M13, having a closed circular DNA genome of approximately 6.5 kb. An advantage of utilizing M13 as a cloning vehicle is that the phage particles released from infected cells contain single-stranded DNA homologous to only one of the two complementary strands of the cloned DNA, which therefore can be used as a template for DNA sequencing analysis.

Even more preferred for the purposes of the present invention are the expression vectors designated piH3, piH3M, and CDM8. CDM8 was deposited at the ATCC on Feb. 24, 1988, and has accession number ATCC 67635.

By "tissue culture" is meant the maintenance or growth of animal tissue cells in vitro so as to allow further differentiation and preservation of cell architecture or function or both. "Primary tissue cells" are those taken directly from a population consisting of cells of the same kind performing the same function in an organism. Treating such tissue cells with the proteolytic enzyme trypsin, for example, dissociates them into individual primary tissue cells that grow well when seeded onto culture plates at high densities. Cell cultures arising from multiplication of primary cells in tissue culture are called "secondary cell cultures." Most secondary cells divide a finite number of times and then die. A few secondary cells, however, may pass through this "crisis period", after which they are able to multiply indefinitely to form a continuous "cell line." Cell lines often will contain extra chromosomes, and usually are abnormal in other respects as well. The immortality of these cells is a feature shared in common with cancer cells.

Preferred cell lines for use as tissue culture cells according to the present invention include the monkey kidney cell line, designated "COS." COS cells are those that have been transformed by SV40 DNA containing a functional early gene region but a defective origin of viral DNA replication. COS cell clone M6 is particularly preferred for use according to the method of the invention. Also preferred for the purposes of the present invention are murine "WOP" cells, which are NIH 3T3 cells transfected with polyoma origin deletion DNA. cDNA may be introduced into the host tissue culture cells of the present invention by any methods known to those of skill. Transfection may be accomplished by, for example, protoplast fusion, by spheroplast fusion, or by the DEAE dextran method (Sussman et al., *Cell. Biol.* 4:1641–1643 (1984)).

If spheroplast fusion is employed, a preferred method is the following variant based on Sandri-Goldrin et al., *Mol. Cell Bio.* 1:743–752 (1981). Briefly, for example, a set of six fusions requires 100 ml of cells in broth. Grow cells containing amplifiable plasmid to OD 600=0.5 in LB. Add spectinomycin to 100 μg/ml (or chloramphenicol to 150 μg/ml). Continue incubation at 37° C. with shaking for 10–16 hours. (Cells begin to lyse with prolonged incubation in spectinomycin or chloramphenicol medium). Spin down 100 ml of culture (JA14/GSA rotor, 250 ml bottle) 5 min. at 10,000 rpm. Drain well, resuspend pellet in bottle with 5 ml cold 20% sucrose, 50 mM Tris-HCL pH 8.0. Incubate on ice 5 min. Add 2 ml cold 0.25M EDTA pH 8.0, incubate 5 min. at 37° C. (waterbath). Place on ice, check percent conversion to spheroplasts by microscopy. In flow hood, slowly add 20 ml of cold DME/10% sucrose/10 mM MgCl$_2$ (dropwise, ca. 2 drops per second). Remove media from cells plated the day before in 6 cm dishes (50% confluent). Add 5 ml of spheroplast suspension to each dish. Place dishes on top of tube carriers in swinging bucket centrifuge. Up to 6 dishes can be comfortably prepared at once. Dishes can be stacked on top of each other, but 3 in a stack is not advisable as the spheroplast layer on the top dish is often torn or detached after centrifugation. Spin at 1000×g 10 min. Force is calculated on the basis of the radius to the bottom plate. Aspirate fluid from dishes carefully. Pipet 1.5–2 ml 50% (w/w) PEG 1450 (or PEG 1000)/500% DME (no serum) into the center of the dish. If necessary, sweep the pipet tip around to ensure that the PEG spreads evenly and radially across the whole dish. After PEG has been added to the last dish, prop all of the dishes up on their lids so that the PEG solution collects at the bottom. Aspirate the PEG. The thin layer of PEG that remains on the cells is sufficient to promote fusion; the layer remaining is easier to wash off, and better cell viability can be obtained, than if the bulk of the PEG is left behind. After 90 to 120 seconds (PEG 1000) or 120 to 150 seconds (PEG 1450) of contact with the PEG solution, pipet 1.5 ml of DME (no serum) into the center of the dish. The PEG layer will be swept radially by the DME. Tilt the dishes and aspirate. Repeat the DME wash. Add 3 ml of DME/10% serum containing 15 μg/ml gentamicin sulfate. Incubate 4–6 hours in incubator. Remove media and remaining bacterial suspension, add more media and incubate 2–3 days. Extensive washing of the cell layer to remove PEG tends to remove many of the cells without any substantial benefit. If the cells are allowed to sit in the second DME wash for a few minutes, most of the spheroplast layer will come up spontaneously; however it is preferred to wash briefly and allow the layer to come off in the complete medium at 37° C.

The PEG solution can be conveniently prepared by melting a fresh bottle of PEG at 60° C. and pouring approximate 50 ml aliquots by means of a 50 ml centrifuge tube into preweighed bottles. The aliquoted PEG is stored at 5° C. in the dark. To make up a fresh bottle, weigh the aliquot, remelt, and add an equal volume of DME (no serum). Adjust the pH with 7.5% Na bicarbonate solution if necessary, and filter sterilize. The resulting PEG solution may be stored up to 3 months at room temperature without detectable adverse consequence.

Transfected host cells will be cultured according to the invention in order to accomplish expression of the protein encoded by the cDNA clone, and to increase the absolute numbers of cells available for subsequent immunoselection. Those skilled in the art will know of appropriate methods and media for this purpose, taking into account the cell type and other variables routinely considered. COS cells, for example, may be cultured in Dulbecco's modified Eagle's medium (DME) supplemented with 10% calf serum and gentamycin sulfate. Transient expression of transfected cells normally can be expected between 48 and 72 hours post-transfection. However, this time period may vary depending upon the type or strain of host cell used and the cell culture conditions, as will be apparent to those of ordinary skill.

Immunoprecipitation, blotting, and cDNA sequencing of genes cloned according to the methods of the present invention may be carried out by any convenient methods known to those of skill. For example, the immunoprecipitation protocol of Clark et al., *Leukocyte Typing II*, Vol. II, pp. 155–167 (1986), is preferred. Southern, Northern, or other blot analysis methods known to those of skill may be employed, using hybridization probes prepared by known methods, such as that of Hu et al. (*Gene* 18:271–277 (1982)). cDNA sequencing also may be accomplished by known methods, including the dideoxynucleotide method of Sanger et al., *Proc. Natl. Acad. Sci. (USA)* 74:5463–5467 (1977).

The antibodies used according to the present invention may be polyclonal or monoclonal. These may be used singly, or in conjunction with other polyclonal or monoclonal antibodies to effect immunoselection of cells expressing the desired antigen or antigens by the methods of the present invention. Methods of preparing antibodies or fragments thereof for use according to the present invention are known to those of skill.

Standard reference works setting forth general principles of immunology include Klein, J., *Immunology: The Science of Self-Nonself Discrimination*, John Wiley & Sons, publisher, New York (1982); Kennett, R., et al., eds., *Monoclonal Antibodies, Hybridoma: A New Dimension in Biological Analyses*, Plenum Press, publisher, New York (1980); Campbell, A., "Monoclonal Antibody Technology" in Burden, R., et al., eds., *Laboratory Techniques in Biochemistry and Molecular Biology*, Vol. 13, Elsevere, publisher, Amsterdam (1984).

The term "antibody" is meant to include the intact molecule as well as fragments thereof, such as, for example, Fab and F(ab)'$_2$ fragments, which also are able to bind to antigen. Polyclonal antibody preparations may be derived directly from the blood of the desired animal species after immunization with the antigen of interest, or a fragment thereof, using any of the standard protocols known to those of ordinary skill. Similarly, monoclonal antibodies may be prepared using known methods (Kohler et al., *Eur. J. Immunol.* 6:292 (1976)). Use of monoclonal antibodies is preferred for the purposes of the present invention.

For the purposes of immunoselection according to the present invention, the tissue culture host cells which have been exposed to antibodies directed against the target cell surface antigen are separated from host cells which do not express the target antigen by distributing the cells onto a substrate coated with antibody directed against the antibody for the antigen. This technique, termed "panning," will be known to those of skill, and is described, for example, by Mage et al., *J. Immunol. Meth.* 15:47–56 (1977), and Wysocki and Sato, *Proc. Natl. Acad. Sci. (USA)* 75:2844–2848 (1978).

Panning according to the methods of the present invention may be carried out as follows:

a. Antibody-coated dishes. Bacteriological 60 mm plates, Falcon 1007 or equivalent, or 10 cm dishes such as Fisher 8-757-12 may be used. Sheep anti-mouse affinity purified antibody (from, for example, Cooper Bio-Medical (Cappell)) is diluted to 10 μg/ml in 50 mM Tris HCl, pH 9.5. Add 3 ml per 6 cm dish, or 10 ml per 10 cm dish. Let sit ca. 1.5 hrs., remove to next dish 1.5 hrs., then to 3rd dish. Wash plates 3× with 0.15M NaCl (a wash bottle is convenient for this), incubate with 3 ml 1 mg/ml BSA in PBS overnight, aspirate and freeze.

b. Panning. Cells will be in 60 mm dishes. Aspirate medium from dish, add 2 ml PBS/0.5 mM EDTA0.02% azide and incubate dishes at 37° C. for 30 min. to detach cells from dish. Triturate cells vigorously with short pasteur pipet, and collect cells from each dish in a centrifuge tube. Spin 4 min. setting 2.5 (200×g) (takes 5 min). Resuspend cells in 0.5–1.0 ml PBS/EDTA/azide/5% FBS and add antibodies. Incubate at least 30 min. on ice. Add an equal volume of PBS/EDTA/azide, layer carefully on 3 ml PBS/EDTA/azide/2% Ficoll, and spin 4 min. at setting 2.5. Aspirate supernatant in one smooth movement. Take up cells in 0.5 ml PBS/EDTA/azide and add aliquots to antibody-coated dishes containing 3 ml PBS/EDTA/azide/5% FBS by pipetting through 100 micron Nylon mesh (Tetko). Add cells from at most two 60 mm dishes to one 60 mm antibody-coated plate. Let sit at room temperature 1–3 hours. Remove excess cells not adhering to dish by gentle washing with PBS/5% serum or with medium. 2 or 3 washes of 3 ml are usually sufficient.

c. Hirt Supernatant. A preferred variant of the method of Hirt, *J. Molec. Biol.* 26:365–369 (1967), is as follows: Add 0.4 ml 0.6% SDS, 10 mM EDTA to panned plate. Let sit 20 minutes (can be as little as 1 min. if there are practically no cells on the plate). Pipet viscous mixture into microfuge tube. Add 0.1 ml 5M NaCl, mix, put on ice at least 5 hrs. Keeping the mixture as cold as possible seems to improve the quality of the Hirt. Spin 4 min., remove supernatant carefully, phenol extract (twice if the first interface is not clean), add 10 ug linear polyacrylamide (or other carrier), fill tube to top with EtOH, precipitate, and resuspend in 0.1 ml. Add 3 volumes EtOH/NaOAc, reprecipitate and resuspend in 0.1 ml. Transform into MC1061/p3, preferably using the high efficiency protocol hereinafter described. If the DNA volume exceeds 2% of the competent cell aliquot, the transformation efficiency will suffer. 5% gives the same number of colonies as 2.5% (efficiency is halved).

It is preferred for this aspect of the present invention to use "blockers" in the incubation medium. Blockers assure that non-specific proteins, proteases, or antibodies present do not cross-link with or destroy the antibodies present on the substrate or on the host cell surface, to yield false positive or false negative results. Selection of blockers can substantially improve the specificity of the immunoselection step of the present invention. A number of non-specific monoclonal antibodies, for example, of the same class or subclass (isotype) as those used in the immunoselection step (e.g., $IgG_1$, $IgG_2A$, IgGm, etc.) can be used as blockers. Blocker concentration (normally 1–100 $\mu g/\mu l$) is important to maintain the proper sensitivity yet inhibit unwanted interference. Those of skill also will recognize that the buffer system used for incubation may be selected to optimize blocking action and decrease non-specific binding.

A population of cells to be panned for those expressing the target cell surface antigen is first detached from its cell culture dish (harvested) without trypsin. The cells then are exposed to a first antibody, which may be polyclonal or monoclonal, directed against the antigen of interest or against a family of related antigens. At this initial stage, a single antibody or a group of antibodies may be used, the choice depending upon the nature of the target antigen, its anticipated frequency, and other variables that will be apparent to those of skill. Target antigens expressed on the surfaces of host cells will form an antigen-antibody complex.

The cells subsequently are placed in close apposition to a substrate, such as a culture dish, filter disc, or the like, which previously has been coated with a second antibody or group of antibodies. This second antibody will be directed against the first antibody, and its choice will be a matter of ordinary skill dictated by, for example, the animal in which the first antibody was raised. For example, if the first antibody was raised in mice, the second antibody might be directed against mouse immunoglobulins, raised in goats or sheep. Cells expressing the target antigen will adhere to the substrate via the complex formed between the antigen, the first antibody, and the second antibody. Adherent cells then may be separated from nonadherent cells by washing. DNA encoding the target antigen is prepared from adherent cells by known methods, such as that of Hirt, *J. Molec. Biol.* 26:365–369 (1967). This DNA may be transformed into *E. coli* or other suitable host cells for further rounds of fusion and selection, to achieve the desired degree of enrichment.

In the usual case, the initial rounds of immunoselection will employ a panel of first antibodies directed against an epitope or group of epitopes common to the family of antigens to which the target antigen belongs. This will be sufficient to narrow the number of clones for future rounds quite significantly. Two such rounds usually will be found adequate, but the number of rounds may vary as mentioned above. Thereafter, a single round of selection may be performed employing a single first antibody or a group of first antibodies recognizing only the target antigen.

By "substrate" is meant a solid surface to which antibodies may be bound for immunoselection according to the present invention. Known suitable substrates include glass, polystyrene, polypropylene, dextran, nylon, and other materials. Tubes, beads, microtiter plates, bacteriological culture dishes, and the like formed from or coated with such materials may be used. Antibodies may be covalently or physically bound to the substrate by known techniques, such as covalent bonding via an amide or ester linkage, or by absorption. Those skilled in the art will know many other suitable substrates and methods for immobilizing antibodies thereupon, or will be able to ascertain such substrates and methods using no more than routine experimentation.

The choice of host tissue culture cells for use according to the present invention preferably should be such as to avoid the situation in which the antibodies used for panning recognize determinants on untransfected cells. Thus, while COS cells are preferred for transient expression of certain surface antigens, more preferred are murine WOP cells. Of the latter, WOP 3027 cells are even more preferred. WOP cells allow virtually all antibodies to be used, since cross-reactions between murine antibodies and murine cell surface determinants are rare.

The insert size of the recombinant DNA molecule should be chosen to maximize the likelihood of obtaining an entire coding sequence. Those of skill will know various methods by which a preliminary determination of optimal insert size for a given gene may be determined.

Vector construction and cDNA insertion

Vectors suitable for expression of cDNA in mammalian tissue culture cells may be constructed by known methods. Preferred for the purposes of the present invention is an expression vector containing the SV40 origin. The vector may contain a naturally derived or synthetic transcription origin, and the SV40 early region promoter. Even more preferred is a chimeric promoter composed of human cytomegalovirus immediate early enhancer sequences. Various "enhancer sequences" also may be used with SV40 vectors. These are described, for example, by Banerji et al., *Cell* 27:299–308 (1981); Levinson et al., *Nature* 295:568–572 (1982); and Conrad et al., *Mol. Cell. Biol.* 2:949–965 (1982).

Insertion of cDNA into the vectors of the present invention can occur, for example, by homopolymeric tailing with terminal transferase. However, homopolymeric tracts located 5' to cDNA inserts may inhibit in vitro and in vivo expression. Thus, preferred for purposes of the present invention is the use of inverted identical cleavage sites separated by a short replaceable DNA segment. Such inverted identical cleavage sites, preferably employing the BstXI restriction endonuclease, may be used in parallel with cDNA synthetic oligonucleotides, y giving the same termini as the replaceable segment of the vector. In this manner, the cDNA cannot ligate to itself, but can ligate to the vector. This allows the most efficient use of both cDNA and vector.

Another embodiment of the present invention is the above-described efficient oligonucleotide-based strategy to promote cDNA insertion into the vector. The piH3M vector of the present invention is preferred, and employs the inverted endonuclease sites. This vector may contain an SV40 origin of replication, but a more preferred form contains an M13 origin. This vector, containing the M13 origin, allows high level expression in COS cells of coding sequences placed under its control. Also, the small size and particular arrangement of sequences in the plasmid permit high level replication in COS cells.

By "cell surface antigen" is meant any protein that is transported through the intracellular membrane system to the cell surface. Such antigens normally are anchored to the cell surface membrane through a carboxyl terminal domain containing hydrophobic amino acids that lie in the lipid bilayer of the membrane, and there exert their biological and antigenic effects. Antigens such as those of T-lymphocytes are particularly suited for gene cloning by the method of the present invention. However, cell surface antigens of any cells may be cloned according to the present method. Moreover, proteins not normally expressed on the cell surface may admit of cloning according to the present method by, for example, using fluorescence activated cell sorting (FACS) to enrich for fixed cells expressing intracellular antigens.

By "substantially pure" is meant any antigen of the present invention, or any gene encoding any such antigen, which is essentially free of other antigens or genes, respectively, or of other contaminants with which it might normally be found in nature, and as such exists in a form not found in nature.

By "functional derivative" is meant the "fragments," "variants," "analogs," or "chemical derivatives" of a molecule. A "fragment" of a molecule, such as any of the antigens of the present invention, is meant to refer to any polypeptide subset of the molecule containing a functional domain such as an epitope, a ligand binding site, an extracellular domain or an immunoglobulin domain, which comprises at least about 6 amino acids. A "variant" of such molecules is meant to refer to a naturally occurring molecule substantially similar to either the entire molecule, or a fragment thereof. An "analog" of a molecule is meant to refer to a non-natural molecule substantially similar to either the entire molecule or a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences*, 16th ed., Mack Publishing Co., Easton, Pa. (1980).

A fragment, variant, analog and/or chemical derivative of a subject antigen is said to be a "functional derivative" of the antigen if the amino acid sequence of the former has at least about 80% identity to the sequence of the latter, and if the former has at least about 30% of a biological activity or function of the latter. Increasingly preferred are amino acid identities that increase integrally, i.e., at least about 81%, 82%, etc. identity. Also, increasingly preferred biological activities are those of at least about 40%, 50%, 60%, 70%, 80%, and 90%.

A nucleotide sequence is said to be a "functional derivative" of a disclosed nucleotide sequence encoding an antigen if the former encodes a disclosed antigen or a functional derivative thereof.

Biological activities are those operations, functions or processes which are characteristic of living organisms. Biological activities can also include the reproduction, extension or adaptation of living processes to in vitro or non-natural systems, such as the biological activity exhibited when an antigen or its functional derivative is artificially introduced into a test animal to induce the production of antibodies. An antigen can have one or more biological activities. Biological activities can be detected or measured by methods or assays that are characteristic for that activity. For a functional derivative to have a biological activity substantially the same as that of an antigen, it must have a biological activity of at least about 30% of that of antigen as measured by an assay characteristic for that activity and known to those of skill in the art.

The substantially pure antigens that have been expressed by methods of the present invention may be used in immunodiagnostic assay methods well known to those of skill, including radio-immunoassays (RIAs), enzyme immunoassays (EIAs) and enzyme-linked immunosorbent assays (ELISAs). The substantially pure proteins of the present invention, in soluble form, may be administered alone or in combination with other antigens of the present invention, or with other agents, including lymphokines and monokines or drugs, for the treatment of immune-related diseases and disorders in animals, including humans. As examples of such disorders that may benefit from treatment with the substantially pure proteins of the present invention may be mentioned immune deficiency diseases, diseases of immediate type hypersensitivity, asthma, hypersensitivity pneumonitis, immune-complex disease, vasculitis, systemic lupus erythematosus, rheumatoid arthritis, immunopathogenic renal injury, acute and chronic inflammation, hemolytic anemias, platelet disorders, plasma and other cell neoplasms, amyloidosis, parasitic diseases, multiple sclerosis, Guillain-Barre syndrome, acute and subacute myopathic paralysis, myasthenia gravis, immune endocrinopathies, and tissue and organ transplant rejection, all as described in Petersdorf et al., eds., *Harrison's Principles of Internal Medicine*, supra. See also Weir, ed., supra; Boguslaski et al., eds., supra; and Holborow et al., eds., supra.

When used for immunotherapy, the antigens of the present invention may be unlabeled or labeled with a therapeutic agent. Examples of therapeutic agents which can be coupled to the antigens of the invention for immunotherapy are drugs, radioisotopes, lectins, and toxins.

The dose ranges for the administration of the antigens of the present invention are those large enough to produce the desired immunotherapeutic effect, but not so large as to cause adverse side effects, such as unwanted cross-reactions, anaphylactic reactions, and the like. Generally, the dosage employed will vary with the age, condition, sex, and extent of the disease in the patient. Counterindications (if any), immune tolerance and other variables also will affect the proper dosage. Administration may be parenteral, by injection or by gradual perfusion over time. Administration also may be intravenous, intraparenteral, intramuscular, subcutaneous, or intradermal.

Preparations for parenteral administration include sterile aqueous or non-aqueous solutions, suspensions and emulsions. Examples of non-aqueous solvents include propylene glycol, polyethylene glycol, vegetable oils such as olive oil, and injectable organic esters such as ethyl oleate. Aqueous carriers include water, alcoholic and aqueous solutions, emulsions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives also may be present, such as, for example, antimicrobials, antioxidants, chelating agents, inert gases and the like. Such preparations, and the manner and method of making them, are known and described, for example, in *Remington's Pharmaceutical Science,* 16th ed., supra.

The antigens of the present invention also may be prepared as medicaments or pharmaceutical compositions comprising the antigens, either alone or in combination with other antigens or other agents such as lymphokines, monokines, and drugs, the medicaments being used for therapy of animal, including human, immune-related indications.

Although the antigens of the present invention may be administered alone, it is preferred that they be administered as a pharmaceutical composition. The compositions of the present invention comprise at least one antigen or its pharmaceutically acceptable salt, together with one or more acceptable carriers and optionally other therapeutic agents. By "acceptable" is meant that the agent or carrier be compatible with other ingredients of the composition and not injurious to the patient. Compositions include those suitable for oral, rectal, nasal, topical (including buccal and sublingual), vaginal, or parenteral administration. The compositions conveniently may be presented in unit dosage form, and may be prepared by methods well known in the pharmaceutical arts. Such methods include bringing into association the active ingredient with the carrier which constitutes one or more accessory ingredients. In general, compositions are prepared by uniformly and intimately bringing into association the active ingredient with liquid carriers or finely divided solid carriers, or both, and shaping the product formed thereby, if required.

Orally administered pharmaceutical compositions according to the present invention may be in any convenient form, including capsules, cachets, or tablets, each containing a predetermined amount of the active ingredient. Powders or granules also are possible, as well as solution or suspension in aqueous or nonaqueous liquids, or oil-in-water liquid emulsions, or water-in-oil liquid emulsions. The active ingredient also may be presented as a bolus, electuary or paste.

Having now described the invention, the same will be more fully understood by reference to the following examples, which are not intended in any way to limit the scope of the invention.

EXAMPLE I

Isolation, Molecular Cloning, and Structure of the Human CD2 Antigen

The cDNA expression vector piH3

A COS cell expression vector was constructed from piSV (Little et al., *Mol. Biol. Med.* 1:473–488 (1983)) by inserting a synthetic transcription unit between the suppressor tRNA gene and the SV40 origin. The transcription unit consisted of a chimeric promoter composed of human cytomegalovirus AD169 immediately early enhancer sequences fused to the HIV LTR −67 to +80 sequences. Immediately downstream from the LTR +80 sequence was inserted a polylinker containing two BstXI sites separated by a 350 bp stuffer; the BstXI sites were flanked by XbaI sites, which could also be used to excise the insert. Downstream from the polylinker were placed the SV40 small t antigen splice and early region polyadenylation signals derived from pSV2. The nucleotide sequence of the vector is shown in FIGS. 1A–1B.

cDNA library construction

RNA was prepared from HPB-ALL cells by the guanidinium thiocyanate/CsCl method, as described above. PolyA$^+$ RNA was prepared from total RNA by oligo dT selection. Maniatis et al. *Molecular Cloning: A Laboratory Manual,* supra. cDNA was synthesized by the method of Gubler and Hoffman (*Gene* 25:263–269 (1982)). BstXI adaptors were ligated to the cDNA, and the reaction products fractionated by centrifugation through a 5 ml-20% potassium acetate gradient containing 1 mM EDTA for 3 hours at 50 k rpm in a SW55 rotor. 0.5 ml fractions were collected manually through a syringe needle or butterfly inserted just above the curve of the tube. Individual fractions were ethanol-precipitated after addition of linear polyacrylamide (Strauss and Varshavsky, *Cell* 37:889–901 (1984)) to 20 µg/ml. Fractions containing cDNA larger than 700 bp were pooled and ligated to gradient purified BstXI digested piH3 vector.

The ligated DNA was transformed into *E. coli* MC1061/p3 made competent by the following protocol: The desired strain was streaked out on an LB plate. The next day a single colony was inoculated into 20 ml TYM broth (recipes below) in a 250 ml flask. The cells were grown to midlog phase ($OD_{600}$ about 0.2–0.8), poured into a 2 l flask containing 100 ml TYM, and vigorously agitated until cells grew to 0.5–0.9 OD, then diluted again to 500 ml in the same vessel. When the cells grew to $OD_{600}$ 0.6, the flask was placed in ice-water, and shaken gently to assure rapid cooling. When the culture was cool, it was spun at 4.2 k rpm for 15 minutes (J6). The supernatant was poured off and the pellet resuspended in about 100 ml cold TfB I (below) by gentle shaking on ice. Thereafter, it was respun in the same bottle at 4.2 k rpm for 8 minutes (J6). The supernatant was poured off and the pellet resuspended in 20 ml cold TfB II by gentle shaking on ice. 0.1 to 0.5 ml aliquots were placed in prechilled microfuge tubes, frozen in liquid nitrogen, and stored at −70° C. For transformation, an aliquot was removed, thawed at room temperature until just melting, and placed on ice. DNA was added, let sit on ice 15–30 minutes, and incubated at 37° C. for 5 minutes (6 minutes for 0.5 ml aliquots). Thereafter the DNA-containing suspensions were diluted 1:10 in LB and grown for 90 minutes before plating or applying antibiotic selection. Alternatively, the heat-pulsed transformation mix was plated directly on antibiotic plates onto which a thin (4–5 ml) layer of antibiotic-free LB agar was poured just before plating.

Media and Buffers: TYM: 2% Bacto-Tryptone, 0.5% Yeast Extract, 0.1M NaCl, 10 mM MgSO$_4$ (can be added before autoclaving). TfB I: 30 mM KOAc, 50 mM MnCl$_2$, 100 mM KCL, 10 mM CaCl$_2$, 15% (v/v) glycerol. TfB II: 10 mM Na-MOPS, pH 7.0, 75 MM CaCl$_2$, 10 mM KCl, 15% glycerol.

Recovery of cDNA clones by panning

Bacteriological culture dishes (Falcon 1007) were prepared for panning by coating with an affinity purified sheep anti-mouse IgG antibody as described by Wysocki and Sato (*Proc. Natl. Acad. Sci. USA* 75:2844–2848 (1978)), except that dishes were washed with 0.15M NaCl from a wash bottle instead of PBS, and unreacted sites were blocked by overnight incubation in PBS containing 1 mg/ml BSA. Dishes were typically prepared in large batches and stored frozen, after aspiration of the PBS/BSA. In the first round of screening, 24 6 cm dishes of 50% confluent COS cells were transfected by protoplast fusion according to the method of Sandri-Goldrin et al., *Mol. Cell Biol.* 1:743–752 (1981). 72 hours post fusion the cells were detached by incubation in PBS/1 mM EDTA/0.02% sodium azide at 37° C. for 30 minutes. The detached cells were pooled, centrifuged, and resuspended in cold PBS/EDTA/5% Fetal Bovine Serum containing monoclonal antibodies, usually as ascites at 1:1000 dilution, but also as commercial reagents at the concentrations suggested by the manufactures. After 1 hour on ice, the cells were diluted with 1:1 with PBS/EDTA/azide and layered on 10 ml of PBS/EDTA/azide containing 2% Ficoll 400. After centrifugation (400×g, 5 minutes), the supernatant was carefully aspirated, the pellet resuspended in a small amount of PBS/EDTA/5% FBS, and the cells distributed into panning plates containing 3 ml of PBS/EDTA/5% FBS. The plates were then treated essentially as described by Wysocki and Sato, *Proc. Natl. Acad. Sci. USA* 75:2844–2848 (1978). Episomal DNA was recovered from the adherent cells by the Hirt (*J. Mol. Biol.* 26:365–269 (1967)) procedure and transformed into MC1061/p3.

Cell lines and cell culture

COS cell clone M6 cells were propagated in Dulbecco's modified Eagle's medium supplemented with 10% calf serum and gentamycin sulfate at 15 μg/ml (DME/10% calf serum). Cells were split the day before transfection in 6 cm dishes at approximately 1:8 ratio from stock plates kept as dense as possible without overtly affronting the cells. T cell lines were grown in Iscove's modification of Dulbecco's medium (IMDM) containing gentamycin as above, and either NuSerum (Collaborative Research) or fetal bovine serum at 10%.

COS cell transfection for immunofluorescence studies

COS cells at 50% confluence in 6 cm dishes were transfected in a volume of 1.5 ml with a cocktail consisting of DME or IMDM medium containing 10% NuSerum (Collaborative Research), 400 μg/ml DEAE Dextran, 10 μM chloroquine diphosphate, and 1 μg/ml DNA. After 4 hours at 37° C. (or earlier if the cells appeared ill), the transfection mix was removed and the cells were treated with 10% DMSO in PBS for 2 minutes. Sussman and Milman, *Cell Biol.* 4:1641–1643 (1984). Cells were then returned to DME/10% calf serum for 48 to 72 hours to allow expression.

Immunoprecipitations, Northerns and Southerns

T cells were labeled by lactoperoxidase treatment, lysed, and immunoprecipitated by the procedure of Clark and Einfeld (*Leukocyte Typing II,* Vol. II, pp. 155–167 (1986)), using commercially available goat anti-mouse IgG agarose beads (Cooper Biomedical). COS cells were transfected by DEAE Dextran method and trypsinized and passed without dilution into new plates 24 hours after transfection. 36 hours later, cells were detached by exposure to PBS/EDTA as above, centrifuged, and labeled by the lactoperoxidate method. A cleared lysate was prepared as for the T cell immunoprecipitations, except that the lysis buffer contained 1 mM PMSF, and incubation with the primary antibody was carried out for only 2 hours at 4° C. Eluted samples were fractionated on discontinuous 11.25% polyacrylamide gels using the buffer system of Laemmli (*Nature* 227:680–685 (1970)).

Northern blot analysis was carried out essentially as described (Maniatis et al., *Molecular Cloning, a Laboratory Manual* (1982)), except that DMSO was omitted from the loading buffer, denaturation was at 70° C. for 5 minutes, and the gel contained 0.6% formaldehyde rather than 6%. The gel was stained in two volumes of water containing 1 μg/ml ethidium bromide, photographed, and transferred to nylon (GeneScreen, DuPont) in the staining liquor. The transferred RNA was irradiated by exposure to a germicidal lamp through Saran Wrap (Church and Gilbert, *Proc. Natl. Acad. Sci. USA* 8:1991–1995 (1984)) for 5 minutes at a flux (measured at 254 nm) of 0.22 mW/cm$^2$. Southern blot analysis was carried out by alkaline transfer to nylon (GeneScreen, DuPont) as described by Reed and Mann (*Nucl. Acids Res.* 13:7207–7221 (1986)). Hybridization probes were prepared by the method of Hu and Messing (*Gene* 18:271–277 (1982)), and blots were prehybridized in SDS/phosphate buffer (Church and Gilbert, *Proc. Natl. Acad. Sci. USA* 8:1991–1995 (1984)) containing 10 DNA microgram equivalents of M13 mp19 phage.

Erythrocyte Rosetting

Erythrocytes were prepared from whole blood by three centrifugations in PBS. COS cells were transfected in 6 cm dishes with CD2 or other surface antigen expression clones by the DEAE method. 48 to 72 hours posttransfection, the medium was aspirated and 2 ml of PBS/5% FDS/azide was added to each plate, followed by 0.4 ml of the appropriate erythrocyte samples as 20% suspensions in PBS. After 1 hour at room temperature, the nonadherent erythrocytes were gently washed off, and the plates examined.

A cDNA encoding CD2 antigen determinants was isolated in the following manner: cDNA was prepared from RNA extracted from the human T Cell tumor line HPB-ALL and inserted into the SV40 origin-based expression vector piH3 as described above. A cDNA library of approximately 3×10$^5$ recombinants was constructed, and the library was introduced into COS cells by protoplast fusion. Three days later the cells were detached by exposure to EDTA and treated with a pool of monoclonal antibodies, including three (OKT11, Leu5b, and Coulter T11) directed against CD2 determinants. The antibody-treated cells were distributed into dishes coated with an affinity purified sheep anti-mouse IgG antibody, allowed to attach, and separated from the nonadherent cells by gentle washing. This method of enrichment is known in the immunological literature (Mage et al. *J. Immunol. Methods* 15:47–56 (1977).

The resulting colonies were pooled, fused into COS cells, and subjected to a second round of panning as before. In the third round, a portion of the detached cells was treated with a mixture of three monoclonal antibodies specific for CD2, and a Hirt supernatant was again generated and transformed into *E. coli*. DNA was prepared from eight of the resulting colonies and transfected into COS cells. After three days, surface expression of the CD2 antigen was detected by indirect immunofluorescence in six of eight transfected dishes. Restriction enzyme digestion of the corresponding plasmid DNAs revealed a 1.5 kb insert in all six isolates.

One of the six clones was prepared in larger quantities for further analysis. Following transfection into COS cells, indirect immunofluorescence analysis with a partial panel of antibodies provided by the Third International Workshop on Leukocyte Differentiation Antigens showed that all of the antibodies provided gave positive reactions with the exception of one sample which also failed to react with phytohemagglutinin-activated T lymphocytes. Among the 17 antibodies tested were at least eight distinguishable groups defined by their differing patterns of reactivity with lymphocytes of various primate species. Jonker and Nooij, *Leukocyte Typing II,* Vol. I, pp. 373–387 (1986).

cDNA sequence analysis

The CD2 cDNA insert was subcloned into M13 mp19 (Vieira and Messing, *Gene* 19:259–268 (1982)) in both orientations, and the sequence determined by the dideoxynucleotide method (FIGS. 2A and 2B). Sanger et al., *Proc. Natl. Acad. Sci. USA* 74:5463–5467 (1977). An open reading frame was observed to extend 360 residues from an ATG triplet satisfying the consensus criteria of Kozak (*Microbiol. Rev.:* 1–47:45 (1983)) for translational initiation codons (FIG. 1). The predicted amino acid sequence evokes an integral membrane protein with a single membrane spanning hydrophobic anchor terminating in a rather large intracytoplasmic domain. Comparison of the N-terminal amino sequence with the matrix of signal sequence residue frequencies constructed by von Heijne (*Nucl. Acids Res.* 14:4683–4690 (1986)) suggests that mature CD2 peptide is formed by cleavage of a precursor peptide between the 19th (Ser) and 20th (Lys) residues.

A surprising and unexpected feature of this sequence is the presence of a potential N-linked glycosylation site just proximal to the proposed cleavage site. The resulting polypeptide backbone has a predicted molecular weight of 38.9 kd divided into an external domain of mass 21.9 kb and a cytoplasmic domain of mass 14.6 kd. Three N-linked glycosylation sites are present in the extracellular domain.

The membrane spanning domain comprises 26 unchanged residues of predominantly hydrophobic character. In the nine residues immediately following are seven basic residues, either lysines or arginines. The appearance of predominantly hydrophobic residues followed by basic residues is a common organizational feature of transmembrane proteins bearing carboxyl-terminal anchors.

Another surprising feature of the transmembrane domain is the appearance of a cys-gly-gly-gly, a beta turn motif (Chou and Fasman, *Annual Review of Biochemistry* 47:251–276 (1978)), flanked by hydrophobic residues (which are frequently found flanking beta turns). Because only 20 residues arrayed in an alpha helix are theoretically needed to traverse the 3 nm membrane bilayer (Tanford, *Science* 200:1012–1018 (1978)), and as few as 14 hydrophobic residues can allow insertion and export of an integral membrane protein (Adams and Rose, *Cell* 41:1007–1015 (1985)), the transmembrane segment of the CD2 antigen may contain a bend or kink.

The rather large size of the cytoplasmic domain leaves open the possibility that CD2 possesses an intrinsic enzymatic activity. The cytoplasmic domain is very rich in prolines and contains three sites with high turn probability.

Comparison of the amino acid sequence with the NBRF database revealed no substantive homologies with other proteins. In particular, no homology with the T cell receptor alpha or beta chains was observed, ruling out the suggestion that CD2 is a primordial T cell receptor. Milanese et al., *Science* 231:1118–1122 (1986).

Just inside the cytoplasmic face of the protein is a run of basic proteins followed by a serine residue, a pattern found at the same location in both the EGF receptor and the class I histocompatibility genes, and in each case a known site for either in vivo (EGF) and in vitro (HLA) phosphorylation by protein kinase C or cyclic AMP-dependent protein kinase, respectively. Hunter et al., *Nature* 311:480–482 (1984); Davis and Czech, *Proc. Natl. Acad. Sci.* 82:1974–1978 (1985); Guild and Strominger, *J. Biol. Chem.* 259:9235–9240 and 13504–13510 (1984). A similar site is found in the intracytoplasmic domain of the interleukin 2 receptor, and is phosphorylated in vivo by protein kinase C. Leonard et al., *Nature* 311:626–631 (1984); Nikaido et al., *Nature* 311:631–635 (1984); Shackelford and Trowbridge, (1984) *J. Biol. Chem.* 259:11706.

Immunoprecipitation of CD2 antigen expressed by transfected cells

COS cells were transfected with the CD2 expression plasmid and surface labeled with $^{125}$I by the lactoperoxidase method 60 hours post-transfection. A cell lysate was prepared, and portions were incubated either with monoclonal anti-CD2 antibody (OKT11) or with an extraneous (OKT4; anti-CD4) antibody for 2 hours at 4° C. Sepharose-bound anti-mouse antibody was added, and after several washing steps, the adsorbed proteins were eluted and electrophoresed through a 11.25% acrylamide gel together with similarly prepared immunoprecipitates from phytohemagglutinin-activated T lymphocytes, the cDNA donor line HPB-ALL, or a long-term T cell line generated in this laboratory. Autoradiography demonstrated a prominent band of immunoreactive material precipitated from transfected COS cells by the anti-CD2 antibody, but not by the control. The calculated mean molecular weight of the COS cell material was 51 kd, compared to a mean molecular weight of 54 kd for the T blast and T cell line material; the antigen from HPB-ALL cells was found to have a molecular weight of approximately 61 kd. The observed differences in size were attributed to different patterns of glycosylation in the different cell types. A minor band of apparent molecular weight 38 kd was present in material immunoprecipitated from COS cells but not from T cells or HPB-ALL cells. The size of this species agrees within experimental error with the predicted molecular weight of mature unglycosylated peptide, 39 kd.

COS cells expressing CD2 form rosettes with sheep erythrocytes

COS cells transfected with the CD2 expression clone were treated for 1 hour with purified MT910 (IgG, kappa) anti-CD2 antibody (Rieber et al., *Leukocyte Typing II,* Vol. I, pp. 233–242 (1986)) at a concentration of 1 μg/ml, or with purified MB40.5 (IgGl, kappa; Kawata et al., *J. Exp. Med.* 160:633–651 (1984)) antibody at the same concentration. MB40.5 recognizes a monomorphic HLA-ABC determinant and cross-reacts with African Green Monkey histocompatibility antigens; it was chosen because it represents an isotype-matched antibody recognizing a surface antigen of approximately the same abundance as the CD2 antigen expressed by transfected cells. Sheep erythrocyte rosettes were observed in the presence of MB40.5, but not of MT910. Rosette inhibition was also observed with OKT11 antibody, and not with various other control antibodies.

Transfected COS cells form rosettes with other animal erythrocytes

In addition to sheep erythrocytes, human T cells are known to form rosettes with horse, pig, dog, goat, and rabbit, but not mouse or rat erythrocytes. Johansen et al., *J. Allergy Clin. Immunol.* 54:86–94 (1974); Amiot et al., in, A. Bernard et al., eds., *Leucocyte Typing,* Springer, publisher, New York, N.Y., pp. 281–293 (1984); Nalet and Fournier, *Cell.*

*Immunol.* 96:126–136 (1985). Autorosettes between human erythrocytes and human thymocytes (Baxley et al., *Clin. Exp. Immunol.* 15:385–393 (1973)) have also been reported. COS cells transfected with the CD2 expression clone were treated with either MT910 or with the control antibody, MB40.5, and exposed to erythrocytes from the species above. Rosettes were observed with horse, pig, dog, goat, sheep, rabbit, and human erythrocytes, but not with mouse or rat erythrocytes. Rosette formation was blocked by pretreatment of transfected COS cells with MT910, but not with MB40.5. In these experiments, it was noticed that horse erythrocytes formed unusually dense rosettes, and that goat erythrocytes formed rather sparse rosettes, possibly because their small size made them more susceptible to washing. Mouse erythrocytes showed weak spontaneous binding to the culture dish as well as to MT910 and MB40.5 pretreated cells, while rat erythrocytes showed no detectable binding of any sort.

Binding of human erythrocytes is blocked by LFA3 antibody

Because it has been suggested on the basis of antibody blocking studies that LFA3 is the target structure for the CD2 antigen (Shaw et al., *Nature* 323:262–264 (1986)), the ability of anti-LFA3 antibody to prevent rosette formation was investigated. Transfected cells were exposed to human erythrocytes pretreated for 2 hours with either anti-LFA3 (IgGl, kappa) as ascites at 1:1000 dilution, or with a 10 µg/ml concentration of each of four isotype-matched nonagglutinating antibodies directed against human erythrocyte antigens as prevalent or more prevalent than LFA3:G10/B11 and D10, anti-K14 antigen, D6, anti-$Wr^b$ antigen; and F7/B9, anti-k antigen. Nichols et al., *Vox Sang,* in press. The erythrocytes were washed free of excess LFA3 antibody, but were allowed to form rosettes in the presence of the control antibodies to guard against possible loss of antibody blocking power by desorption. Rosette formation was observed in the presence of all four control antibodies, but not with erythrocytes pretreated with anti-LFA3.

COS cells expressing other T cell antigens do not form rosettes

A number of clones were isolated by the same expression technique used to clone CD2 and characterized to varying degrees by antibody reactivity, nucleic acid restriction and sequence analysis, and immunoprecipitation. Representative clones were transfected into COS cells and analyzed for ability to sustain rosette formation. The CD1a, CD1b, CD1c, CD4, CD5, CD6, CD6, CD8, and CD28 (Tp44) clones did not form rosettes with human erythrocytes.

RNA blot analysis

Equal amounts of total RNA prepared from cell types expressing or lacking CD2 antigen were electrophoresed through denaturing agarose gels and transferred to nylon. Hybridization of the transferred RNA with a strand selective probe (Hu and Messing, *Gene* 17:271–277 (1982)) prepared from an M13 clone containing a CD2 cDNA insert revealed the presence of prominent 1.65 and 1.3 kb transcripts present in RNA derived from thymocyte, activated T cell, and senescent T cell populations. Lesser amounts were found in RNA extracted from the cDNA donor line, HPB-ALL and less still from MOLT4; barely detectable levels were recorded in RNA from the HSB-2 line. No reactivity was observed with RNA from Namalwa (Burkitt lymphoma), U937 (histiocytic leukemia), HuT-78 (Adult T cell leukemia), PEER (T cell leukemia), or Jurkat clone J3R7 (T cell leukemia) lines. The pattern of reactivity conformed well with the known or measured pattern of expression of CD2 antigen, which was absent or indetectable on the Namalwa, *937, HuT-78, J3R7, PEER, and HSB-2 cell lines, weakly present on MOLT4, more strongly present on EPB-ALL, and most strongly present on activated T cells. Thymocytes are also known to express high levels of CD2 antigen.

Examination of the sequence of the cDNA clone suggested that the 1.3 kb RNA might arise by formation of an alternate 3' end distal to the canonical polyadenylation signal AATAAA at position 1085 in the cDNA sequence. To test this notion, RNA from HPB-ALL and activated T cells was subjected to Northern blot analysis and hybridized either with a complete cDNA probe, or with a probe derived from the 3' portion of the cDNA distal to nucleotide 1131. The latter probe reacted only with the 1.65 kb species, while the former showed the same reactivity pattern observed in FIG. 5. This result is consistent with the suggested origin of the 1.3 kb transcript.

In both activated and senescent T cell RNA preparations, a weakly hybridizing transcript of approximately 0.75 kb was detected. At present the origin of this RNA is unknown.

Genomic organization of the CD2 gene

Southern blot analysis of genomic DNA from placenta, peripheral blood lymphocytes, T cells, HeLa cells, or the tumor lines used in the RNA analysis above showed identical BamHI digest patterns, indicating that rearrangement is not involved in the normal expression of the CD2 gene during development. Similarly, no gross genomic alteration underlies the failure of the examined T cell tumor lines to express CD2 antigen. Restriction analysis of total genomic DNA with a number of other enzymes, as well as preliminary results with an incomplete collection of 1 phage recombinants bearing the CD2 sequence, shows that the gene is divided into at least four exons.

EXAMPLE II

Isolation and Molecular Cloning of Human LFA-3 Antigen

The previous example shows that cDNAs encoding surface antigens, such as the CD2 antigen, can be isolated by the transient expression system of the present invention, in which COS cells transfected with cDNA libraries are allowed to attach to ("panned" on) antibody-coated plates. Plasmid DNA is recovered from cells adhering to the plates, transformed into *E. coli,* and the process is repeated, usually twice, to isolate the desired clone. Although powerful, this approach cannot be used when the monoclonal antibodies used for panning recognize determinants on the untransfected cells. This appears to be the case for anti-LFA3 monoclonal TS2/9. However, a similar transient expression system based on polyoma virus replication-competent cells should allow almost all monoclonals to be used, since the probability of cross reaction between murine antibodies and murine cell surface determinants should usually be small.

A new expression vector, CDM8 (FIG. 3) was created from the COS cell vector piH3M described previously. The new vector differs by the inclusion of a deleted version of a mutant polyoma virus early region selected for high efficiency expression in both murine and monkey cells, by the replacement of substantially all of the human immunodeficiency promoter region with the cognate sequences of the human cytomegalovirus immediate early promoter, and by inclusion of a bacteriophage T7 promoter between the eukaryotic promoter and the site of cDNA insertion. Expression in COS cells of chloramphenicol acetyltransferase by all of the vectors was equivalent.

A library of $1.9 \times 10^6$ recombinants having inserts greater than 0.8 kb in size was prepared in the CDM8 vector from a microgram of poly A+ RNA isolated from the human lymphoblastoid cell line JY. The library was introduced into WOP cells (NIH 3T3 cells transfected with polyoma origin deletion DNA) by spheroplast fusion, and subjected to three rounds of panning and reintroduction into E. coli as described in Example I.

A clone encoding the LFA-3 antigen was identified by indirect immunofluorescence of transfected WOP cells, amplified and sequenced (FIG. 4A). Within the 874 bp insert, an open reading frame of 237 residues originates at a methionine codon closely corresponding to the consensus sequence suggested by Kozak, *Microbiol. Rev.* 47:1–45 (1983). The reading frame terminates in a series of hydrophobic residues lacking the characteristic basic anchoring residues of internal membrane proteins, but sharing features with known phosphatidylinositol-linked superficial membrane proteins. The features include clustered serine or threonine residues in a hydrophilic region immediately preceding the hydrophobic domain, and the presence of serines and threonines in the hydrophobic portion.

The amino acid sequence predicted from the nucleotide sequence of the LFA-3 clone was compared to the NBRF database, and no significant homologies were uncovered; the most significant scores were to the HIV envelope protein. Within the 200 residues comprising the presumed mature protein are 6 N-linked glycosylation sites, and 5 tandem serine or tandem threonine residues that frequently appear in O-linked glycosylated proteins. Ten cysteine residues appear in the complete sequence, 6 of which are distributed in the latter half of the mature protein, and one of which falls in the carboxy-terminal hydrophobic domain. Although esterification of cysteine thiols to fatty acids is a common occurrence in integral membrane proteins, and may play an alternate role in membrane anchoring of LFA-3, two examples are known of cysteine residues within or at the margin of the hydrophobic region of phosphatidylinositol linked proteins.

The predicted sequence suggests that the known manipulations for increasing erythrocyte adhesion to T cells may find direct physical explanation in the structure of the LFA-3 molecule. Aminoethylisothiouronium bromide, the thiourea adduct of bromoethylamine, undergoes spontaneous rearrangement to mercaptoethylguanidine at alkaline pH. The latter likely gains access to disulfide bonds inaccessible to less chaotropic reducing agents and may thereby reduce and promote the unfolding of the LFA-3 molecule. Similarly, neuraminidase may decrease steric interference by the many carbohydrate chains on the molecule.

RNA and DNA blot hybridization analysis showed that the LFA-3 gene shares no closely related sequences in the genome, and encodes a single RNA species of about 1 kb in length. Cell lines that express large amounts of surface LFA-3 have greater amounts of LFA-3 RNA than those that express small or nondetectable amounts.

Radioimmunoprecipitation of the antigen expressed in transfected COS and murine cells shows a broad band of approximately 50 kd mean molecular mass, similar to that found in JY cells.

EXAMPLE III

Isolation and Molecular Cloning of the Human CD28 cDNA Antigen

The previous examples illustrate the monoclonal antibody-based technique of the present invention for enrichment of cDNAs encoding surface antigens. In the present example, a method of constructing plasmid expression libraries is described which allows the enrichment technique to be fully exploited. The method of the present invention for making plasmid expression libraries is of general use for expression cloning.

The antibody selection technique of the present invention has also been applied to isolate a cDNA clone encoding the CD28 antigen. The antigen shares substantial homology with members of the immunoglobulin superfamily and forms a dimer structure on the surface of transfected COS cells similar to the dimer structure found on T lymphocytes.

Preparation of cDNA Libraries

Poly(A)+ RNA was prepared from the human T-cell tumor line HPB-ALL by oligo(dT) cellulose chromatography of total RNA isolated by the guanidinium thiocyanate method (Chirgwin, J. M. et al., *Biochemistry* 18:5294–5299 (1979)). cDNA was prepared by a protocol based on the method of Gubler and Hoffman (Gubler, U. et al., *Gene* 25:263–269 (1982)). 4 µg of mRNA was heated to approximately 100° C. in a 1.5 ml centrifuge tube for 30 seconds, quenched on ice, and the volume adjusted to 70 µl with RNAse-free water. To this were added 20 µl of buffer (0.25M Tris pH 8.8 (8.2 at 42° C.), 0.25M KCl, 30 mM MgCl$_2$), 2 µl of RNAse inhibitor (Boehringer 36 U/µl), 1 µl of 1M DTT, 1 µl of 5 µg/µl of oligo dT (Collaborative Research), 2 µl of 25 mM each deoxynucleoside triphosphate (U.S. Biochemicals), and 4 µl of reverse transcriptase (Life Sciences, 24 U/µl). After 40 minutes at 42° C., the reaction was terminated by heating to 70° C. for 10 minutes. To the reaction mix was then added 320 µl of RNAse free water, 80 µl of buffer (0.1M Tris pH 7.5, 25 mM MgCl$_2$, 0.5M KCl, 0.25 mg/ml BSA, and 50 mM DTT), 25 units of DNA Polymerase I (Boehringer), and 4 units of RNAse H (BRL). After 1 hour at 15° C. and 1 hour at 22° C., 20 µl of 0.5M EDTA pH 8.0 were added, the reaction mixture was extracted with phenol, NaCl was added to 0.5M, linear polyacrylamide (carrier; Strauss, F. et al., *Cell* 37:889–901 (1984)) was added to 20 µg/ml, and the tube was filled with ethanol. After centrifugation for 2–3 minutes at 12,000×g, the tube was removed, vortexed to dislodge precipitate spread on the wall of the tube, and respun for 1 minute.

Unpurified oligonucleotides having the sequence CTCTAAAG and CTTTAGAGCACA were dissolved at a concentration of 1 mg/ml, MgSO$_4$ was added to 10 mM, and the DNA precipitated by adding 5 volumes of EtOH. The pellet was rinsed with 70% ETOH and resuspended in TE at a concentration of 1 mg/ml. 25 µl of the resuspended oligonucleotides were phosphorylated by the addition of 3 µl of buffer (0.5M Tris pH 7.5, 10 mM ATP, 20 mM DTT, mM spermidine, 1 mg/ml BSA, and 10 mM MgCl$_2$) and 20 units of polynucleotide kinase followed by incubation at 37° C. overnight.

3 µl of the 12-mer and 2 µl of the 8-mer phosphorylated oligonucleotides were added to the cDNA prepared as above in a 300 µl reaction mixture containing 6 mM Tris pH 7.5, 6 mM MgCl$_2$, 5 mM NaCl, 0.35 mg/ml BSA, 7 mM mercaptoethanol, 0.1 mM ATP, 2 mM DTT, 1 mM spermidine and 400 units T4 DNA ligase (New England BioLabs) at 15° overnight. 10 µl of 0.5M EDTA were added, the reaction was phenol extracted, ethanol precipitated, resuspended in a volume of 100 µl and layered on a 5 ml gradient of 5–20% potassium acetate in 1 mM EDTA, 1 µg/ml ethidium bromide. The gradient was spun 3 hours at 50,000 rpm (SW55 rotor) and fractionated manually, collecting three approximately 0.5 ml fractions followed by six approximately 0.25 ml fractions in microcentrifuge tubes by means of a butterfly infusion set inserted just above the curve of the tube. Linear polyacrylamide was added to 20

μg/ml, the tubes were filled with ethanol, chilled, spun, vortexed and respun as above. The precipitate was washed with 70% ethanol, dried, and resuspended in 10 μl. 1 μl of the last 6 fractions was run on a gel to determine which fractions to pool, and material less than 1 kb in size was typically discarded. Remaining fractions were pooled and ligated to the vector.

Figure 5:
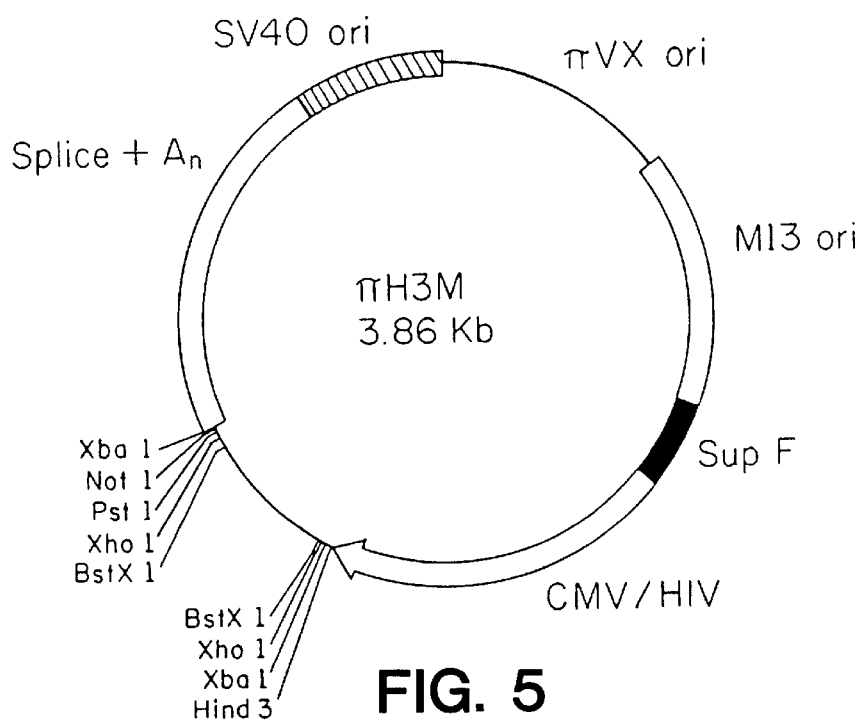
FIG. 5.
Restriction Map of the piH3M vector
The direction of transcription is indicated by an arrow. Restriction endonuclease sites flanking the BstXI cloning sites are shown.

The complete sequence and derivation of the vector is shown in FIG. 5. The vector was prepared for cloning by digestion with BstXI and fractionation on 5–20% potassium acetate gradients as described for the cDNA. The appropriate band was collected by syringe under 300 nm UV light and ethanol precipitated as above. cDNA and vector were titrated in test ligations. Usually 1–2 μg of purified vector were used for the cDNA from 4 μg of poly A+ RNA. The ligation reactions were composed as described for the adaptor addition above. The ligation reactions were transformed into MC1061p3 cells made competent as described above. The transformation efficiency for supercoiled vector was $3-5 \times 10^8$ colonies/μg.

Recovery and characterization of the CD28 clone

Panning of the library was carried out as described herein above, using purified antibody 9.3 (DuPont) at a concentration of 1 ug/ml in the antibody cocktail. The methods used for COS cell transfection, radioimmunoprecipitation, RNA and DNA blot hybridization, and DNA sequencing were all as described herein above.

To isolate the CD28 cDNA, a large plasmid cDNA library was constructed in a high efficiency expression vector containing an SV40 origin of replication. A preferred version of the vector, containing an M13 origin, is shown in FIGS. 6A–6B. Three features of the vector make it particularly suitable for this use: (i) the eukaryotic transcription unit allows high level expression in COS cells of coding sequences placed under its control; (ii) The small size and particular arrangement of sequences in the plasmid permit high level replication in COS cells; and (iii) the presence of two identical BstXI sites in inverted orientation and separated by a short replaceable fragment allows the use of an efficient oligonucleotide-based strategy to promote cDNA insertion in the vector.

The BstXI cleavage site, CCAN'$_5$NTGG, creates a four base 3' extension which varies from site to site. A vector was created in which two identical sites were placed in inverted orientation with respect to each other, and separated by a short replaceable segment of DNA. Digestion with BstXI followed by removal of the replaceable segment yielded a vector molecule capable of ligating to fragments having the same ends as the replaceable segment, but not to itself. In parallel, cDNA synthetic oligonucleotides were employed that give the same termini as the replaceable segment. The cDNA then could not ligate to itself, but could ligate to the vector. In this way, both cDNA and vector were used as efficiently as possible.

Tailing with terminal transferase achieves the same end, but with less convenience and less overall efficiency. Moreover, homopolymer tracts located 5' to cDNA inserts have been reported to inhibit expression in vitro and in vivo (Yokota, T., et al., Nucl. Acids Res. 14:1511–1524 (1986); Riedel, H., EMBO J. 3:1477–1483 (1985)). Similar approaches based on the use of partially filled restriction sites to favor insertion of genomic DNAs (Zabarovsky, E. R., et al., Gene 42:119–123 (1986)) and cDNAs (Yang, Y., et al., Cell 47:3–10 (1986)) recently have been reported. These approaches give 2 or 3 base complementary termini, which usually ligate less efficiently than the 4 base extensions reported here.

Although the cloning scheme of the present invention does not result in a directional insertion of the cDNA, the ability to make large libraries easily, coupled with a powerful selection procedure, makes directional insertion unnecessary. The library construction efficiencies observed according to the present invention, between 0.5 and $2 \times 10^6$ recombinants per μg of mRNA, with less than 1% background and an insert size greater than 1 kb, compared favorably with those described for phage vectors lambda gt10 ($7.5 \times 10^5$/μg of mRNA) and lambda gt11 ($1.5 \times 10^6$/μg of mRNA) (Huynh, T., et al., In: DNA Cloning Vol. I, A Practical Approach, Glover, D. M. (ed.), IRL Press, Oxford (1985), pp. 49–78); but the resulting clones were more convenient to manipulate.

Surface antigen cDNAs can be isolated from these libraries using the antibody enrichment method of the present invention. In this method, the library is introduced into COS cells (for example, by spheroplast or protoplast fusion), where it replicates and expresses its inserts. The cells are harvested by detaching without trypsin, treated with monoclonal antibodies specific for the surface antigens desired, and distributed in dishes coated with affinity purified antibody to mouse immunoglobulins. Cells expressing surface antigen adhere, and the remaining cells can be washed away. From the adherent cells, a Hirt fraction is prepared (Hirt, B., J. Molec. Biol. 26:365–369 (1967)), and the resulting DNA transformed back into E. coli for further rounds of fusion and selection. Typically, after two rounds of selection with monoclonal antibodies recognizing different surface antigens, a single round of selection is performed with a single antibody, or pool of antibodies recognizing the same antigen.

Isolation of a CD28 cDNA

The CD28 cDNA was isolated from a library of about $3 \times 10^5$ recombinants prepared from cDNA from 0.8 μg of poly A$^+$ RNA using an earlier version of the protocol described in the Materials and Methods. The library was screened for CD28 (and other surface antigen) cDNA clones by the method outlined above. After the third transfection, COS cells were panned with the 9.3 antibody alone. A Hirt supernatant was prepared from the adherent cells and transformed into E. coli. Plasmid DNA was isolated from eight colonies and transfected individually into COS cell cultures. The presence of the CD28 antigen was detected in three of eight transfected cultures by indirect immunofluorescence. All three plasmid DNAs contained an insert of about 1.5 kb.

cDNA sequence analysis

The CD28 cDNA encodes a long open reading frame of 220 residues having the typical features of an integral membrane protein (FIGS. 7A–7B). Removal of a predicted (von Heijne, Nucl. Acids Res. 14:4683–4690 (1986)) N-terminal signal sequence gives a mature protein of 202 residues comprising an extracellular domain with five potential N-linked glycosylation sites (Asn-X-Ser/Thr), a 27-amino acid hydrophobic membrane spanning domain, and a 41-amino acid cytoplasmic domain. Comparison of the amino acid sequence of CD28 with the National Biomedical Research Foundation database (Version 10.0) revealed substantial homology with mouse and rabbit immunoglobulin heavychain variable regions over a domain spanning almost the entire extracellular portion of CD28. Within this domain two cysteine residues in the homology blocks Leu-(Ser or Thr)-Cys and Tyr-(Tyr or Phe)-Cys are shared by CD28, CD4, CD8, immunoglobulin heavy- and light-chain variable sequences and related molecules with approximately the same spacing (Maddon et al., Annu. Rev. Biochem. 48:961–997 (1979)).

CD28 cDNA directs the production of a homodimer in transfected COS cells

Immunoprecipitation of CD28 antigen from transfected COS cells was carried out using the monoclonal antibody 9.3 (Hansen, J. A., et al., *Immunogenetics* 10:247–260 (1980)). The material obtained from COS cells migrated with a molecular weight of 74 kd under nonreducing conditions and 39 kd under reducing conditions, a pattern consistent with homodimer formation. Under the same conditions activated T cells give bands with molecular weights of 87 and 44 kd, and HPB-ALL cells give bands of 92 and 50 kd, under nonreducing and reducing conditions respectively. The variation in molecular weight of the material obtained from different cell types arises as a result of differing glycosylation patterns characteristic of each type. Similar results were observed with other leukocyte surface antigens (Seed et al., *Proc. Natl. Acad. Sci USA* 87 (1987)). The nucleotide sequence of the CD28 cDNA predicts a mature protein with molecule weight of 23 kd, much smaller than observed in these experiments, and probably attributable to utilization of the 5 N-linked glycosylation sites predicted by the amino acid sequence.

RNA blot analysis

Equal amounts of total RNA prepared from cell types expressing or lacking CD28 were subjected to RNA blot analysis as described hereinabove. Four bands with molecular weights of 3.7, 3.5, 1.5, and 1.3 kb were visible in lanes containing RNA thymocytes, T blasts, senescent T cells, and the T cell leukemia cell lines PEER and HPB-ALL. No bands were detected in lanes containing RNA prepared from the cell lines U937 (histiocytic leukemia), HuT-78 (Adult T cell leukemia), Jurkat (T cell leukemia), Namalwa (Burkitt lymphoma), MOLT4, and HSB-2, all of which do not express CD28. The 1.5 kb transcript presumably corresponds to the isolated cDNA, and the 3.7 and 3.5 kb species reflect incomplete splicing or alternative polyadenylation site utilization. The 1.3 kb transcript may terminate at an unconventional polyadenylation signal, since there is no obvious candidate in the sequence.

The CD28 gene is not rearranged

DNA blot analysis (Seed et al., *Proc. Natl. Acad. Sci USA* 87 (1987)) of genomic DNA from placenta, peripheral blood lymphocytes, T cells, HeLa cells, or the tumor lines used in the RNA blot analysis above showed identical Dra 1 digest patterns indicating that rearrangement is not involved in the normal expression of the CD28 gene during development. Similarly, no gross genomic rearrangement underlies the failure of the examined T-cell tumor lines to express CD28 antigen. It may be inferred from the Dra 1 fragment pattern that the CD28 gene contains at least two introns.

EXAMPLE IV

Isolation and Molecular Cloning of Two Human CD7 Antigen cDNAs

The CD7 cluster of antibodies (Palker, et al., *Leukocyte Typing II,* Springer-verlag, New York, 303–313 (1985)) recognized a 40 kd glycoprotein (gp40) on the surface of peripheral blood T cells and thymocytes. Early studies with anti-CD7+ antibodies showed that CD7+T cells enhance immunoglobulin (Ig) synthesis by B cells (Miroshima et al., *J. Immunol.* 129:1091–1098 1982)), suppress B cell Ig synthesis when stimulated with Concanavalin A (Haynes et al., *Proc. Natl. Acad. Sci. U.S.A.* 76:5829–5833 (1979)) and are the precursors of the cytotoxic T cells generated in mixed lymphocytic culture (Morishima et al., *J. Immunol.* 129:1091–1098 (1982)). Furthermore, CD7 has been found to be the most reliable marker for the identification of T cell acute lymphoblastic leukemia (Link et al., *Blood* 62:722–728 (1983)). As such, studies have been carried out, in which cytotoxins coupled to the anti-CD7 antibody 3A1 were used to purge bone marrow prior to reinfusion to avoid early relapse in autologous bone marrow transplants or as prophylaxis against graft vs. host disease in allogenic bone marrow transplants (Ramakrishnan et al., *J. Immuol.* 135:3616–3622 (1985)). Similarly, anti-CD7 antibodies also show promise as immunosuppressive agents in the treatment of allograft rejections (Raftery et al., *Transpl. Proc.* 17:2737–2739 (1985)) which is in accord with the recent observation that the anti-CD7 antibody 7G5 significantly inhibits the primary mixed lymphocyte reaction (Lazarovits et al., *Leukocyte Typing III.* Oxford Univ. Press, Oxford (1987)).

At present the physiological role of CD7 is not understood. It is known that anti-CD7 antibodies are not mitogenic, and do not block the T cells' response to PHA, or tetanus toxoid (Palker et al., *Leukocyte Typing,* Springer-Verlag, New York, 303–313 (1985)). Some have noted that expression of CD7 in thymocytes occurs prior to the onset of T cell receptor beta-chain rearrangement (Pittaluga et al., *Blood* 68:134–139 (1986)) and have pointed to a possible role for CD7 in this rearrangement and subsequent expression of the T cell receptor. It is clear that the cloning of the CD7 antigen would further efforts to understand its role in T cell physiology. Nucleotide sequencing and preliminary characterization of two cDNAs encoding the CD7 antigen was carried out according to the method of the present invention. Prompted by the recent suggestion that CD7 may be, or be part of, the T cell IgM receptor (Sandrin et al., *Leukocyte Typing III.* Oxford Univ. Press, Oxford (1987)), the ability of COS cells expressing CD7 to bind IgM or IgM immune complexes was evaluated. The results do not support the simple notion that CD7 itself is an IgM receptor.

Preparation of cDNA library and recovery and characterization of CD7 clones

Preparation of an HPB-ALL cDNA library in the expression vector piH3 was carried out as described herein. Panning of the library was carried out according to the method of the present invention, using purified anti-CD7 antibody Leu9 (Becton Dickinson) and antibody 7G5 as ascites fluid was diluted 1/1000. Methods for cell transfection, radioimmunoprecipitation, DNA and RNA blot hybridization and DNA sequencing were all as described herein.

IgM and IgG binding by COS cells transfected with CD7 and CDw32

Human IgM, IgG, and IgA antibodies, affinity purified FITC conjugated goat anti-human immunoglobulins antibodies (anti-Ig(G+M+A)), washed and preserved bovine red blood cells, and IgG and IgM fractions of rabbit anti-bovine red blood cell antibodies were purchased from Cooper Biomedical (Malverne, Pa.). COS cells were transfected by the DEAE Dextran method with cDNAs encoding the CD7, CDw32, and CD28 surface antigens. 48 hours after transfection the cells were washed with PBS/0.5% BSA and incubated with either human IgM, IgG or IgA antibodies at a concentration of 1 µg/ml, at 4° C. for 2 hours. Subsequently the cells were washed with PBS/0.5% BSA and incubated for 30 minutes at 4° C. with FITC conjugated rabbit anti-human immunoglobulins. After washing the cells were examined with a fluorescence microscope. The experiments were also performed in the presence of 0.1% azide with the same results.

Bovine erythrocytes for rosette assays were prepared as described by Ercolani et al., *J. Immunol.* 127:2044–2051

(1981). Briefly, a 2% suspension of bovine erythrocytes was washed with PBS/0.5% BSA and treated with subagglutinating amounts of either IgG or the IgM fraction of rabbit anti-bovine erythrocyte antibodies at 4° C. for 1 hour. Erythrocytes were then washed twice with PBS/0.5 BSA and adjusted to a 2% solution. 2 ml of antibody-coated erythrocytes were layered on 60 mm dishes containing COS cells which had been transfected 48 hours earlier with either CD7, CD32 or CD28 by the DEAE Dextran method. The dishes were then centrifuged at 150×g at 4° C. for 15 minutes. After an additional 45 minute incubation at 4° C., the plates were gently washed 5 times with 5 mls of PBS/0.50 BSA, and the COS cells were examined for rosette formation. These experiments were also performed in the presence of 0.1% sodium azide without alteration of the results.

Formation of T cell rosettes with antibody-coated erythrocytes

Peripheral blood lymphocytes were obtained from heparinized blood by centrifugation at 4° C. over a Ficoll-Hypaque gradient at 400×g for 30 minutes. Leukocytes at the interface were washed two times with PBS. The leukocytes were adjusted to 10Y7 cells/ml in IMDM/10% Fetal Bovine Serum (FBS) and incubated in tissue culture dishes at 37° C. for 30 minutes. Nonadherent cells were transferred to new dishes, and PHA was added to stimulate proliferation of T lymphocytes. On the next day the cells were washed with PBS and placed in fresh IMDM/10% FBS.

Rosette assays were performed three days later. Cells were washed with PBS/0.5% BSA, and a 10 ul suspension of 2% Ig-coated erythrocytes prepared as described above was added to 10 ul of PBS/0.5% BSA containing 5×10$^6$ cells/ml. The mixtures were placed in Falcon round bottom 96 well plates and centrifuged at 150×g for 15 min at 4° C. After an additional incubation of 45 min at 4° C. pellets were resuspended with 10 ul of PBS/0.5% BSA, and the rosettes scored by phase contrast microscopy. The experiments were carried out in both the presence and absence of 0.1% sodium azide with no detectable difference.

Isolation of cDNAs encoding the human CD7 antigen

To isolate CD7 cDNAs, a large plasmid library was constructed in the expression vector piH3M as describe hereinabove. The library was introduced into COS cells by spheroplast fusion, and allowed to replicate and express its inserts. The COS cells were harvested by detaching without trypsin 48 to 72 hours after transfection, treated with monoclonal antibodies specific for surface antigens believed to be encoded in the library, and distributed in dishes coated with affinity purified anti-mouse antibody as described herein. Under these conditions, cells expressing surface antigen adhere and the remaining cells can be washed way.

A Hirt (Hirt, *J. Mol. Biol.* 26:365–369 (1967)) fraction was prepared from adherent cells, and the resulting DNA transformed back into *E. coli* for further rounds of fusion and selection. In the third round of selection the detached cells were treated with a mixture of monoclonal antibodies specific for CD7 (765 and Leu9), and a Hirt supernatant was again generated and transformed into *E. coli*. After transformation of the DNA into *E. coli* 8 colonies were picked, and the plasmid DNA prepared from them by an alkaline miniprep procedure (Maniatis, et al., *Molecular Cloning: A Laboratory Manual*, Cold Spring Harbor Press, Cold Spring Harbor, N.Y. (1982)). DNA was prepared from 8 resulting colonies and transfected into COS cells. After 3 days, surface expression of the CD7 antigen was detected by indirect immunofluorescence in 7 of 8 transfected dishes. Restriction enzyme digest of the corresponding plasmid DNAs revealed two species. One contained a 1.2 kb insert, and the other a 1.3 kb insert.

CD7 cDNA sequence analysis

Both isolates were sequenced by the dideoxynucleotide method. The 1.2 kb cDNA encodes a long open reading frame of 240 residues having the typical features of an integral membrane protein. The initial assignment of the signal sequence cleavage site by the method of von Heijne (*Nucl. Acids Res.* 14:4683–4690 (1986)) was at the 18th residue. It later was determined, however, that the homology with immunoglobulin variable regions would better predict the mature terminus at residue 26; this assignment would also correlate well with the position of the intron as discussed below and as shown in FIG. 8. Removal of the predicted N-terminal signal sequence gives a mature protein of 215 residues with a predicted molecular mass of 23 kd. In the extracellular domain are two N-linked glycosylation sites (Asn-X-Ser Thr), in agreement with the results of Sutherland et al. (*J. Immunol.* 133:327–333 (1984)), who also showed the presence of O-linked glycans and covalently associated palmitic acid on the mature protein. In the 27 amino acid hydrophobic membrane spanning domain is a single cysteine residue which may be the site of fatty acylation (Rose et al., *Proc. Natl. Acad. Sci. USA* 81:2050–2054 (1984); Kaufman et al., *J. Biol. Chem.* 259:7230–7238 (1984)). The length of the cytoplasmic domain, 39 residues, is in good agreement with the 30–40 amino acids predicted by protease digestion of the CD7 precursor in rough microsomal membrane fractions (Sutherland et al., *J. Immunol.* 133:327–333 (1984)).

Sequence analysis of the 1.7 kb clone (FIG. 8) revealed the presence of an intron located 121 bp from the 5' end. The 411 bp intron contains stop codons in all three reading frames and is located just downstream of the secretory signal sequence, as is frequently observed for secreted or surface proteins. Both the 5' and 3' ends of the intron conform to the splice donor/acceptor consensus AAG GTRAGA/ . . . /Y$_{6-11}$NYAG A (Mount, *Nucl. Acids Res.* 10:459–472 (1982)). Because both the 1.2 and 1.7 kb clones express CD7 antigen equally well in COS cells, the intron must be excised in COS cells fairly efficiently.

Comparison of the amino acid sequence with the National Biomedical Research Foundation database revealed substantial homology with human and mouse immunoglobulin kappa chain and T-cell receptor gamma chain variable regions over almost the entire extracellular portion of the molecule. Two cysteine residues shared in approximately equal spacing by all three structures fall in the conserved sequences Ile-Thr-Cys and Tyr-X-Cys. In kappa chain variable regions these cysteines form a disulfide bridge. The presence of at least one intrastrand disulfide bond in the CD7 structure has previously been proposed by Sutherland et al. (*J. Immunol.* 133:327–333 (1984) ), who noted that immunoprecipitation of CD7 gave rise to a band with an apparent molecular mass of 40 kd under reducing conditions and 38 kd under nonreducing conditions.

Based on the homology with immunoglobulin V-regions, it is predicted that CD7 contains a disulfide bond linking Cys 23 and Cys 89. A second disulfide bond, linking Cys 10 and Cys 117, has been proposed, based on the structural similarity between CD7 and Thy-1. The extracellular domains of both Thy-1 and CD7 have 4 cysteine residues, in roughly homologous positions. The 4 cysteine residues of Thy-1 are joined in two internal disulfide bridges between Cys 9–111 and Cys 19–85 (Williams et al., *Science* 216:696–703 (1982)). In Thy-1, Cys 111 forms an amide bond with the ethanolamine moiety of a substituted phosphatidylinositol, and is thus the last residue of the mature molecule (Tse et al., *Science* 230:1003–1008 (985) ). In CD7, Cys 117 is followed by four repeats of a sequence whose consensus is Xaa-Pro-Pro-Xaa-Ala-Ser-Ala-Leu-Pro, and which, it is proposed, plays the role of a stalk projecting the V-like domain away from the surface of the cell.

In addition to the homologies shown in FIG. 20 and mentioned above, the extracellular domain of CD7 has significant homology with both chains of the rat CD8 heterodimer (Johnson et al., *Nature* 323:74–76 (1986)), and the myelin $P_0$ protein (Lemke et al., *Cell* 40:501–508 (1985)).

CD7 directs the production of a 40 kd protein in transfected COS cells

Immunoprecipitation of CD7 antigen from transfected COS cells was carried out as described herein using monoclonal antibody 7G5 (Lazarovits et al., *Leukocyte Typing III*, Oxford Univ. Press, publisher, Oxford, England (1987). The material obtained from COS cells migrated with as a broad band with molecular weight of 40 kd under reducing conditions. Under the same conditions HPB-ALL cells (the cDNA donor line) and activated T cells gave bands with molecular widths of 41 and 39 kd respectively. In both the COS cell and HPB-ALL lane a faint band with molecular weight of 30 kd was also observed, possibly corresponding to a partially glycosylated precursor (Sutherland, D. R., et al., *J. Immunol.* 133:327–333 (1984)).

RNA blot analysis

Equal amounts of total RNA prepared from cell types expressing or lacking CD7 were subjected to Northern blot analysis as described herein. A single 1.3 kb species was visible in lanes containing RNA from thymocytes, activated T cells, resting T cells, and the T cell leukemia lines HuT-78, HPB-ALL, Jurkat J3R7, HSB-2 and PEER. With the exception of the PEER cell line, none of the T cell tumors showed significant overexpression of CD7 transcripts. CD7 RNA was detected in all of the thymus-derived cells, but not in RNA from U937 (histiocytic leukemia) and Namalwa (Burkitt Lymphoma) cells. No band corresponding to the 1.7 kb cDNA could be detected, suggesting that this species is artificially enriched during the cloning or library amplification process.

Enrichment during amplification seems unlikely because the 12 kb cDNA clone propagates as well in *E. coli* as the 1.7 kb clone. However, immediately upstream and downstream from the site of insertion of the intron are sequences that could form an interrupted stem and loop structure. Eight of the 10 basepairs of the potential stem are GC pairs, perhaps giving the structure sufficient stability to interfere with elongation of the cDNA first strand. The presence of the intron greatly separates the two halves of the stem, potentially eliminating the structure via unfavorable loop entropy and allowing efficient first strand synthesis.

The CD7 gene is not rearranged

Southern blot analysis of genomic DNA from placenta, peripheral blood lymphocytes, T cells, HeLa cells, or the tumor lines used in the RNA blot analysis above showed identical Dra 1 digest patterns. Thus, the CD7 gene is not grossly altered during development, and the high level of expression in the PEER cell line is not the consequence of a substantial genomic rearrangement.

COS cells expressing CD7 do not bind IgM

Human peripheral blood T lymphocytes express receptors for IgM antibodies (FcRu: Moretta et al., *Eur. J. Immunol.* 5:565–569 (1975); McConnell et al., *Immunol.* 30:835–837 (1976)). Recently it has been reported that CD7 might play a role in IgM binding by T cells (Sandrin et al., *Leukocyte Typing III*, Oxford Univ. Press, publisher, Oxford, England (1987)). L cells, normally $CD7^-$ and $FcRu^-$, become $CD7^+$ and $FcRu^+$ when transfected with a 16 kb genomic fragment encoding the CD7 antigen (Sandrin et al., *Leukocyte Typing III*, Oxford Univ. Press, publisher, Oxford, England (1987)). Furthermore, IgM binding to CD7-positive cells can be blocked by the anti-CD7 monoclonal antibody Huly-m2 (Thurlow et al., *Transplantation* 38:143–147 (1984)), and IgM columns bind a 37 kd protein from radiolabeled lysates of peripheral blood T lymphocytes (Sandrin et al., *Leukocyte Typing III*, Oxford Univ. Press, publisher, Oxford, England (1987)).

Accordingly, COS cells expressing CD7 were tested for their ability to bind IgM. IgM receptor activity was assayed either by direct binding (Hardin et al., *Proc. Natl. Acad. Sci. USA* 76:912–914 (1979)) or by a rosette assay with ox erythrocytes coated with an IgM fraction of rabbit anti-bovine red cell serum as described by Ercolani et al., *J. Immunol.* 127:2044–2051 (1981)). Cells expressing CD7 neither bound human IgM nor formed rosettes with IgM-coated erythrocytes. Under the same conditions, COS cells transfected with a cDNA encoding the human IgG receptor CDw32 bound IgG directly and formed rosettes with IgG-coated erythrocytes. Erythrocytes coated with IgM or IgG antibodies also adhered to a fraction of peripheral blood lymphocytes as reported (Moretta et al., *Eur. J. Immunol.* 5:565–569 (1975)).

These results do not support the notion that the CD7 antigen is by itself an IgM receptor, although they do not exclude the possibility that COS cells suppress IgM binding activity in some manner, or that CD7 is part of, or modified to become, an IgM receptor. That CD7 is not by itself an IgM receptor is supported by the observation that a number of $CD7^+$ T cell lines are FcRu-(Sandrin et al., *Leukocyte Typing III*, Oxford Univ. Press, publisher, Oxford, England (1987)).

EXAMPLE V

Isolation and Molecular Cloning of the Human CDw32 Antigen

A cDNA encoding the human CDw32 antigen, a human receptor for immunoglobulin G constant domains (Fc receptor), was isolated by the method of the present invention, by virtue of its affinity for its ligand, IgG. The sequence of the isolated clone is most closely related to the murine beta 2 Fc receptor, but has diverged completely in the portion encoding the cytoplasmic domain. The receptor expressed in COS cells shows a preference for $IgG_1$ among IgG subtypes, and no affinity for IgM, IgA or IgE.

To isolate the Fc receptor clone, cDNA libraries were prepared from tumor cell lines or from a human tumor and transfected into COS cells. After 48 hours, the cells were treated with mouse or human IgG antibodies, and allowed to settle on dishes coated with affinity-purified sheep anti-mouse IgG or goat anti-human IgG antibodies. After lysis, DNA recovery, and transformation in *E. coli*, the cycle was repeated for two more rounds. Although no positive clones were isolated from the tumor line libraries, a cDNA clone encoding an Fc receptor was isolated from a library prepared from a human adrenal tumor. It has been discovered that many tumors are heavily infiltrated by macrophages and lymphocytes. Thus, tumor RNA may be a productive source in general for transcripts of human macrophages.

By indirect immunofluorescence assay, the human receptor expressed on COS cells bound all mouse and human IgGs with relatively low affinity $-10^{-7}M$), and a clear discrimination was noted among human antibodies for $IgG_1$. Human IgM, $IgA_1$, $IgA_2$, and IgE did not bind, nor did murine IgM or IgA. As expected, human Fc, but not Fab fragments, bound to the transfected cells. Among monoclonal antibodies donated to the Third International Workshop on Leukocyte Differentiation Antigens, three gave strong positive immunofluorescence: two (out of two) recognizing the Fc Receptor CDw32 determinant, and one (out of four) recognizing the CD23 (B cell IgE Fc receptor) determinant. Monoclonals recognizing the T cell/ Macrophage Fc receptor antigen CD16 gave only weak immunofluorescence comparable to that shown by control ascites.

Radioimmunoprecipitation of transfected COS cells with CDw32 antibodies showed the presence of a single 40 kd species, comparable in size to the antigen recognized on the surface of the myeloid CDw32$^+$ line HL-60, and to the less abundant antigen present on the histiocytic leukemia line U937. This result reinforces the notion that the isolated receptor is CDw32, as the CD16 receptor is reported to be substantially larger (60–70 kd).

The nucleotide sequence of the isolated receptor (FIGS. 9A–9B) is highly homologous to that of members of the recently isolated murine receptor family, and most closely related to the murine beta$_2$ receptor by nucleic acid homology. Surprisingly, the murine beta$_2$ receptor is found on T and B lymphocytes and macrophages, while the alpha receptor is restricted to macrophages; in the human system, CDw32 (shown here to be beta$_2$-like) is restricted to macrophages while another Fc receptor (CD16) is found on lymphocytes and macrophages. The human sequence appears to have diverged from the mouse sequence by insertion of approximately 1 kb of DNA a few bases 3' to the junction between the transmembrane and cytoplasmic domains. The junctions of the insertion site do not show obvious relationships to splice donor and acceptor sequences. Comparison of the human and murine peptide sequences showed that the peptide sequence diverges at the end of the transmembrane domain, before the nucleotide sequence diverges, suggesting the existence of a selective pressure favoring the creation of a differenct cytoplasmic domain.

RNA blot analysis showed that myeloid but not lymphocytic cell lines expressed RNA homologous to the CDw32 probe. DNA blot analysis showed multiple bands consistent with the existence of a small multigene family.

EXAMPLE VI

Isolation and Molecular Cloning of Two cDNA Clones Encoding the B Lymphocyte-specific CD20 (B1, Bp35) Antigen Recent studies suggest that the pan B cell antigen CD20 (B1, Bp35) plays an important role in B cell activation. Monoclonal antibodies (mAb) to CD20 induce different cellular responses depending on the antibody used and the stage of differentiation or activation of the target B cells. The monoclonal antibody 1F5 activates resting B cells by initiating the transition from the G$_0$ to the G$_1$ phase of the cell cycle, and induces dense tonsillar B cells to proliferate (Clark et al., *Proc. Natl. Acad. Sci USA* 82:1766 (1985); Clark and Shu, *J. Immunol.* 138:720 (1987)). However, 1F5 does not induce an increase in cytoplasmic free calcium and does not induce circulating B cells to proliferate (Rabinovitch et al, In: *Leukocyte Typing III* (McMichael, Ed.), p. 435, Oxford University Press (1987)). Other anti-CD20 mAbs, such as B1, have been shown to block B cell activation (Tedder et al., *J. Immunol.* 135:973 (1985)) and both 1F5 and B1 can inhibit B cell differentiation (Golay et al., *J. Immunol.* 135:3795 (1985)). Recently it has been suggested that phosphorylation and internalization of CD20 may be necessary steps for B cell entry into the G$_1$ phase of the cell cycle (Valentine et al., In: *Leukocyte Typing III* (McMichael, Ed.), p. 440, Oxford University Press (1987)). In the present example, two CD20 cDNA clones were isolated and expressed using the methods of the present invention.

Preparation of cDNA Library and Recovery of cDNA Clones by Panning

Poly(A)$^+$ RNA was prepared from the human Burkitt cell line Daudi by oligo (dT) cellulose chromatography of total RNA isolated by procedures described herein. cDNA preparation and expression library construction were carried out as described.

Anti CD20 mAbs 1F5, 2H7, B1, L27, G28-2, 93-1B3, B-C1, and NU-B2 were obtained from the International Leukocyte Typing Workshop (Valentine et al., In: *Leukocyte Typing III* (McMichael, Ed.), p. 440, Oxford University Press (1987)). Purified mAbs were used at a concentration of 1 ug/ml and ascites were used at a dilution of 1:1000. Panning was done according to the present method. In the first round of screening, eight 10 cm dishes of 50% confluent COS cells were transfected by the DEAE-Dextran method. Subsequent screening cycles were performed by spheroplast fusion.

Immunoprecipitation, Sequencing, RNA and DNA Blot Hybridization

B cell lines CESS and Daudi were metabolically labeled with $^{35}$S-methionine and $^{35}$S-cysteine for 6 h at 37° C. COS cells transfected by the DEAE-Dextran method were similarly labeled 36 hours post-transfection. The labeled cells were incubated with the B1 mAb (Coulter) at 4° C. for 1 h, washed in PBS, and lysed with 0.5% NP-40, 0.1% SDS, 0.05% deoxycholate and 1 mM PMSF in PBS. After centrifuging (13000×g, 5 min.), the lysate was incubated with fixed *S. aureus* cells (Calbiochem) for 1 hr at 4° C. The *S. aureus* cells were pelleted, washed 5 times with 1% NP-40/ PBS, eluted and electrophoresed through 12.5% polyacrylamide gels.

DNA and RNA blot analysis and hybridization probe preparation were carried out as described. Sequencing was done by the method of Sanger et al., *Proc. Natl. Acad. Sci. USA* 74:5463 (1977)). The nucleotide sequence of the CD20.4 cDNA is represented in FIGS. 10A–10B.

Two cDNA clones, bearing inserts of 1.5 (CD20.4) and 1.0 kb (CD20.6), were isolated from a Daudi cell DNA library by panning with a panel of mAbs against CD20. COS cells transfected with either clone reacted with all members of the panel of antibodies. Immunoprecipitation of the cDNA-enclded protein from transfected COS cells showed two bands of 32 and 30 kd reminiscent of the 37 and 35 kd bands observed in different B cell subsets and lines (Valentine et al., "Structure and Function of the B Cell Specific 35–37 kDa CD20 Protein," In: *Leukocyte Typing III*, A. McMichael et al., eds., Oxford University Press, p. 440 (1987)). It has been the experience of the present inventors that the molecular masses of surface antigens expressed in COS cells are consistently smaller than those of their native counterparts. This may be due to differences in glycosylation.

Both cDNA clones have the same coding sequence, and differ only in the 3' untranslated region. The insert in clone CD20.6 has a short polyA tail and lacks a consensus polyadenylation signal, while the insert in CD20.4 lacks a polyA tail and extends 431 bp beyond the 3' terminus in CD20.6 (FIGS. 10A–10B).

RNA blot analysis showed that three transcripts of 3.8, 3.0 and 1.5 kb were present in B cells but absent from other cell types, in agreement with the known pattern of antibody reactivity (Clark et al., *Proc. Natl. Acad. Sci. USA* 82:1766 (1985); Clark et al, *J. Immunol.* 138:720 (1987); Tedder et al., *J. Immunol.* 135:973 (1985); Golay et al., *J. Immunol.* 135:3795 (1985)). It appears likely that the CD20.6 clone is derived from the 1.5 kb transcript or possibly from an even shorter, undetectable species. Because the CD20.4 clone lacks a poly(A)⁺ tail, its source cannot be inferred at present.

DNA blot analysis showed that the CD20 genomic sequences are not rearranged during development and are not amplified in the cell lines examined. A restriction fragment length polymorphism was observed in a DNA sample obtained from placenta.

Figure 10C:
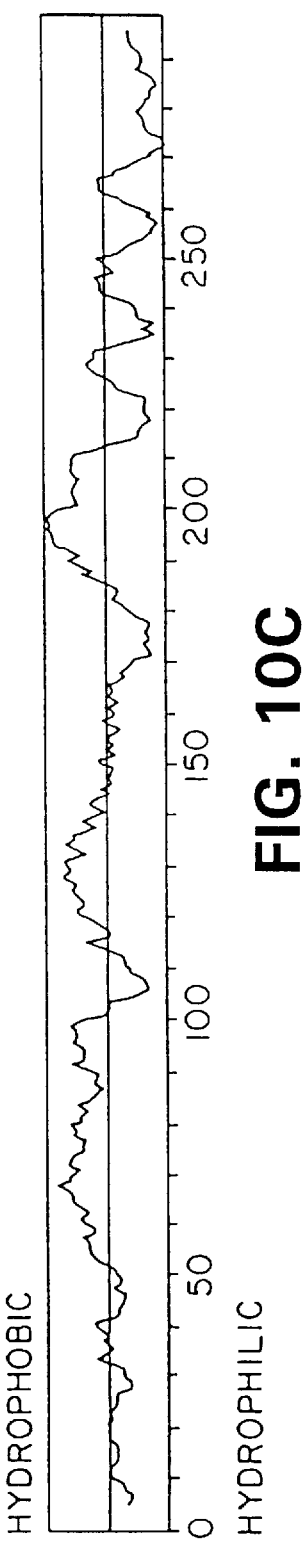
FIGS. 10A–10B.

The amino acid sequence predicted by the cDNA contains 297 residues and has a molecular mass of 33,097 daltons. The sequence contains three major hydrophobic stretches involving residues 51–103, 117–141 and 183–203 (FIG. 10C). Two other notable characteristics are the absence of an amino-terminal signal peptide and the presence of a highly charged carboxy-terminal domain. A polyclonal anti-CD20 antibody that recognized the last 18 residues of the carboxy-terminus reacts with lysates of cells expressing CD20 but not with intact cells, suggesting that the CD20 carboxy terminus is located within the cytoplasm. Since there is no amino-terminal signal peptide, it is likely that the amino-terminus is also intracellular, and that the first hydrophobic region acts as an internal membrane insertion signal (Zerial et al., *EMBO J.* 5:1543 (1986)). The first hydrophobic region is composed of 53 residues and is therefore long enough to span the membrane twice if organized as an alpha helix. Because there are two remaining hydrophobic regions, the intracellular localization of the carboxy-terminus requires that the first hydrophobic domain exit the membrane on the side. Alternatively, the carboxy-terminal antibody may only recognize epitopes exposed by detergent treatment allowing the carboxy-terminus to be extracellular and forcing the first hydrophobic domain to exit the membrane on the extracellular side. The sequence contains 2 potential N-glycosylation sites (Asn-Xaa-Ser/Thr, where Xaa cannot be Pro (Bause, *Biochem. J.* 209:331 (1983)) at positions 9 and 293, but neither of these is expected to be used if located in intracellular domains of the molecule. The difference in molecular mass between CD20 expressed on COS cells and on B cells is therefore presumably due to O-linked glycosylation, although other forms of post-translational modification are not excluded. If the carboxy-terminus is intracellular, the only extracellular domain would lie between residues 142 and 182. This region is rich in serine and threonine residues which might support O-glycosylation.

The observation of two protein species in COS cells cannot be explained by alternate splice formation because the cDNA sequence does not contain any promising splice donor or acceptor sequences (Shapiro et al., *Nucl. Acids Res.* 15:7155 (1987)). A difference in glycosylation or alternate translational initiation site selection may account for the two species observed. Initiation at either the first or the second ATG gives protein molecular masses of 33.1 and 30.8 kd respectively, in good agreement with the sizes observed in COS cells. Neither ATG is embedded in the consensus sequence proposed by Kozak (*Nucl. Acids Res.* 12:857 (1984)). Use of alternate initiation sites has been reported for several proteins (Kozak, *Nucl. Acids Res.* 12:857 (1984)).

Comparison of the peptide sequence with the sequences in the National Biomedical Research Foundation database showed no significant homology by the FASTP rapid sequence alignment algorithm. Because the bulk of the protein appears to be confined to the interior of the membrane and the cell, it seems plausible that it may play a role in transducing signals from other transmembrane proteins to the cell interior. Consistent with this role is the relatively hydrophilic nature of the hydrophobic regions which might allow hydrogen bond interactions with the transmembrane portions of other proteins.

EXAMPLE VII

Isolation and Molecular Cloning of ICAM, An Adhesion Ligand of LFA-1

Antigen-specific cell contacts in the immune system are strengthened by antigen-non-specific interactions mediated in part by lymphocyte function associated or LFA antigens (Springer, T. A., et al., *Annu. Rev. Immunol.* 5:223–252 (1987); Anderson, D. C., et al., *Annu. Rev. Medicine* 5:175–194 (1987)). The LFA-1 antigen, a major receptor of T cells, B cells and granulocytes (Rothlein, R., et al., *Exp. Med.* 163:1132–1149 (1987)), is involved in cytolytic conjugate formation, antibody-dependent killing by NK cells and granulogytes, and helper T cell interactions. LFA-1 has been placed in the integrin family of cell surface receptors by virtue of the high sequence similarity between the LFA-1 and integrin beta chains (Kishimoto, T. K., et al., *Cell* 48:681–690 (1987); Hynes, R. O. *Cell* 48:549–554 (1987)). The adhesion ligands of the integrin family are glycoproteins bearing the Arg-Gly-Asp (RGD) sequence motif, e.g., fibronectin, fibrinogen, vitronectin and von Willebrand factor (Ruoslahti, E., et al., *Cell* 44:517–518 (1987)).

In this example, the Intercellular Adhesion Molecule-1 (ICAM-1), a ligand for LFA-1 (Rothlein, R., et al., *J. Immunol.* 137:1270–1275 (1986); Dustin, M. L., et al., *J. Immunol.* 137:245–254 (1986)), was cloned according to the methods of the present invention. ICAM contains no RGD motifs, and instead is homologous to the neural cell adhesion molecule NCAM (Cunningham, B. A., et al. *Science* 236:799–806 (1987); Barthels, D., et al., *EMBO J.* 6:907–914 (1987)). COS cells transfected with the ICAM cDNA clone bind myeloid cells by a specific interaction which can be blocked by monoclonal antibodies directed against either LFA-1 or ICAM-1.

A cDNA library was constructed using RNA prepared from HL60 cells induced with phorbol myristyl acetate (PMA). The library was transfected into COS cells and cells expressing surface antigens were recovered according to the methods of the present invention by panning with the anti-ICAM monoclonal antibodies (mAbs) 8F5 and 84H10 (McMichael, A. J., et al., eds., *Leukocyte Typing III. White Cell Differentiation Antigens,* Oxford University Press (1987)). Episomal DNA was recovered from the panned cells and the expression-panning cycle repeated a further 2 times to obtain a cDNA clone designated pICAM-1.

COS cells transfected with pICAM-1 gave positive surface immunofluorescence reactions with three anti-ICAM-1 antibodies: 8F5; 84H10; and RR-1. Immunoprecipitation of pICAM-1-transfected COS cells with the mAb 84H10 gave a band of molecular mass 100 kd. 30). A slightly larger protein of 110 kd was precipitated from HL60 cells induced for 48 hours with either phorbol myristyl acetate (PMA), gamma-interferon (gammaIFN), tumour necrosis factor (TNF), or interleukin-1 beta (IL-1 beta), but was absent from uninduced cells. The smaller molecular mass of ICAM-1 expressed in COS cells is consistent with the lower molecular masses observed for other surface antigens expressed in COS cells.

RNA blot analysis showed 2 species of 3.2 kb and 1.9 kb present in HL60 cells stimulated with either PMA, gamma IFN, TNF or IL-1 gamma, but absent in uninduced cells. Thus, the expression of ICAM-1 is regulated by a number of cytokines, apparently at the level of transcription. Similar species were present in B cells (JY and Raji), T cells (Peer and T blasts) and Lymphokine Activated Killer cells (LAK). The structure of these ICAM-1 transcripts and their relationship to the pICAM-1 cDNA remains to be established. Blot hybridization of genomic DNA from placenta revealed a pattern consistent with a single copy gene.

To investigate whether pICAM-1 encodes a functional cell adhesion molecule, COS cells expressing ICAM-1 were tested for their ability to bind HL60 cells. After 30 minutes at 37° C. in the presence of $Mg^{2+}$, HL60 cells strongly adhered to the ICAM-expressing COS cells, but not to mock transfected cells. The specificity of this adhesion was demonstrated by preincubating the ICAM-1 expressing COS cells with mAb 84H10. All HL60 binding was abolished under these conditions. An isotype matched monoclonal antibody, W6/32, which recognizes a monomorphic HLA-ABC related determinant of approximately equal abundance to ICAM-1 on transfected COS cells, had no effect on the adhesion. Similarly, preincubation of the HL60 cells with either 84H10 or W6/32 did not inhibit binding.

To determine if LFA-1 was acting as the receptor for ICAM-1 in this system, HL60 cells were pretreated with antibodies against the beta chain of LFA-1 (CD18 (McMichael, A. J., et al., eds., *Leukocyte Typing III. White Cell Differentiation Antigens*, Oxford University Press (1987))) and then subjected to the binding assay. All adhesion to ICAM-expressing COS cells was blocked. Pretreatment of COS cells with the CD18 antibodies had no effect on the adhesion. This provides direct evidence that ICAM-1 is indeed acting as an adhesion ligand for LFA-1.

The sequence of the pICAM-1 cDNA insert consists of 1846 nucleotides (FIGS. 11A–11C). The predicted peptide sequence of 532 residues has the typical features of a transmembrane protein including a putative signal sequence, which may be cleaved between glycine-25 and asparagine-26 (von Heijne, G., *Nucl. Acids Res.* 14:4683–4690 (1986)), and a single 25 residue membrane-spanning domain terminating in a short, highly charged cytoplasmic domain. The extracellular domain contains seven potential N-linked glycosylation sites which could adequately explain the difference in size between the deglycosylated precursor (55 kd) and the final product (90–115 kd) (Dustin, M. L., et al., *J. Immunol.* 137:245–254 (1986)). Differential use of these putative glycosylation sites could also explain the heterogeneous molecular mass of ICAM-1 observed in different cell types (Dustin, M. L., et al., *J. Immunol.* 137:245–254 (1986)).

LFA-1 is a member of the integrin family of cell surface receptors (Kishimoto, T. K., et al., *Cell* 48:681–690 (1987); Hynes, R. O., *Cell* 48:549–554 (1987)). The tripeptide motif Arg-Gly-Asp (RGD) is a common feature of the ligands for this family, e.g., fibronectin, fibrinogen, vitronectin and von Willebrand factor, and is crucial for ligand-receptor interaction (Ruoslahti, E, et al., *Cell* 44:517–518 (1987)). However, ICAM-1 contains no RGD motifs, bearing instead a single RGE sequence at position 152. A search of the National Biomedical Research Foundation (Dayhoff, M. O., et al., *Methods Enzymol.* 91:524–545 (1983)) (NBRF) database revealed no significant similarities to other proteins. However, a comparison to a laboratory database containing recently published surface proteins did reveal a surprising and significant similarity between ICAM-1 and the neural cell adhesion molecule NCAM-1 (Cunningham, B. A., et al., *Science* 236:799–806 (1987); Barthels, D., et al., *EMBO J.* 6:907–914 (1987)). The optimal alignment score obtained using the NBRF ALIGN program is 8 standard deviations above the mean score obtained from 500 random permutations of the sequences. The probability of the spontaneous occurrence of an equal or higher score is approximately $10^{-9}$.

Using a database of known immunoglobulin related sequences, it has been shown that ICAM-1 may be divided into five Ig domains (28–112, 115–206, 217–310, 312–391, and 399–477) each of which shows significant similarity with other members of the Ig superfamily (Williams, A. F., *Immunol. Today* 8:298–3–3 (1987)). For example, domain I is similar to CD3 while domains IV and V are similar to domains of myelin associated glycoprotein (Arguint, M., et al., *Proc. Natl. Acad. Sci. USA* 84:600–604 (1987)) and carcinoembryonic antigen (Beauchemin, N., et al., *Mol. Cell. Biol.* 7:3221–3230 (1987)). All five Ig domains of NCAM align with the Ig segments in ICAM, and the principal contribution to the similarity comes from domains II and III of ICAM. Finally, the T cell-specific adhesion molecule CD2 shows roughly the same similarity to NCAM as does ICAM, but ICAM and CD2 are only weakly related. Thus, some precursor of NCAM is ancestral to both ICAM and CD2.

Through its cell adhesion to LFA-1, ICAM can mediate migration of lymphocytes into areas of inflammation. Inhibiting such migration by blocking ICAM binding to LFA-1 could reduce or inhibit inflammation. Such inhibition could be affected by small organic molecules, i.e., drugs, identified in an ICAM streaming assay. Fusion proteins composed of the extracellular domain of ICAM and IgG molecules are suitable for identifying such inhibitors. Likewise, compounds that interfere with ICAM binding to Rhinovirus or Plasmodium falciparium can be identified by analogous methods.

The Applicants have constructed fusion proteins consisting of the Ig domains of the ICAM-1 extracellular domain, which are useful in streaming assays. The CH2 and CH3 domains of IgG1 were fused to extracellular Ig domain 1, domains 1 and 2, domains 1–3, domains 1–4, and domains 1–5 of ICAM-1. The corresponding clones have been designated ICAM1-Eγ1, ICAM1-Eγ2, ICAM1-Eγ3, ICAM1-Eγ4 and ICAM1-Eγ5. The first two N-terminal domains (amino acids 28–112 and 115–206, respectively) are believed to be most useful in a binding assay to identify compounds that inhibit ICAM binding to another ligand.

Soluble ICAM can also be used directly to interfere with the binding of cellular ICAM to Rhinovirus or Plasmodium, thereby inhibiting the infection. Soluble ICAM includes the extracellular domain of ICAM, or functional derivatives thereof, in truncated form or fused to a soluble protein such as Ig.

For the purpose of the invention as it relates to ICAM-1 protein, the term "functional derivatives" includes polypeptides that have at least about 80% amino acid identity to the entire disclosed ICAM-1 amino acid sequence, its intracellular domain, its extracellular domain (amino acids 1–477) or any of immunoglobulin domains 1–5 therein, or the sequence comprising the LFA-1 binding site, and that have a binding affinity to a ligand of ICAM-1 such as LFA-1 that is at least about 30% as that of the disclosed sequence. Such polypeptides may optionally be included as part of a larger protein. Increasingly preferred are amino acid identities that increase integrally, i.e., at least about 81%, 82%, 83%, etc.

Binding affinity of ICAM-1 to a ligand such as LFA-1 can be determined by methods known in the art. Increasingly preferred are binding affinities that increase in increments of 10%, i.e., at least about 40%, 50%, etc., of that of the disclosed sequence.

A nucleotide sequence is a "functional derivative" of ICAM-1 if it encodes the diclosed ICAM-1 amino acid sequence or a functional derivative thereof.

In designing functional derivatives of ICAM-1 protein, amino acids or regions known to be important to the binding of ICAM-1 to a ligand such as LFA-1 should be highly conserved. Publications relating to binding of ICAM-1 to LFA-1 include: Hedman, H. & Ludman, E. (1991) J. Immunol. 149:2295–9; Dang, L & Rock, K. (1991) J. Immunol. 146:3273–9; Ross, L et al. (1992) J. Biol.Chem. 267:8537–43; Hibbs, M. et al. (1991) Science 251:1611–3; Berendt, A. et al. (1992) Cell 68:71–81; Ockenhouse, C. et al. (1992) Cell 68:63–9; Diamond, M. et al. (1991) Cell 65:961–71; Cabanas, C. & Hogg, N. (1991) FEBS Lett 292:284–8; and Staunton, D. et al. (1990) Cell 61:243–54 (errata at Cell (1990) 61:1157 and Cell (1991) 667:1312).

Additional publications relating to function of ICAM-1 include: Salkind, A. et al. (1991) J. Clin. Invest. 88:505–11; Fischer, H. et al. (1992) J. Immunol. 148:1993–8; Carlow, D. et al. (1992) J. Immunol. 148:1595–606; Rothlein, R. et al. (1991) J. Immunol. 147:3788; Fine, J. & Kruisbeek, A. (1991) J. Immunol. 147:2852–9; Tang, A. & Udey M. (1991) J. Immunol. 146:3347–55; Symington, F. & Santos, E. (1991) J. Immunol. 146:2169–75; Rosenstein, Y. et al. (1991) Nature 354:233–5; Fujiota, H. et al. (1991) Biochem. Biophys. Res. Commun. 177:664–72; Nambu, M. et al. (1992) Cell Immunol. 143:335–47; Sanders, V. & Vitetta, E. (1991) Cell Immunol. 132:45–55; Diamond, M. et al. (1990) J. Cell Biol. 111:3129–39; Maraskovsky, E. et al. (1992) Int. Immunol. 4:475–85; Padros, M. et al. (1992) Clin. Exp. Immunol. 88:329–34; and Van Seventer, G. et al. (1991) Eur. J. Immunol. 21:1711–18.

In particular, Piela-Smith, T. et al. (1992) J. Immunol. 148:1375–81; Staunton, D. et al. (1990) Cell 61:243–54 (errata at Cell (1990) 61:1157 and Cell (1991) 667:1312); Staunton, D. et al. (1989) Cell 56:849–53; Greve, J. et al. (1989) Cell 56:839–47; Staunton, D. et al. (1992) J. Immunol. 148:3271–4; Register, R. et al. (1991) J. Virol. 65:6589–96; Greve, J. et al. (1991) J. Virol. 65:6015–23; and Lineberger, D. et al. (1992) Virus Res. 24:173–186, discuss binding of ICAM-1 to rhinovirus. Oppenheimer-Marks, N. et al. (1991) J. Immunol. 147:2913–21; and Perry, M. et al. (1992) Cell Tissue Res. 268:317–26; describe the role of ICAM-1 in transendothelial migration, and Dustin, M. et al. (1992) J. Immunol. 148:2654–63, describe B cell migration on ICAM-1 coated substrates. Webb, D. et al. (1991) J. Immunol. 146:3682–6, describe the role of ICAM-1 in monocyte invasion of tumors. Berendt, A. et al. (1992) Cell 68:71–81; Ockenhouse, C. et al. (1992) Cell 68:63–9; and Ockenhouse, C. et al. (1991) J. Infect. Dis. 164:163–169, discuss ICAM-1 in its role as a receptor for *Plasmodium falciparum*. Gruber, M. et al. (1991) AIDS Res. Hum. Retroviruses 7:45–53, discuss the role of ICAM-1 in HIV syncytia formation. Dohlsten, M. et al. (1991) Eur. J. Immunol. 21:131–5, discuss the role of ICAM-1 in staphylococcal enterotoxin-mediated cytotoxicity.

EXAMPLE VIII

Isolation and Molecular Cloning of the Human CD19, CD20, CDw32a, CDw32b and CD40 Antigens The rapid immunoselection cloning method of the present invention was applied to isolate and clone the CD19, CD20, CDw32a, CDw32b, and CD40 antigens. The nucleotide sequence of CD19is shown in FIGS. 12A–12B. The nucleotide sequence of CD20 is shown in FIGS. 13A–13B. The nucleotide sequence of CDw32a is shown in FIGS. 14A–14B. The nucleotide sequence of CDw32b is shown in FIGS. 15A–15B. The nucleotide sequence of CD40 is shown in FIG. 16.

EXAMPLE IX

Cloning, Sequence and Expression of CD36

To isolate a cDNA clone encoding CD36, a human placenta cDNA (Simmons and Seed (1988) Nature 333:568–570) was transferred into COS cells using DEAE-Dextran as a facilitator (Example I, supra). 48 hours post-transfection the cells were detached from the dishes without trypsin, incubated with monoclonal anti-CD36antibodies 5F1 (Bernstein et al. (1982) *J. Immunol.* 128:876–881) (Andrews et al. (1984) *J. Immunol.* 128:398–404) and panned on dishes coated with goat anti-mouse immunoglobulin antibodies. Nonadherent cells were removed by gentle washing, the adherent cells were lysed, and episomal plasmids recovered from the cells were purified and transformed into *E. coli.* After two similar rounds of enrichment following spheroplast fusion, plasmid DNAs recovered from 11 out of 12 randomly chosen colonies were found to direct the appearance of CD36 determinants in transfected COS cells.

Two of the clones were chosen at random for further analysis. Both bore inserts of about 1.9 kb, and showed identical restriction enzyme fragment patterns. COS cells transfected with either of these clones reacted with monoclonal antibodies 5F1 and F13, and with OKM5 (Ortho, Raritan, N.J.). Immunoprecipitation of transfected cells with a pool of anti-CD36 antibodies revealed the presence of an 83 kd molecule present on transfected COS cells and C32 melanoma cells, and absent from control (CD25-transfected) COS cells. A high molecular weight species, possibly dimeric CD36, was immunoprecipitated from the transfected COS cell lysate, but not from the C32 cell lysate. The nucleotide sequence is given in Table 1. In Table 1, the nucleotide sequence numbering is shown in the left margin at the beginning of each line. The deduced amino acid sequence is shown as single letter code underneath the beginning of each coding nucleotide triplet, with the initiation methionine indicated by the number 1 above the initiator codon. The potential sites of N-linked glycosylaton in the derived amino acid sequence are underlined by a single dashed line. The putative transmembrane domain is double-underlined. Although two consensus polyadenylation (AATAAA) motifs are found in the cDNA, there is no poly(A) tail, and none of the RNA species observed by blot hybridization are short enough to correspond to polyadenylation at these sites, assuming that the transcripts bear the same approximate 5' end as observed in the clone. The presumed initiation codon is not the first ATG found in the clone, but the previous two are closely followed by in-frame termination codons. The predicted initiator methionine is followed by a short hydrophobic region resembling a secretory signal sequence for which, however, no clear identification of the cleavage site can be made. The recent determination of Table 1 the amino terminal 36 amino acid sequence (Tandon et al. *J. Biol. Chem.* 264:7570–7575 (1989)) indicates that the mature polypeptide begins at the amino acid residue immediately following the initiator methionine. It is not clear whether the single Arg residue preceding the hydrophobic region would be sufficient to allow amino terminal membrane anchoring. The resulting polypeptide possesses 471 residues with a predicted molecular weight of about 53 kd. The proposed extracellular domain is followed by 27 predominantly hydrophobic residues corresponding to a transmembrane domain, and 6 residues (of which 3 are basic) corresponding to an attenuated intracellular domain. The presence of 10 potential N-linked glycosylation sites appears sufficient to account for the discrepancy in molecular mass between the predicted polypeptide and the 83 kd species found by immunoprecipitation. No significant homology was detected following comparison of the entire sequence to various databases of known proteins. However some internal structure was apparent. All of the cysteine residues in the extracellular domain are confined to a domain defined by residues 937 to 1209 of the nucleotide sequence. Taking the cysteine placement as a guide, the extracellular domain could be divided into three segments, in which two domains without cysteine preceded and followed the cysteine rich segment. However sequence comparisons with these segments did not show any significant relatedness to other molecules in existing databases, nor, in particular, to thrombospondin.

The CD36 protein was purified by immunoprecipitation. Since the rapid immunoselection cloning method depended upon expression of transfected COS cells, it follows that the same cell lines from which CD36 cDNA was cloned could also be used as a source of the expressed protein.

TABLE 1

```
   1 GAAAAATCCTTCCTTCTTAGCCATTTTAAAGATAGCTTTCCAATGAATTCTTTCTTGACTCATCAGTTCCTTTCTGTAAAATTCATGTCTGTCTGTGTTGATTTGTGAATAA
                                                                                                     1
 121 GAACCAGAGCTTGTAGAAACCACTTTAATCATCCAGGAQTTTGCAAAAACAGGTGCTTAACACTAATTCACCTCTGAACAAGAAAAATGGCTGTGACCGAACTGTGGCTCATC
                                                                        M  Q  C  D  R  N  C  G  L  I
 241 GCTGGGGCTGTCATTGGTGTCCTGGCTGTGTTTCAGCAGATATTCTTAATGCCAGTTGTGGATCCTGATCTTATCCAGAGACAATTAAAAGCAAGTTCTCCTGAAGAAGTACAATTGCT
      A  G  A  V  I  Q  A  V  L  A  V  F  Q  Q  I  L  M  P  V  Q  D  L  L  I  Q  K  T  I  K  K  Q  V  V  L  E  E  G  T  I  A
 301 TTTAAAATTGGGTTAAAACAGGCACAGAAGTTTACAGAACAGTTTGGATCTTTGAATATGCAAATCCACAGCAAGTTGATTGATGAACAGCAGCAACTCATTCAAGTTAGCAAAGAGGTCCT
      F  K  N  W  Y  K  T  G  T  E  Y  Y  R  Q  F  W  I  F  D  V  Q  N  P  Q  E  V  M  N  S  S  N  I  Q  V  K  Q  R  G  P
 401 TATACGTACAGAGTTCGTTTTCTAGCCAAGGAAAATGTAACCCAAGGACGCTGAAGACAACCAGTCTCTTTCCTGCAGCCCAATGGTGTCCATCTCGAACTTCGAACTTCACTATCAGTTGGAACA
      Y  T  Y  R  Y  R  F  L  A  K  E  N  V  T  Q  D  A  E  D  N  T  V  S  F  L  Q  P  N  Q  A  I  F  E  P  S  L  S  V  G  T
 601 GAGGCTGACAACTTCACAGTTCTCAATCTGGCTGTGGCCAGCTGCAATCCCATACTATCAAATCCCATATCTATCAAATCATCCCAATTGACTTATTAACAAGTCAAAATCTTCATGTTC
      E  A  D  N  F  T  V  L  N  L  A  V  A  A  S  N  I  Y  Q  N  Q  F  V  Q  M  I  L  N  S  L  I  N  K  S  S  M  F
 721 CAAGTCAGAACTTTGAGAGAAACTGTTATGGGGCTATAGGGGATCCATTTTGAGTTTGGTCCGTACCCAGTTGGTCTGTTATCCTACAACAATACTGCACATGGA
      Q  Y  R  T  L  R  E  L  L  W  Q  Y  R  D  P  F  L  S  L  V  P  Y  P  V  T  T  V  G  L  F  Y  P  Y  N  N  T  A  D  G
 841 GTTTATAAAGTTTTCAATGGAAAAGATAACATAAGTAAAGTTGCCATAATCGACACATAAAGGAATCTGTCCTATTGGGAAGTCACTGCGACATGATTAATGTACAGAT
      V  Y  K  V  F  N  G  K  D  N  I  S  K  V  A  I  I  D  T  Y  K  G  K  R  N  L  S  Y  W  E  S  N  C  D  M  I  N  A  T  D
 901 GCAAGTCAGAACCCTCATTCCTTTGAGAAAAGCCAGGTATTGCCAGTCAATCTATGCCTATATTCAGGTCAATCTATGCCTGTATTTGATATTCCGACGTTAATCTGAAGGAATCCCTGTG
      A  S  F  F  E  E  K  S  Q  V  L  Q  F  F  S  S  D  I  C  R  S  I  Y  A  V  F  F  E  S  D  V  N  L  K  G  I  P  V
1081 TATAGAATTGTTTCCAATCCAAGGCTTGCCTCTCCATTGAAACCCAGACAACTATTGTTTCTGCACAGATAAAATTATCTCAAAAATTGTACATCATTCTAAAAAACTCTSYQVLDI
      Y  R  F  V  L  P  S  K  A  F  A  S  P  V  E  N  P  D  N  Y  C  F  C  T  E  K  I  I  S  K  N  C  T  S  Y  Q  V  L  D  I
1281 AGCAAATGCAAGAAGCCACACCTGTACTTCACTTCCTGTATGCAAGTCCTGATGTTTCAAGATCCTGAATGTTTCAAGACCTATTGAATTAACCCAATCAAGAAGAACATAGGACATAC
      S  K  C  K  E  G  R  P  V  Y  I  S  L  P  N  F  L  Y  A  S  P  D  V  S  E  P  I  D  Q  L  N  P  N  E  E  E  N  R  T  Y
```

TABLE 1-continued

```
1321 TTGGATATTGAACCTATAACTGGATTCACTTTACAATTTGCAAAACGGCTGCAGGTCACCTATTGGTCAAGCCATCAQAAAATTCAAGTATTAAAGAATCGAAGAGGAACTATATT
     L  D  I  E  P  I  T  Q  F  T  L  Q  F  A  K  R  L  Q  V  N  L  L  V  K  P  S  E  K  I  Q  V  L  K  N  L  K  R  N  Y  I

1461 GTTGCCTATTCTTTGGCTTAATGAGACTGGGACCGGAACCATTGGTGTAQAGAAGGCAAACATGTTCAGAAGTCAAGTAACTGGAAAATAAACCTCCTTGGCCTGATAGAAATGATCTTACTCAGT
     Y  P  I  L  W  L  N  E  T  Q  T  T  I  G  D  E  K  A  N  μ  F  R  S  Q  V  T  Q  K  I  N  L  L  Q  L  I  E  μ  I  L  L  S
                                                                                 =========================================

1671 GTTGGTGTGGATGTTTGTTGCTTTTATGATTTCATATTGTGCATGCACATCGAAAACAATAAATAAGTATGTACCAAAAAATATGTCTTCAATATATATTATTAGCTTATATATACTTGT
     Y  G  V  V  μ  F  Y  λ  F  μ  I  S  Y  C  λ  C  R  S  Q  T  I  K  ↑
     ===================================================

1691 TTTCACTTTATCAAAGAGAAGTTACATATTAGGCCATATATTTCTAGACATGTCTAGCCACTGATCATTTTTAAATATAGGTAAATAAACCTATAAATATATCACGCAGATCACTAA

1811 AGTATATCTTTAATTCTGGGAGAAATGAAGAAATAAAAAGATGTACTTGTGACCATTGTAACAATAGCACAAAT
```

C32 melanoma cells, CD36 transfected cells COS cells, and CD25 (control) transfected COS cells were surface labelled with Na$^{125}$I and lysed in a phosphate buffered saline solution containing 1 mM phenylmethylsulfonyl fluoride, 0.5% NP-40 and 0.1% sodium dodecyl sulfate. Anti-CD36 monoclonal antibodies were added, and allowed to absorb to the lysate for 12 hours at 4° C., after which goat anti-mouse Immunoglobulin beads (Cappel) were added, mixed for two hours, and washed as described (Clark and Einfeld *J. Immunol.* 135:155–167 (1986)). Larger amounts of protein can also be obtained in purified form from a transfected COS cell lysate by an immunoaffinity column purification. Other antibodies to CD36 may be obtained, using CD36 protein, expressed and/or purified as described, as immunogen.

CD36 has been identified as a binding site for cytoadherence of *Plasmodum falciparum* parasitized erythrocytes, by the inventors herein and by Ockenhouse, C. D. et al. (1989) Science 243:1469–1741. Cytoadhesion of parasitized erythrocytes has been shown to be blocked by monoclonal antibodies to CD36. Incubation of infected erythrocytes with COS cells transfected with a CD36 cDNA showed pronounced cytoadherence. The ability of *P. falciparum* parasitized erythrocytes to evade splenic clearance by adherence to peripheral vascular beds is thought to play an important role in the pathogenicity of *Falciparum* malaria and to contribute to the lethal syndrome of cerebral malaria by causing occlusion of the small vessels of the brain. Therefore the cDNA and purified protein of the present invention are useful for providing sufficient purified CD36 to make therapeutic monoclonal antibodies.

EXAMPLE X

Isolation and Cloning of Three cDNA Clones Encoding Macrophage-Specific FcRI Three independent cDNA clones (designated p135, p90 and p98/X2) encoding human FcRI were isolated by the rapid immunoselection cloning method of the present invention from a cDNA library expressed in COS cells. (See also Allen, J. M. and Seed B., *Science* 243:378–381 (1989)). The cDNA library was constructed from polyadenylated RNA obtained from cells of a single patient undergoing extracorporeal interleukin-2 induction therapy. Expression of the three cDNAs in COS cells gave rise to IgG binding of the appropriate affinity and subtype specificity. DNA sequence analysis revealed that the cDNAs encode similar type I integral membrane proteins with 3 extracellular immunoglobulin domains. The intracellular domain of p98/X2 diverges from that of the other two cDNAs. A composite sequence of the three cDNAs is shown in Table 2 with the nucleotide differences of the p89/X2 or p90 clones shown respectively below or above the p135 sequence. Dashes denote gaps and no residues are shown above or below where the sequences are identical. The p90 cDNA has the shortest 5' untranslated region, 7 additional residues between the polyadenylation motif and the poly A tract, and 2 polymorphisms in the coding region. The p98/X2 cDNA has the longest 5' untranslated region, 1 polymorphism in the coding sequence, and diverges from the other two cDNAs at residue 1051, becoming a complex pattern of repeats of upstream sequences. The p98/X2 clone lacks a polyadenylation site.

The FcRI protein from each of the three clones was purified from the respective COS cell lines which expressed them, by immuno-adsorption to IgG-agarose. (See Stengelin S. et al., *EMBO J.* 7:1053 (1988)). Gel electrophoresis of purified proteins showed a single species from p135 and p90 COS cells, relative molecular size 70 kd. Cells transfected with p98/X2 expressed a protein of 67 kd. A slightly larger protein of 75 kd was adsorbed from untreated and interferon-gamma-treated U937 promonocyte cells. The smaller mass observed in COS cells is consistent with the reduced masses observed from Table 2 other surface antigens expressed in COS cells, see e.g., Example IX.

Figure 4B:
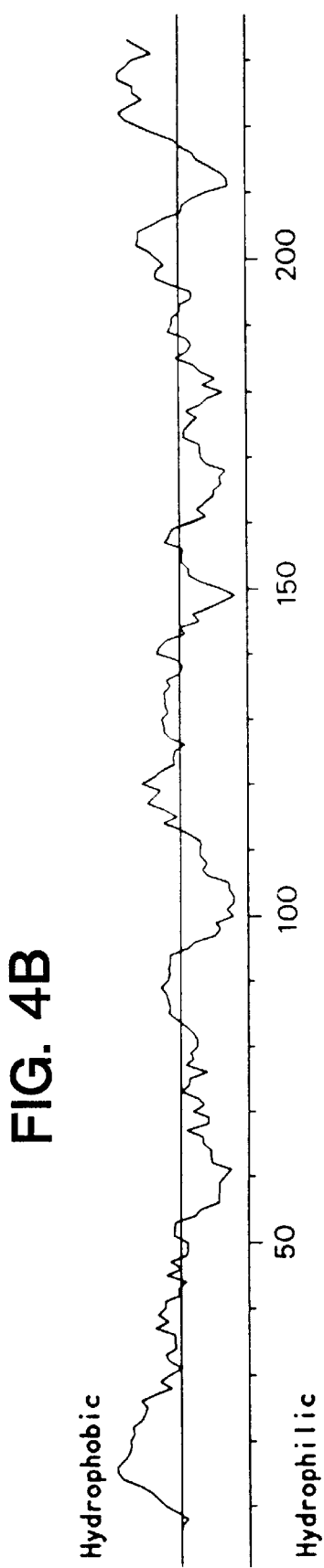

The predicted polypeptide sequences show the typical features of a type I integral membrane protein, and include a short hydrophobic signal sequence, a single 21-residue hydrophobic membrane-spanning domain, and a short, highly charged cytoplasmic domain (FIGS. 4A–4B). The extracellular portion contains six potential N-linked glycosylation sites and six Cys residues distributed among three C2 set Ig-related domains.

FcRI is a high-affinity receptor for the Fc portion of IgG, normally located on the cell surfaces of macrophages. The ability to interfere with such bonding, or to cause it to occur on surfaces other than macrophages, is useful in therapy. For example, a fusion protein of FcRI and a receptor ligand will be helpful to increase the potency of antibodies in therapy.

EXAMPLE XI

Isolation and Cloning of cDNA Encoding T-Lymphocyte TLiSA Antigen

A cDNA clone encoding TLiSA1 was obtained from a human T-cell cDNA library transferred into COS cell as described and subjected to the rapid immunoselection cloning method of the invention. A monoclonal antibody ACT-T-SET TLiSA1 (T-Cell Sciences Corp., Cambridge, Mass.) was used to detect transfected COS cells expressing the cloned cDNA, by positive indirect immunofluorescence. The positive plasmid contained in a 1.7 kb insert.

TABLE 2

```
                                                                                          100
--------------QACAGATTTCACTGCTCCCCACACCAGCTTGGGAGACAACATGGTTTCTGCACACTGCAAGTGGACAAGTGGACACCACAAACCC
CTTCAATATCTTGCAATCTT                                N W F L T L L L W V P Y D Q Q Y D T T K A
                     A                           C
ACTCATCTCTTCCACCCTCCATCCCAGCGTGTTCAAGAGCAAACCTGTACCTTGCCTGTGAGGTGCTCCATCTGCCTCGAGACAGCAGCTCTACACTCTCATCAATCAATGCACACC
 Y I S L Q P P V V S Y F Q E E T V T L N C E V L N L P Q S S T Q V F L N C T A
CACTCACACACCTGACCCCAGCTACACAATCACCTCTGCCAGTGTCAAGACAGTGGTGAATACAGGTGCCAGAGAGGTCTCTCAGGCAGCAAGTTACCCCAATACAGCTGGAAACCACAG
 T G T T S T P S Y R I T S A S V N D S D E Y R C Q R Q L S Q R S D P I Q L E T N R
ACCCTGCCTACTACTGCAGCTCTCCAGCAGAGTCTTCACCCCAACCCAGAACCTCTATTCCACGCTCCCTCACACATAAGCTCCTCACATGCTCATCCTTACTCTGAAATCGCA
 T P A T T A A L Q Q S S R V F T E Q P L A R C N A W K D K L V T N V L Y Y R N C K
AGCCTTTAACTTTTCCACTGAATTCCACTGAAATCTTCAGCTGCTGCCTGGATGCCCAGGGGAATCTGGTTAGCCCCCTCCTGGAGCAGAATCTGGTAACTCTCTCTCCAGACCCCTCC
 A F K F F H W N S L T I K T N I S N N Q T Y N C S Q N G K N R Y Y S A C I S
                                                                                                 700
TCTCATTTCTGAAAGAGCTATTTCCAGCTGCAGTGCTGCCAGTGCTCCAGTGGACAGGAGATCTGGTGGATCCCCTCAGGTGATGATCCCCACAGGTCTCAAACTTGGTCTCTTCCAGACCCTCC
 V T V R E L F P A P V L L E Q N L V T S P L L E Q N L V T L S G E T K L L Q R P Q
TTTGCAGCTTTACTTCTCCTTCTACATGCCAGTCAAAACACATCCAGTTACCGGTTAATGAGTTTCATGATGAAGAGAAGACTCTGGGTTATACTGCTGGAGG
 L Q L Y F S F Y N Q S K T L R Q R N T S S E Y Q I L T A R R E D S C L Y V C E A
TGCCACAGAGGATGGAAATGCCTTAAGCCAGCCCTGAGTTGGAGCTTCAGTGATTCAGTTGGAAAAGAAGAAATCGCTCCTTCATGCTTGGAGCTCCTCCCCCATCTCTCCTCGCACTCTGGAATTAAT
 A T E D C N V L K R S P E L E L Q V L Q L P T P V W F N V L F Y L A Y Q I N
CTTTTTTACTACTCCAGTCTTCTCCTTGGGTGACAATGCGTAAAGATGGAACTGAAAAGAATCAGGACAAACCTGAAAAAAGAAAAAAGAAAAAGAAGAAATGGGATCTTGAAATCTCACTCGATTCTCAGAATGAAAAGAAAGTCACCAGCCTTCA
 F L Y N T V L W V T I R K E L K R K K K K W D L E I S L D S Q N E K K V T S S L Q
                                                                         98
                                          AGGCCAAGCACTTGAAGCTCCAACTCCAACAGC
                                           G Q A L E A P T Q Q
                                                                                                 1800
ACAAACACACATTATAGAAAACAGCTGAAATGTCAGGAACAAGAAAAACAGAACACTGCAGGAAGACCCCAGGCCCCCAGGCCCCCAGGCCCAGGCCAGGCCCCCACGTAACAGCGGCT
 E D R H L E E E L K C Q E Q K E E Q L Q E Q Y N R K E P Q Q A T
CTCCCCCTTAAGGACAATTTACATCCTCTGAATCCAAATACTAACATGCTAGAACCTCAGAAGAACAGCAACACACACAGCAGCCAACAGTCTTCTCTTCTCTCTCAGCA
C A
ATTCGAATCTGAACCGTCCCGTCCCCTCCCCACCCACCCACTCCTTCCCCCGGTGAGCACTCCGTACAAAACATCAAAAGTTCAACAACACCCAGACTGTGTCTCATGGTATGTAACTCTTAAAAGCAAATAAATG
TACTTCAGACCGATCTGTTCCTGCCACCTGCCAGGGGTCTTGCAGCTTTACTTCTTCCTTCCTTCATGGCAGTAAGGCAG
AACTGCCG-------AAAAAAAAAA
```

TLiSA protein was isolated by immunoprecipitation, as described supra, Example IX. The protein had a molecular weight of about 50 kd, as measured by gel electrophoresis.

The nucleotide sequence of the cDNA was determined by dideoxynucleotide chain termination as described, supra. The sequence of 1714 residues is given in Table 3, together with the deduced amino acid sequence shown in single letter code under the first nucleotide of each coding triplet. The ATG encoding the presumed initiator methionine is followed by a short hydrophobic region consistent with a secretory signal sequences, the most likely excision site being 19 residues into the open reading frame. The resulting polypeptide, if not further processed, would possess 317 residues with a predicted molecular weight of about 36 kd. The proposed extracellular domain is followed by 25 predominantly hydrophobic residues corresponding to the intracellular domain. (Table 3, double underlined.) The presence of 9 potential N linked glycosylation sites (Table 3, single dashed lines) appears sufficient to account for the discrepancy in molecular mass between the predicted polypeptide and the 50 kd species found by immunoprecipitation.

TLiSA is involved in mediating IL-2 induced differentiation of T-cells into cytolytic forms. Antibodies to TLiSA are useful to prevent IL-2 stimulated T cell differentiation, and to modulate adverse effects of IL-2 in therapy.

EXAMPLE XII

The Isolation and Molecular Cloning of cDNA Encoding for B lymphocyte-specific CD22 Antigen To isolate a CD22 cDNA, an expression library was constructed from the Burkitt lymphoma cell line Daudi, introduced into COS cells by the DEAE-Dextran method described supra, and subjected to three rounds of panning and reintroduction

TABLE 3

```
   1 GCGGGGAGCTGCAGTGACCAAGAGGGTGTTGAGGCTAAGAGGCCACGATGATTATCCTCTTCTTTGGCCTCTATCATGTATACAGAGCTCTGTGTGAAGAGGTGCTTTGGCATACATCAGTTCCT
                                                                       -3 -1 +1
                                                                              M D Y P T L L L A L L H V Y R A L C E E E Y L W H T S V P F

121 ATCTCAAACCAGCCTTTCAAACAGTTCCCAGAGATCGATTATCCTACTTTGCTCCTTTGGCATACATCGATCTATGTGAAGAGCTCTATGTGAAGAGGTGCTTTGGCATACATCAGTTCCTTGCATACACCAGGATTCCAGCCTCCATGGCA
                                                                                                                                          +19
                                                                                                                                  A E N M S L E C V Y P S M Q I L T Q Y E W F K I Q T Q Q D S I A I F S P T H G N
                                                                                                                                          *                                                                                    +90
 241 TTGCCGAGAACATGTCTCTAGAATGTGTGTATCCATCAATGGCAATCTTACACAGGTGGAGTGGTTTAAGATCCAGACCCAGCAGGATTCGGACCCAGGATTCCAGCCTACTCATGGCA
                                                                                                                                                  Y I R K P Y A E R Y Y F L N S T M A S N N M T L F F R N A S E D D V Q Y Y S C S
                                                                                                                                                                                                                                        *
 361 TGGTCATAAGGAAGCCCTATCCTGAGAGGGTTTACTTTTTGAATTCAACGATGGCTTCCAATAACATGACTCTTTTCTTTCGGAATGCCTCTGAAGATGTTGGCTACTATTCCTGCT
     Y I R K P Y A E R Y Y F L N S T M A S N N M T L F F R N A S E D D V Q Y Y S C S
                                                                                                                                                                                                                                                                                                                *
 481 CTCTTTACACTTACCCACAGGGAACTTGGCAGGAACTGGTTCAGTGATACAGGTGGTTCAGGAACAGGTGGTTCAGTGCCATCAAATAGCCACATGTTTGAGGCAGCTGTGCCATCAAATAGTTTTGAGGCAGCTGTGCCATCAAATAGTTTTGAGGCAGCTGTACCACATGTTTCGGAACCTGGAAAGAATGTCA
                                                                                                                                                                                                    L Y T Y P Q Q T W Q K V I Q V V Q S N S H I Y S E P Q K N Y T
                                                                                                                                                                                                                                                                                            +203
 601 CACTCACTTGTCAGCCTCAGATGACGTGGCCTGTGCAGGCAGTGAGGTGCGAAAAGATCCAGCCCGTCAGATCGACCTCCTTAACTTGCTACTGCAAACTGGCCATGGCCATGGTCCATGGCCTACTGCCAGGCCAGGCCAGGCCAG
     L T C Q P Q M T W P V Q A V R W E K I Q P R Q I D L L T Y C H L Y H Q R N F T S
                                                                                                                                                                                                *
 721 CCAAGTTCCCAAGACAAATAGTGAGCAACTGCAGCAACTGCAGCCACGGAAGGTGGAGCACGCCACGGAGCACTCGGGCTTTACCGCTGCTACTGCAGCCAGCCAG
     K F P P R Q I V S N C S H Q R W S V I V I P D Y T V S D S Q L Y R C Y L Q A S A G

841 GAGAAAACGAGAATCCTGCTGATCACATTGACTGTAGCCAGCTGAGGTAAAACCGATAACCATATACCCTCTTTGTGCTGGAGGGACAGTTTATGTGTGTATCTCAATTACCA
     E N E T F V M R L T V A E Q K T D N Q Y T L F Y A Q G T V L L L F V I S I T T

901 CCATCATGTCATTTCCTTAACAGAAGGAGAGGAGAGGAGGACCATATTTATGTCAACTATCCAACCTTCTCTGCAGACCAAAGACTAGAGTTTAAGCTTATTCTTGACATGAGTCATTAGTAATGACT
     I I V I F L H R R R E R R D L F T E S W D T Q K A P N N Y R S P I S T S Q P

1081 CTACCAATCAATCCATCCATGATACAAGAGACCATATTTATGTCAACTATCCAACCTTCTCTGCAGACCAAAGACTAGAGTTTAAGCTTATTCTTGACATGAGTCATTAGTAATGACT
     T N Q S M D D T R E D I Y V N Y P T F S R R P K T R Y
1201 CTTATGTACTCATGCATGGATCTTTATGCAATTTTTTTCCACTACCAAGGTCTACCTTAGATACTAGTTGTCTCAATTGAGTTACTTGAGTTGATAGGAAAAATACTTCATTACCTAAAATCA
1321 TTTTTCATAGAACTGTTTGCAGAAAACCTGACTCTAACTGGTTTATATACAAAAGAAAACTTACTGTATCATATAACAGAATGATCCAGGGAGATTAAGCTTTGGGCAAGGCTATTTAC
1441 CAGGGCTTAAATGTTGTGTCTAGAATTAAGGCATAAAACTGGCTTCTGAATCCCTTCCTGCTTCAGAGTTGTTGGATCCATTTCCCGGATCATATAACAGAATGATCCAGGGAGATTAAGCTTTGGGCAAGGCTATTTAC
1601 GTGTTGGCAAGATGGCTGCCAACTCTTGGCAATTCATACATCCTTGTTTCTGTCTGGTAGAGAGTTTGCTCTCAAATGGAGCAAACAAATTTCATTATTTTCATTGTTAAATAGGCA
1881 ACATGACCATAAAGGATGGAATGGCTTAAGTAAA
``` into *E. coli* as described in Seed and Aruffo, *Proc. Natl. Acad. Sci. USA* 84:3365–3369 (1987) and Aruffo and Seed, *Proc Natl. Acad. Sci. USA* 84:8573–8577 (1987). Of 16 plasmids picked after the third round, two tested positive for CD22 expression by indirect immunofluorescence in COS cells. Of the five carbohydrate-related epitopes, A, B, C, D and E, recognized by anti-CD22 monoclonal antibodies, only epitopes A and D were expressed in COS cells.

Immunoprecipitation of CD22 from transfected COS cells yielded a single band corresponding to a molecular mass of 110 kd, smaller than the 135 kd species obtained from Burkitt lymphoma Raji cells. The difference in mass may be related to differences in glycosylation. Since the immunogenic epitopes of CD22 are carbohydrate-related, these differences might account for the absence of epitopes B, C and E.

RNA blot hybridization analysis has revealed the presence of a major 3 kb RNA species and 4 minor species of 2.6, 2.3, 2.0 and 1.5 kb in several B cell lines. RNA encoding CD22 has not been found in several T cell lines, including peripheral blood T cells, the T cell leukemia Jurkat, the myeloid leukemia lines HL60 and U937 and the hepatoma HepG2.

DNA blot hybridization of placental DNA gave a simple pattern consistent with a single copy gene. DNA sequence analysis by the dideoxy method described supra showed that the 2107 bp insert encoded a polypeptide of 647 amino acids. The nucleotide and amino acid sequences appear in Table 4. The initial methionine is followed by 18 predominantly hydrophobic amino acids resembling a secretory signal sequence. The mature protein, having a relative molecular weight of 71.1 kd consists of an extracellular portion of 491 residues, followed by a 19 residue membrane-spanning domain (doubly underlined), and an intracellular domain of 118 amino acids. Ten potential N-linked glycosylation sites (N—X—S/T, X not equal to P) are found in the predicted extracellular domain, as well as a large number of serine and threonine residues which may be sites of O-linked glycan addition. The abundance of potential glycosylation sites and the difference in mass between the predicted protein backbone and the product precipitated from COS cells and B cell lines suggest that about 50% of the mass of CD22 is contributed by carbohydrate.

TABLE 4

```
1    ACGCGGAAAC AGGCTTGCAC CCAGACACGA CACCATGCAT CTCCTCGGCC CCTGGCTCCT GCTCCTGGTT CTAGAATACT
                                                    M  H  L  L  G  P  W  L  L  L  L  V  L  E  Y  L

81   TGGCTTTCTC TGACTCAAGT AAATGGGTTT TTGAGCACCC TGAAACCCTC TACGCCTGGG AGGGGGCCTG CGTCTGGATC
     A  F  S  D  S  S  K  W  V  F  E  H  P  E  T  L  Y  A  W  E  G  A  C  V  W  I

161  CCCTGCACCT ACAGAGCCCT AGATGGTGAC CTGGAAAGCT TCATCCTGTT CCACAATCCT GAGTATAACA AGAACACCTC
     P  C  T  Y  R  A  L  D  G  D  L  E  S  F  I  L  F  H  N  P  E  Y  N  K  N  T  S

241  GAAGTTTGAT GGGACAAGAC TCTATGAAAG CACAAAGGAT GGGAAGGTTC CTTCTGAGCA GAAAGGGGTG CAATTCCTGG
     K  F  D  G  T  R  L  Y  E  S  T  K  D  G  K  V  P  S  E  Q  K  R  V  Q  F  L  G

321  GAGACAAGAA TAAGAACTGC ACACTGAGTA TCCACCCGGT GCACCTCAAT GACAGTGGTC AGCTGGGGCT GAGGATGGAG
     D  K  N  K  N  C  T  L  S  I  H  P  V  H  L  N  D  S  G  Q  L  G  L  R  M  E

401  TCCAAGACTG AGAAATGGAT GGAACGAATA CACCTCAATG TCTCTGAAAG GCCTTTTCCA CCTCATATCC AGCTCCCTCC
     S  K  T  E  K  W  M  E  R  I  H  L  N  V  S  E  R  P  F  P  P  H  I  Q  L  P  P

481  AGAAATTCAA GAGTCCCAGG AAGTCACTCT GACCTGCTTG CTGAATTTCT CCTGCTATGG GTATCCGATC CAATTGCAGT
     E  I  Q  E  S  Q  E  V  T  L  T  C  L  L  N  F  S  C  Y  G  Y  P  I  Q  L  Q  W

561  GGCTCCTAGA GGGGGTTCCA ATGAGGCAGG CTGCTGTCAC CTCGACCTCC TTGACCATCA AGTCTGTCTT CACCCGGAGC
     L  L  E  G  V  P  M  R  Q  A  A  V  T  S  T  S  L  T  I  K  S  V  F  T  R  S

641  GAGCTCAAGT TCTCCCCACA GTGGAGTCAC CATGGGAAGA TTGTGACCTG CCAGCTTCAG GATGCAGATG GGAAGTTCCT
     E  L  K  F  S  P  Q  W  S  H  G  K  I  V  T  C  Q  L  Q  D  A  D  G  K  F  L

721  CTCCAATGAC ACGGTGCAGC TGAACGTGAA GCATCCTCCC AAGAAGGTGA CCACAGTGAT TCAAAACCCC ATGCCGATTC
     S  N  D  T  V  Q  L  N  V  K  H  P  P  K  K  V  T  T  V  I  Q  N  P  M  P  I  R

801  GAGAAGGAGA CACAGTGACC CTTTCCTGTA ACTACAATTC CAGTAACCCC AGTGTTACCC GGTATGAATG GAAACCCCAT
     E  G  D  T  V  T  L  S  C  N  Y  N  S  S  N  P  S  V  T  R  Y  E  W  K  P  H

881  GGCGCCTGGG AGGAGCCATC GCTTGGGGTG CTGAAGATCC AAAACGTTGG CTGGGACAAC ACAACCATCG CCTGCGCAGC
     G  A  W  E  E  P  S  L  G  V  L  K  I  Q  N  V  G  W  D  N  T  T  I  A  C  A  A

961  TTGTAATAGT TGGTGCTCGT GGGCCTCCCC TGTCGCCCTG AATGTCCAGT ATGCCCCCCG AGACGTGAGG GTCCGGAAAA
     C  N  S  W  C  S  W  A  S  P  V  A  L  N  V  Q  Y  A  P  R  D  V  R  V  R  K  I

1041 TCAAGCCCCT TTCCGAGATT CACTCTGGAA ACTCGGTCAG CCTCCAATGT GACTTCTCAA GCAGCCACCC CAAAGAAGTC
     K  P  L  S  E  I  H  S  G  N  S  V  S  L  Q  C  D  F  S  S  S  H  P  K  E  V

1121 CAGTTCTTCT GGGAGAAAAA TGGCAGGCTT CTGGGGAAAG AAAGCCAGCT GAATTTTGAC TCCATCTCCC CAGAAGATGC
     Q  F  F  W  E  K  N  G  R  L  L  G  K  E  S  Q  L  N  F  D  S  I  S  P  E  D  A

1201 TGGGAGTTAC AGCTGCTGGG TGAACAACTC CATAGGACAG ACAGCGTCCA AGGCCTGGAC ACTTGAAGTG CTGTATGCAC
     G  S  Y  S  C  W  V  N  N  S  I  G  Q  T  A  S  K  A  W  T  L  E  V  L  Y  A  P

1281 CCAGGAGGCT GCGTGTGTCC ATGAGCCCGG GGGACCAAGT GATGGAGGGG AAGAGTGCAA CCCTGACCTG TGAGAGCGAC
     R  R  L  R  V  S  M  S  P  G  D  Q  V  M  E  G  K  S  A  T  L  T  C  E  S  D

1361 GCCAACCCTC CCGTCTCCCA CTACACCTGG TTTGACTGGA ATAACCAAAG CCTCCCCTAC CACAGCCAGA AGCTGAGATT
     A  N  P  P  V  S  H  Y  T  W  F  D  W  N  N  Q  S  L  P  Y  H  S  Q  K  L  R  L
```

TABLE 4-continued

```
1441 GGAGCCGGTG AAGGTCCAGC ACTCGGGTGC CTACTGGTGC CAGGGGACCA ACAGTGTGGG CAAGGGCCGT TCGCCTCTCA
       E   P   V   K   V   Q   H   S   G   A   Y   W   C   Q   G   T   N   S   V   G   K   G   R   S   P   L   S

1521 GCACCCTCAC CGTCTACTAT AGCCCGGAGA CCATCGGCAG GCGAGTGGCT GTGGGACTCG GGTCCTGCCT CGCCATCCTC
       T   L   T   V   Y   Y   S   P   E   T   I   G   R   R   V   A   V   G   L   G   S   C   L   A   I   L
                            ======  ==========  ==========  ==========

1601 ATCCTGGCAA TCTGTGGGCT CAAGCTCCAG CGACGTTGGA AGAGGACACA GAGCCAGCAG GGGCTTCAGG AGAATTCCAG
       I   L   A   I   C   G   L   K   L   Q   R   R   W   K   R   T   Q   S   Q   Q   G   L   Q   E   N   S   S
     ==========  =========

1681 CGGCCAGAGC TTCTTTGTGA GGAATAAAAA GGTTAGAAGG GCCCCCCTCT CTGAAGGCCC CCACTCCCTG GGATGCTACA
         G   Q   S   F   F   V   R   N   K   K   V   R   R   A   P   L   S   E   G   P   H   S   L   G   C   Y   N

1761 ATCCAATGAT GGAAGATGGC ATTAGCTACA CCACCCTGCG CTTTCCCGAG ATGAACATAC CACGAACTGG AGATGCAGAG
       P   M   M   E   D   G   I   S   Y   T   T   L   R   F   P   E   M   N   I   P   R   T   G   D   A   E

1841 TCCTCAGAGA TGCAGAGACC TCCCCCGGAC TGCGATGACA CGGTCACTTA TTCAGCATTG CACAAGCGCC AAGTGGGCAC
       S   S   E   M   Q   R   P   P   P   D   C   D   D   T   V   T   Y   S   A   L   H   K   R   Q   V   G   T

1921 TATGAGAACG TCATTCCAGA TTTTCCAGAA GATGAGGGGA TTCATTACTC AGAGCTGATC CAGTTTGGGG TCGGGGAGCG
       M   R   T   S   F   Q   I   F   Q   K   M   R   G   F   I   T   Q   S   *

2001 GCCTCAGGCA CAAGAAAATG TGGACTATGT GATCCTCAAA CATTGACACT GGATGGGCTG CAGCAGAGGC ACTGGGGGCA

2081 GCGGGGGCA GGGAAGTCCC CGAGTTT
```

The extracellular portion of CD22 consists of five segments having Ig-like domain organization. The short inter-cysteine spacing (63 and 64 residues in domains 1 and 2, and 42 residues in domains 3–5) suggests that they fold into the 7 strand two layer beta-sheet structure characteristic of immunoglobulin constant regions rather than the 9 strand structure of variable regions.

Because CD22 has been found to be highly homologous to myelin associated glycoprotein (MAG), a neuronal cell surface protein which mediates cell-cell contacts during myelogenesis, it was postulated that CD22 has a role in B cell adhesion. COS cells transfected with CD22 cDNA were contacted with erythrocytes or peripheral blood mononuclear cells and incubated under conditions which minimized nonspecific interaction. Erythrocyte and mononuclear cell resetting was observed with CD22-positive COS cells but not with COS cells transfected with an unrelated cDNA clone.

B cell adhesion studies involving anti-epitope monoclonal antibodies have indicated that different epitopes of CD22 may participate in erythrocyte and monocyte adhesion and that different ligands may be recognized on each cell type. B cell adhesion studies also suggest that CD22, in a manner analogous to T cell CD2, CD4 and CD8 adhesion to target cells, may promote recognition by the B cell antigen receptor by intensifying B cell-presenting cell contacts. CD22 has been previously implicated in the transmission of signals synergizing with the antigen receptor (Pezutto et al., J. Immunol. 138:98–103 (1987)) and crosslinking of surface IgM produces an intracellular calcium flux in IgM⁺CD22⁺ but not in IgM⁺CD22⁻ cells (Pezzutto et al., J. Immunol. 140:1791–1795 (1988)). These results suggest that, like T cell accessory molecules, CD22 may also participate in the regulation of signal transduction.

The ability to interfere with the binding of CD22 positive B cells with accessory cells, or the ability to cause such binding to occur on surfaces other than lymphocyte cells can be useful in diagnostics and therapy. For example, a fusion protein of CD22 and a receptor ligand fixed to a substrate will be useful in detecting the presence of a particular antigen in body fluids. A soluble form of CD22 can have immunomodulatory activity.

EXAMPLE XIII

The Isolation and Molecular Cloning of cDNA Encoding for T Lymphocyte-specific CD27 Antigen A cDNA clone encoding CD27 was obtained from human T lymphocyte cDNA transferred into COS cells and immunoselected by the method of the present invention. RNA was extracted from the mononuclear cells derived from a unit of blood, after four days of culture in medium containing 1 ug/ml phytohemagglutinin (PHA), using guanidium thiocyanate. The total RNA was poly-A selected. cDNA was made and cloned into CDM8, transfected into COS cells and the CD27 cDNA was immunoselected with monoclonal antibodies OKT18a and CLB-9F4 (provided as described in Seed and Aruffo Proc. Natl. Acad. Sci. 84:8573–8577 (1987); and Aruffo and Seed Proc. Natl. Acad. Sci. USA 84:3365–3369 (1987)). The vector contained a 1.2 kb cDNA insert.

The nucleotide sequence of the cDNA was determined by dideoxynucleotide chain termination as described, supra. The sequence of 1203 residues and the deduced amino acid sequence appear in Table 5. The initiation methionine is indicated by the number 1 above the initiator codon. The deduced CD27 polypeptide demonstrates the typical features of a type I integral membrane protein. It begins with a twenty amino acid hydrophobic region consistent with a secretory signal sequence. This hydrophobic region is followed by a 171 residue extracellular domain, a 20 residue hydrophobic membrane spanning domain (doubly underlined) and a 49 amino acid cytoplasmic domain beginning with a positively charged stop transfer sequence. There is no poly(A) tail.

The deduced CD27 amino acid sequence is highly homologous to the B lymphocyte and carcinoma antigen CD40, described supra, over its entire length. CD27 is also highly homologous to the the the receptor for nerve growth factor (NGFR) over the extracellular and transmembrane domains (Stamenkovic et al., *EMBO J.* 8:1403–1410 (1989); Johnson et al., *Cell* 47:545–554 (1989)). The most conserved structural motif found in these three proteins is the abundance of cysteines or histidines in the extracellular region. These are often found in pairs separated by two or four intervening amino acid residues similar to the arrangement seen in proteins which use this structure to bind a zinc ion. The cysteine and histidine rich region is followed by a serine, threonine and proline rich membrane proximal domain which has been suggested to be the region in which biochemically identified O-linked glycans are added to NGFR (Johnson et al. (1986), supra; Grob et al., *J. Biol. Chem.* 260:8044–8049 (1985)).

CD27 is a T lymphocyte activation antigen. Its structure suggests that it may function as the receptor for a lymphokine or growth factor. The recognition of CD27 causes T cell proliferation and increased expression of certain genes needed for the helper and effector functions of the T cell. The expression of CD27 on T cells increases two to five fold with stimulation by phytohemagglutinin (PHA) or anti-CD3 monoclonal antibodies and the addition of at least one CD27 monoclonal antibody can augment PHA stimulated proliferation of T cells (Bigler and Chiorazzi, *Leukocyte Typing II*, Vol. I:503–512 (1986); Van Lier, (1987)). T cells positive for CD27 have been found to provide help to B cells for IgM synthesis and secrete Il-2 when appropriately stimulated (Van Lier et al., *Eur. J. Immunol.* 18:811–816 (1988)).

TABLE 5

```
1    GGGGTGCAAA GAAGAGACAG CAGCGCCCAG CTTGGAGGTG CTAACTCCAG AGGCCAGCAT CAGCAACTGG GCACAGAAAG 1
81   GAGCCGCCTG GGCAGGGACC ATGGCACGGC CACATCCCTG GTGGCTGTGC GTTCTGGGGA CCCTGGTGGG GCTCTCAGCT
                          M   A   R   P   H   P   W   W   L   C   V   L   G   T   L   V   G   L   S   A

161  ACTCCAGCCC CCAAGAGCTG CCCAGAGAGG CACTACTGGG CTCAGGGAAA GCTGTGCTGC CAGATGTGTG AGCCAGGAAC
      T   P   A   P   K   S   C   P   E   R   H   Y   W   R   Q   G   K   L   C   C   Q   M   C   E   P   G   T

241  ATTCCTCGTG AAGGACTGTG ACCAGCATAG AAAGGCTGCT CAGTGTGATC CTTGCATACC GGGGGTCTCC TTCTCTCCTG
       F   L   V   K   D   C   D   Q   H   R   K   A   A   Q   C   D   P   C   I   P   G   V   S   F   S   P   D

321  ACCACCACAC CCGGCCCCAC TGTGAGAGCT GTCGGCACTG TAACTCTGGT CTTCTCGTTC GCAACTGCAC CATCACTGCC
       H   H   T   R   P   H   C   E   S   C   R   H   C   N   S   G   L   L   V   R   N   C   T   I   T   A

401  AATGCTGAGT GTGCCTGTCG CAATGGCTGG CAGTGCAGGG ACAAGGAGTG CACCGAGTGT GATCCTCTTC CAAACCCTTC
       N   A   E   C   A   C   R   N   G   W   Q   C   R   D   K   E   C   T   E   C   D   P   L   P   N   P   S

481  GCTGACCGCT CGGTCGTCTC AGGCCCTGAG CCCACACCCT CAGCCCACCC ACTTACCTTA TGTCAGTGAG ATGCTGGAGG
       L   T   A   R   S   S   Q   A   L   S   P   H   P   Q   P   T   H   L   P   Y   V   S   E   M   L   E   A

561  CCAGGACAGC TGGGCACATG CAGACTCTGG CTGACTTCAG GCAGCTGCCT GCCCGGACTC TCTCTACCCA CTGGCCACCC
       R   T   A   G   H   M   Q   T   L   A   D   F   R   Q   L   P   A   R   T   L   S   T   H   W   P   P

641  CAAAGATCCC TGTGCAGCTC CGATTTTATT CGCATCCTTG TGATCTTCTC TGGAATGTTC CTTGTTTTCA CCCTGGCCGG
       Q   R   S   L   C   S   S   D   F   I   R   I   L   V   I   F   S   G   M   F   L   V   F   T   L   A   G
                                              =======  ==========  ==========  ==========  ==========

721  GGCCCTGTTC CTCCATCAAC GAAGGAAATA TAGATCAAAC AAAGGAGAAA GTCCTGTGGA GCCTGCAGAG CCTTGTCGTT
       A   L   F   L   H   Q   R   R   K   Y   R   S   N   K   G   E   S   P   V   E   P   A   E   P   C   R   Y
     ==========  ===

801  ACAGCTGCCC CAGGGAGGAG GAGGGCAGCA CCATCCCCAT CCAGGAGGAT TACCGAAAAC CGGAGCCTGC CTGCTCCCCC
         S   C   P   R   E   E   E   G   S   T   I   P   I   Q   E   D   Y   R   K   P   E   P   A   C   S   P

881  TGAGCCAGCA CCTGCGGTAG CTGCACTACA GCCCTGGCCT CCACCCCCAC CCCGCCGACC ATCCAAGGGA GAGTGAGACC
     *

961  TGGCAGCCAC AACTGCAGTC CCATCCTCTT GTCAGGGCCC TTTCCTGTGT ACACGTGACA GAGTGCCTTT TCGAGACTGG

1041 CAGGGACGAG GACAAATATG GATGAGGTGG AGAGTGGGAA GCAGGAGCCC AGCCAGCTGC GCGCGCGTGC AGGAGGGCGG

1121 GGGCTCTGGT TGTAAGGCAC ACTTCCTGCT GCGAAAGACC CACATGCTAC AAGACGGGCA AAATAAAGTG ACAGATGACC
```

Immunoprecipitation of transfected COS cells with anti-CD27 antibodies followed by gel electrophoresis revealed the presence of a 110 kd species when not reduced and a single 55 kd band in the presence of reducing agent. This indicates that on transfected COS cells, CD27 is a disulfide linked homodimer comprised of 55 kd monomers, similar to the forms precipitated from T lymphocytes. (Bigler et al., *J. Immunol.* 141:21–28 (1988); Stockinger et al., *Leukocyte Typing II*, Vol. I:513–529 (1986); Van Lier et al., *Eur. J. Immunol.* 18:811–816 (1987)).

The ability to interfere with the binding of CD27 positive T cells with antigen presenting cells, or the ability to cause such binding to occur on surfaces other than lymphocyte cells, can be useful in diagnostics and therapy. For example, a fusion protein of CD27 and a receptor ligand fixed to a substrate will be useful in detecting the presence of a particular antigen in body fluids. A soluble CD27 fusion protein will be useful to prevent undesired T cell proliferation, for example, in certain autoimmune diseases.

EXAMPLE XIV

The Isolation and Molecular Cloning of the Two cDNA Clones Encoding T Lymphocyte-specific Leu8 Antigens Two cDNA clones encoding Leu8 determinants were isolated from a human T cell library by the method of the present invention.

The nucleotide sequence of the cDNA was determined by dideoxynucleotide chain termination as described, supra.

The DNA sequence analyses (Table 6) shows that the longer insert of the two contains 2,350 residues, whereas the shorter lacks 436 internal residues but is otherwise identical. The entire sequence of the longer clone is shown, with the portion deleted from the shorter clone overlined. The predicted amino acid sequence is shown below the nucleotide sequence. Sites of potential N-linked glycosylation are designated —CHO— and the proposed transmembrane region for the longer form is doubly underlined.

TABLE 6

```
   1  CTCCCTTTGG GCAAGGACCT GAGACCCTTG TGCTAAGTCA AGAGGCTCAA TGGGCTGCAG AAGAACTAGA GAAGGACCAA
                                                                      M   G   C   R   R   T   R   E   G   P   S

81  GCAAAGCCAT GATATTTCCA TGGAAATGTC AGAGCACCCA GAGGGACTTA TGGAACATCT TCAAGTTGTG GGGGTGGACA
       K   A   M   I   F   P   W   K   C   Q   S   T   Q   R   D   L   W   N   I   F   K   L   W   G   W   T

161  ATGCTCTGTT GTGATTTCCT GGCACATCAT GGAACCGACT GCTGGACTTA CCATTATTCT GAAAAACCCA TGAACTGGCA
       M   L   C   C   D   F   L   A   H   H   G   T   D   C   W   T   Y   H   Y   S   E   K   P   M   N   W   Q

241  AAGGGCTAGA AGATTCTGCC GAGACAATTA CACAGATTTA GTTGCCATAC AAAACAAGGC GGAAATTGAG TATCTGGAGA
       R   A   R   R   F   C   R   D   N   Y   T   D   L   V   A   I   Q   N   K   A   E   I   E   Y   L   E   K
       (1)                                                                       --CHO--
 321  AGACTCTGCC TTTCAGTCGT TCTTACTACT GGATAGGAAT CCGGAAGATA GGAGGAATAT GGACGTGGGT GGGAACCAAC
       T   L   P   F   S   R   S   Y   Y   W   I   G   I   R   K   I   G   G   I   W   T   W   V   G   T   N

401  AAATCTCTCA CTGAAGAAGC AGAGAACTGG GGAGATGGTG AGCCCAACAA CAAGAAGAAC AAGGAGGACT GCGTGGAGAT
       K   S   L   T   E   E   A   E   N   W   G   D   G   E   P   N   N   K   K   N   K   E   D   C   V   E   I
                                                                  --C HO--
 481  CTATATCAAG AGAAACAAAG ATGCAGGCAA ATGGAACGAT GACGCCTGCC ACAAACTAAA GGCAGCCCTC TGTTACACAG
       Y   I   K   R   N   K   D   A   G   K   W   N   D   D   A   C   H   K   L   K   A   A   L   C   Y   T   A

561  CTTCTTGCCA GCCCTGGTCA TGCAGTGGCC ATGGAGAATG TGTAGAAATC ATCAATAATT ACACCTGCAA CTGTGATGTG
       S   C   Q   P   W   S   C   S   G   H   G   E   C   V   E   I   I   N   N   Y   T   C   N   C   D   V

641  GGGTACTATG GCCCCAGTG TCAGTTTGTG ATTCAGTGTG AGCCTTTGGA GGCCCCAGAG CTGGGTACCA TGGACTGTAC
       G   Y   Y   G   P   Q   C   Q   F   V   I   Q   C   E   P   L   E   A   P   E   L   G   T   M   D   C   T
                          --CH O--
 721  TCACTCTTTG GGAAACTTCA GCTTCAGCTC ACAGTGTGCC TTCAGCTGCT CTGAAGGAAC AAACTTAACT GGGATTGAAG
       H   S   L   G   N   F   S   F   S   S   Q   C   A   F   S   C   S   E   G   T   N   L   T   G   I   E   E
                                                                              --CHO--
 801  AAACCACCTG TGGACCATTT GGAAACTGGT CATCTCCAGA ACCAACCTGT CAAGTGATTC AGTGTGAGCC TCTATCAGCA
       T   T   C   G   P   F   G   N   W   S   S   P   E   P   T   C   Q   V   I   Q   C   E   P   L   S   A
                              --CHO--                                              --CHO--
 881  CCAGATTTGG GGATCATGAA CTGTAGCCAT CCCCTGGCCA GCTTCAGCTT TACCTCTGCA TGTACCTTCA TCTGCTCAGA
       P   D   L   G   I   M   N   C   S   H   P   L   A   S   F   S   F   T   S   A   C   T   F   I   C   S   E
                                                                              -- CHO--
 961  AGGAACTGAG TTAATTGGGA AGAAGAAAAC CATTTGTGAA TCATCTGGAA TCTGGTCAAA TCCTAGTCCA ATATGTCAAA
       G   T   E   L   I   G   K   K   K   T   I   C   E   S   S   G   I   W   S   N   P   S   P   I   C   Q   K

1041  AATTGGACAA AAGTTTCTCA ATGATTAAGG AGGGTGATTA TAACCCCCTC TTCATTCCAG TGGCAGTCAT GGTTACTGCA
       L   D   K   S   F   S   M   I   K   E   G   D   Y   N   P   L   F   I   P   V   A   V   M   V   T   A
                                                                              === ========== ========== ==========
1121  TTCTCTGGGT TGGCATTTAT CATTTGGCTG GCAAGGAGAT TAAAAAAAGG CAAGAAATCC AAGAGAAGTA TGAATGACCC
       F   S   G   L   A   F   I   I   W   L   A   R   R   L   K   K   G   K   K   S   K   R   S   M   N   D   P
       ========== ========== ========== ==

1201  ATATTAAATC GCCCTTGGTG AAAGAAAATT CTTGGAATAC TAAAAATCAT GAGATCCTTT AAATCCTTCC ATGAAACGTT
       Y   *

1281  TTGTGTGGTG GCACCTCCTA CGTCAAACAT GAAGTGTGTT TCCTTCAGTG CATCTGGGAA GATTTCTACC TGACCAACAG

1361  TTCCTTCAGC TTCCATTTCG CCCCTCATTT ATCCCTCAAC CCCCAGCCCA CAGGTGTTTA TACAGCTCAG CTTTTTGTCT

1441  TTTCTGAGGA GAAACAAATA AGACCATAAA GGGAAAGGAT TCATGTGGAA TATAAAGATG GCTGACTTTG CTCTTTCTTG
                                                                                                   F   L
```

TABLE 6-continued (293)
```
1521 ACTCTTGTTT TCAGTTTCAA TTCAGTGCTG TACTTGATGA CAGACACTTC TAAATGAAGT GCAAATTTGA TACATATGTG
      T  L  V  F   S  F  N   S  V  L   Y  L  M  T   D  T  S   K  *

1601 AATATGGACT CAGTTTTCTT GCAGATCAAA TTTCACGTCG TCTTCTGTAT ACTGTGGAGG TACACTCTTA TAGAAAGTTC

1681 AAAAAGTCTA CGCTCTCCTT TCTTTCTAAC TCCAGTGAAG TAATGGGGTC CTGCTCAAGT TGAAAGAGTC CTATTTGCAC

1761 TGTAGCCTCG CCGTCTGTGA ATTGGACCAT CCTATTTAAC TGGCTTCAGC CTCCCCACCT TCTTCAGCCA CCTCTCTTTT

1841 TCAGTTGGCT GACTTCCACA CCTAGCATCT CATGAGTGCC AAGCAAAAGG AGAGAAGAGA GAAATAGCCT GCGCTGTTTT

1921 TTAGTTTGGG GGTTTTGCTG TTTCCTTTTA TGAGACCCAT TCCTATTTCT TATAGTCAAT GTTTCTTTTA TCACGATATT

2001 ATTAGTAAGA AAACATCACT GAAATGCTAG CTGCAAGTGA CATCTCTTTG ATGTCATATG GAAGAGTTAA AACAGGTGGA

2081 GAAATTCCTT GATTCACAAT GAAATGCTCT CCTTTCCCCT GCCCCCAGAC CTTTTATCCG ACTTACCTAG ATTCTACATA

2161 TTCTTTAAAT TTCATCTCAG GCCTCCCTCA ACCCCACCAC TTCTTTTATA ACTAGTCCTT TACTAATCCA ACCCATGATG

2241 AGCTCCTCTT CCTGGCTTCT TACTGAAAGG TTACCCTGTA ACATGCAATT TTGCATTTGA ATAAAGCCTG CTTTTTAAGT

2321 GTTAAAAAAA AAAAAAAAAA AAAAAAAAAA
```

DNA blot hybridization of fragmented human T cell genome showed a pattern consistent with a single copy gene. RNA blot hybridization revealed a major transcript of 2.4 kb in peripheral blood mononuclear cells, tonsillar B cells, and several lymphocytic cell lines; and a minor transcript of 2.0 kb, present in peripheral blood mononuclear cells, and the Jurkat and HSB-2 leukaemic T cell lines.

The deduced protein encoded by the larger insert (the conventional form) bears a strongly hydrophobic putative membrane spanning domain near its C terminus, followed by several positively charged residues resembling a cytoplasmic anchor sequence. The protein is closely related to the recently described murine Mel-14 homing receptor (Lasky et al., Cell 56:1045–1055 (1989); Siegelman et al., Science 243:1165–1172 (1989)).

The protein encoded by the shorter insert (the phospholipid anchored form) bears a weakly hydrophobic C-terminal domain characteristic of surface proteins that are attached to the cell membrane by covalent linkage to a phosphatidylinositol-substituted glycan.

Monoclonal antibodies TQ1 (Reinherz et al. (1982) J. Immun. 128:463–468) and Mel-14 (Gallatin et al. (1983) Nature 304:30–34) have been observed to react with COS cells transfected with either Leu8 clone.

The presence or absence of Leu8 on CD4+ T lymphocytes identifies suppressor-inducer and helper-inducer CD4+ T cell subsets. Leu8 is a homing receptor, allowing T cells to adhere to the specialized post-capillary endothelium of peripheral lymph nodes. The presence or absence of Leu8 classifies the T cell in terms of homing potential and tissue distribution. Serological studies have indicated that Leu8 is a marker of resting lymphocytes in peripheral lymph nodes (Poletti et al., Hum. Pathol. 19:1001–1007 (1988)). Activation of T cells by phorbol ester plus PHA results in reduced Leu8 expression and transcripts, with the reduction in Leu8 expression being more rapid than the reduction of Leu8 transcripts. It therefore appears that surface Leu8 is lost more rapidly than predicted by RNA turnover, possibly by shedding of the phosphatidylinositol-linked form (Ferguson & Williams, Ann. Rev. Biochem. 57:285–320 (1988)). Among peripheral T cells, the $CD4^+$ $Leu8^-$ subset provides help for B cell IgM and IgG synthesis (Reinherz et al., J. Immun. 128:463–468 (1982); Gatenby et al., J. Immun. 129:1997–2000), whereas $CD4^+$ $Leu8^-$ cells have been found to directly inhibit pokeweed mitogen-induced IgG synthesis (Kanof et al., J. Immun. 139:49–54 (1987)). It therefore appears that $CD4^+$ $Leu8^-$ cells, activated to provide help for B cell Ig synthesis, exit the nodes and circulate peripherally to encounter antigen-presenting cells.

The ability to interfere with the binding of $Leu8^-$ T cells to antigen presenting cells, or the ability to cause such binding to occur on surfaces other than lymphocyte cells, can be useful in diagnostics and therapy. For example, the level of activated $Leu8^-$ T cells relative to resting $Leu8^+$ cells could serve as a measure of immune response to a particular antigen.

The extracellular domain of the Leu8 transmembrane protein, which mediates adhesion to specialized endothelial cells of lymph nodes, has been observed to be quite specific in its recognition of the lectin ligand, sulfated galactosyl ceramide (sulfatide). Modification of the specificity of this binding could serve to regulate the homing potential of resting T cells. Soluble forms of Leu8 can act as anti-inflammatory agents by reducing lymphocyte migration.

EXAMPLE XV

The Isolation and Molecular Cloning of cDNAs Encoding CD44 Antigens

CD44 is a polymorphic integral membrane protein. Immunochemical and RNA blot data have supported the existence of two forms of CD44: a mesenchymal form expressed by hematopoietic cells and an epithelial form weakly expressed by normal epithelium but highly expressed by carcinomas.

To isolate a cDNA clone encoding hematopoietic CD44 (Stamenkovic et al., *Cell* 56:1057–1062 (1989)), libraries prepared from the histiocytic lymphoma cell line U937, the B lymphoblastoid line JY, the Burkitt's lymphoma line Raji, and the myeloid leukemia line KG-1 were transfected separately into COS cells by the DEAE-Dextran method, described supra. The cells were pooled 48 hours after transfection, incubated with anti-CD44 monoclonal antibodies J173 (Pesandro et al., *J. Immunol.* 137:3689–3695 (1986)), and panned on dishes coated with goat antimouse affinity purified antibody. After several washes, the adherent cells were lysed, and episomal DNA was purified and transformed into *E. coli*. After two similar rounds of enrichment following spheroplast fusion, plasmid DNA recovered from three out of eight randomly picked colonies was found to direct the appearance of hematopoietic CD44 determinants on transfected COS cells.

Two of the three clones, CD44.5 and CD44.8, bore inserts of about 1.4 kb, while the third, CD44.4, contained an insert of about 1.7 kb. COS cells transfected with either of these clones reacted with anti-CD44 monoclonal antibodies J173, F-10-44-2 (Dalchau et al., *Eur. J. Immunol.* 10:745–749 (1980)) and the anti-Pgp-1 monoclonal antibody IM7 (Trowbridge et al., *Immunogenetics* 15:299–312 (1982)). Untransfected cells showed weak J173 reactivity.

The nucleotide sequence of the hematopoietic CD44.5 cDNA (Table 7) consists of 1354 residues terminating in a short poly(A) tail 19 base pairs downstream from a CAT-AAA sequence. The ATG encoding the first methionine is embedded in a consensus initiation sequence and followed by 19 predominantly hydrophobic residues resembling a secretory signal peptide sequence. Cleavage of this peptide would yield a mature protein of 341 residues with a predicted relative molecular mass of 37.2 kd. The extracellular amino terminal domain of 248 residues is followed by 21 predominantly hydrophobic amino acids corresponding to the predicted transmembrane domain (doubly underlined) and a 72 residue hydrophilic (cytoplasmic) domain. The discrepancy between the predicted mass of the protein backbone and the deglycosylated forms observed in immunoprecipitates suggest that extensive O-linked glycosylation is present. The extracellular domain has six potential N-linked glycosylation sites, indicated in Table 7 by a —CHO— designation, and is rich in serine and threonine residues (22% in aggregate). The dipeptide SG that forms the minimal attachment site of serine-linked chondroitin sulfate in proteoglycan proteins appears at residues 160, 170, 211 and 238 in the predicted extracellular domain; these potential glycosylation sites are underlined.

TABLE 7

```
  1  CCAGCCTCTG CCAGGTTCGG TCCGCCATCC TCGTCCCGTC CTCCGCCCGG CCCTGCCCCG CGCCCAGGGA TCCTCCAGCT

81  CCTTTCGCCC GCGCCCTCCG TTCGCTCCCG ACACCATGGA CAAGTTTTGG TGGCACGCAG CCTGGGGACT CTGCCTCGTG
                                             M  D  K  F  W   W  H  A  A   W  G  L   C  L  V

161  CGGCTGAGCC TGGCGCAGAT ATAACCTGCC GCTTTGCAGG TGTATTCCAC GTGGAGAAAA ATGGTCGCTA
      R  L  S   L  A  Q  I  I  T  C   R  F  A  G   V  F  H   V  E  K  N   G  R  Y

241  CAGCATCTCT CGGACGGAGG CTGCAAGGCT TTCAATAGCA CCTTGCCCAC AATGGCCCAG --C----HO--ATGGAGAAAG
      S  I  S   R  T  E  A  C  K  A   F  N  S  T   L  P  T   M  A  Q            M  E  K  A

321  CTCTGAGCAT CGGATTTGAG ACCTGCAGGT ATGGGTTCAT AGAAGGGCAT GTGGTGATTC CCCCGGATCC CCCCAACTCC
      L  S  I   G  F  E  T  C  R  Y   M  G  F  I   E  G  H   V  V  I  P   R  I  H   P  N  S

401  --CHO-- ATCTGTGCAG CAAACAACAC AGGGGTGTAC ATCCCTCACAT CACAGACCTG ACATATTGCT TCAATGCTTC
      I  C  A   A  N  N  T   G  V  Y   I  L  T  Y   T  D  L   T  Y  C  F   N  A  S

481  AGCTCCACCT GAAGAAGATT GTACATCAGT CACAGACCTG --CHO-- TTGATGGACC AATTACCATA ACTATTGTTA
      A  P  P   E  E  D  C   V  T  S  V   T  D  L            D  G  P   I  T  I   T  I  V  N

561  --CHO-- ACCGTGATGG CACCCGCTAT GTCCAGAAAG GAGAATACAG AACGAATCCT GAAGACATCT CCCTACTGAT
      R  D  G   T  R  Y   V  Q  K  G   E  Y  R   T  N  P   E  D  I  Y   P  T  D

641  GATGACGTGA GCAGCGGCTC CTCCAGTGAA AGGAGCAGCA CTTCAGGAGG TTACATCTTT TACACCTTTT CTACTGTACA
      D  D  V  S   S  G  S   S  S  E   R  S  S  T   S  G  G   Y  I  F   Y  T  F  S   T  V  H

721  CCCCATCCCA GACGAAGACA GTCCCTGGAT CACCGACAGC ACAGACAGAA TCCCTGCTAC CAGAGACCAA GACACATTCC
      P  I  P   D  E  D  S   P  W  I   T  D  S   T  D  R  I   P  A  T   R  D  Q   D  T  F  H

801  ACCCCAGTGG GGGGTCCCAT ACCACTCATG AATCTGAATC AGATGGACAC TCACATGGGA GTCAAGAAGG TGGAGCAAAC
      P  S  G   G  S  H   T  T  H   E  S  E  S   D  G  H   S  H  G   S  Q  E  G   G  A  N
```

TABLE 7-continued

```
881   ACAACCCTCG GTCCTATAAG GACACCCCAA ATTCCAGAAT GGCTGATCAT CTTGGCATCC CTCTTGGCCT TGGCTTTGAT
       T  T  S  G  P  I  R  T  P  Q  I  P  E  W  L  I  I  L  A  S  L  L  A  L  A  L  I
              - - - -                              = = = = = = = = = = = = = = = = = = = = =

- - C
                                                         H O - -
961   TCTTGCAGTT TGCATTGCAG TCAACAGTCG AAGAAGGTGT GGGCAGAAGA AAAAGCTAGT GATCAACAGT GGCAATGGAG
       L  A  V  C  I  A  V  N  S  R  R  R  C  G  Q  K  K  L  V  I  N  S  G  N  G  A
      = = = = = = = = = = =

1041  CTGTGGAAGA CAGAAAGCCA AGTGGACTCA ACGGAGAGGC CAGCAAGTCT CAGGAAATGG TGCATTTGGT GAACAAGGAG
       V  E  D  R  K  P  S  G  L  N  G  E  A  S  K  S  Q  E  M  V  H  L  V  N  K  E

1121  TCGTCAGAAA CTCCAGACCA GTTTATGACA GCTGATGAGA CAAGGAACCT GCAGAATGTG GACATGAAGA TTGGGGTGTA
       S  S  E  T  P  D  Q  F  M  T  A  D  E  T  R  N  L  Q  N  V  D  M  K  I  G  V  *

1201  ACACCTACAC CATTATCTTG GAAAGAAACA ACCGTTGTAA ACATAACCAT TACAGGGAGC TGGGACACTT AACAGATGCA

1281  ATGTGCTACT GATTGTTTCA TTGCGAATCT TTTTTAGCAT AAAATTTTCT ACTCTTTTTG TTAAAAAAAA AAAA    1354
```

RNA blot hybridization revealed three major messages of 1.6, 2.2 and 5.0 kb in a variety of hematopoietic cell lines, including the B lymphoblastoid line CESS, the T cell leukemias HUT-102 and HPB-ALL, lymphokine activated T cells, tonsillar B cells and the histiocytic lymphoma U937.

Immunoprecipitation of CD44 from transfected COS cells reveals that the mesenchymal or hematopoietic form of CD44 is about 80–90 kd. Hematopoietic CD44 transfected into a B cell line has been observed to result in the binding of the CD44-bearing lymphocytes to rat lymph node stromal cells in primary culture, indicating that hematopoietic CD44 may play a role in lymphocyte homing. It has been shown that hematopoietic CD44 is an extracellular matrix receptor with affinity for collagens type I and VI (Stamenkovic et al., Cell 56:1057–1062 (1989)). Hematopoietic CD44 may also have a lymphocyte activation role.

The ability to interfere with the binding of hematopoietic CD44 to lymph node cells, or the ability to cause such binding to occur on other surfaces, can be useful in diagnostics and therapy. For example, modification of this binding can serve to regulate the homing potential of lymphocytes. Soluble forms of CD44 can have immunomodulatory activity.

To isolate a cDNA clone encoding the epithelial form of CD44, a cDNA library prepared from the colon carcinoma line HT29 was transfected into COS cells by the DEAE-Dextran method described supra. The cells were pooled 48 hours after transfection, incubated with anti-CD44 monoclonal antibody F-10-44-2 (Dalchau et al., Eur. J. Immunol. 10:745–749 (1980)) and panned on dishes coated with goat-anti-mouse affinity purified antibody. After several washes, the adherent cells were lysed, and episomal DNA purified and transformed into E. coli. After two similar rounds of enrichment following spheroplast fusion, as described supra, plasmid DNA recovered from seven out of ten randomly picked colonies was found to direct the appearance of epithelial CD44 determinants on transfected COS cells. All seven of the positive clones bore cDNA inserts of about 2.4 kb.

Restriction enzyme analysis of the clone containing the epithelial cDNA insert showed that the coding sequence (Table 8) was enlarged relative to the hematopoietic CD44 insert by the addition of 496 base pair. DNA sequence analysis showed that the epithelial CD44 cDNA is quite similar to the CD44.5 cDNA, but encoded an additional extracellular domain of 165 amino acids, inserted about 140 residues upstream of the transmembrane section shared by both clones. The mature protein would comprise 493 residues.

RNA blot analysis has revealed that the epithelial CD44 transcripts comprise 2.2, 2.7 and 5.5 kb species. Epithelial CD44 isolated by immunoprecipitation has revealed that the glycoprotein is about 160 kd.

TABLE 8

```
   1  CCAGCCTCTG CCAGGTTCGG TCCGCCATCC TCGTCCCGTC CCCTGCCCCG CGCCCAGGGA TCCTCCAGCT

81  CCTTTCGCCC GCGCCCTCCG TTCGCTCCCG ACACCATGGA TTCCGTCCCG CAAGTTTTGG TGGCACGGCAG CCTGGGGACT CTGCCTCGTG
       P  L  S    A  P        F           M  D       F  R       K  F  W    W  H  A  A    W  G  L       C  L  V

161  CCGCTGAGCC TGGCGCAGAT CGATTTGAAT ATAACCTGCC GCTTTGCAGG TGTATTCCAC CCTTGCCCAC GCTTTGCAGG ATGGTCGCTA
       R  D       A  Q  I    D  L  N    I  T  C    R  F  A  G    V  F  H    L  P  T       F  A  G       M  E  K  A

241  CAGCATCTCT CGGACGGAGG CCGCTGACCT CTGCAAGGCT TTCAATAGCA CCTTGCCCAC CAAGTTTTGG AATGGCCCAG ATGGAGAAAG
       S  I  S    R  T  E  A    P  A  D  L    C  K  A       F  N  S       L  P  T       --CHO--       M  E  K

321  CTCTGAGCAT CGGATTTGAG ACCTGCCAGGT ATGGGTTCAT AGAAGGGCAT GTGGTGATTC CCCGGATCCA CCCCAAACTCC
       L   S       G  F  E    T  C  R  Y       F  I       E  G  H       V  V  I  P       R  I  H       P  N  S

401  ATCTGTGCAG CAAACAACAC AGGGGTGTAC GTACATCAGT CCAGTATGAC ACATATTGCT TCAATGCTTC
       I  C  A  A    N  N  T       G  V  Y       T  S       Q  Y  D       T  Y  C       N  A  S

481  AGCTCCACCT GAAGAAGATT GTACATCAGT GTACATCAGT TTGATGGACC AATTACCATA ACTATTGTTA
       A  P         E  E  D  C       T  S           --CHO--       D  G  P       I  T  I       V  N

561  ACCGTGATGG CACCGCGCTAT GTAATTCTCA GTCCAGAATACAG AACGAATCCT GAAGACATCT ACCCCAGCAA CCCTACTGAT
       T                    T  R  Y        N  S  Q       E  Y  R       T  N  P       E  D  I  Y       P  S  N       P  T  D

641  GATGACAGTGA GCAGCGGCTC CTCCAGTGAA AGGAGCAGCA CTTCAGGAGG TTACACCTTT TACACCTTTT CTACTGTACA
       D  D  V  S    Q  S        S  G            R  S  S  T    S  G  G         Y  I  F            T  V  H

721  CCCCATCCCA GACGAAGACA GTCCCCTGGAT CACCGACAGC ACAGACAGAA TCCCCTCGTAC CAATATGGAC TCCAGTCATA
       P  I  P        D  E  D      P  W  I       T  D  S        T  D  R           P  R  T       N  M  D       S  S  H  S

801  GTACAACGCT TCAGCCTACT GCAAAATCCAA GAGCTTTCTCT ACACAGGTTT GGTGGACAGGA TTGGACAGGA CAGGACCTCT TTCAATGACA
       T  L       Q  P  T       A  N  P  N       S  F        T  G  L       V  E  D       L  D  R  T       G  P  L       S  M  T

881  ACGCAGCAGA GTAATTCTCA ACATCACATG ACATCACATG AGGCTTTGGA AGAAGATAAA GACCATCCAA CAACTTCTAC
       T  Q  Q  S    N  S  Q       T  S  H  E                    G  L  E       D  K           D  H  P       T  S  T

961  TCTGACATCA AGCAATAGGA ATGATGTCAC AGAGACCCAA AGAGACCCAA AGGACCAGAA ATCATTCTGA AGGCTCAACT CATTTACTGTT
       L           S  N  R       D  V  T                     R  D  P  N       R  D           H  S  E           H  L  L  E

1041 AAGGTTATAC CTCTCATTAC CCACACACGA CCACACACGA GACCTTCATC CCAGTGACCT AGGCTAAGAC TGGGTCCTTTT
       K  V  Y        S  H  Y       P  H  T                        T  F  I       P  V  T  S       A  K  T       G  S  F

1121 GGAGTTACTG CAGTTACTGT TGGAGATTCC TCAATGATTCC TCAATGGACCTCT CTTATCAGGA GACCAAGACA CATTCCACCC
       G  V  T  A    V  T  V                       D  S           N  R  S           L  S             D  Q  D  T       F  H  P

1201 CAGTGGGGG TCCCATACCA CTCATGATC ATGGGAGTCA GGACACTCAC AGAAGGTGGA GCAAACACAT
       S  G  G    S  H  T  T       H  G          G  S  Q       G  H  S  H       E  G  G            A  N  T
```

TABLE 8-continued

| | | | | | | | | | |
|---|---|---|---|---|---|---|---|---|---|
| 1281 | CCTCTGGTCC<br>S  G  P | TATAAGGACA<br>I  R  T | CCCCAAATTC<br>P  Q  I  P | CAGAATGGCT<br>E  W  L | GATCATCTTG<br>I  I  L | GCATCCCTCT<br>A  S  L  L | TGGCCTTGGC<br>A  L  A | TTTGATTCTT<br>L  I  L |
| | | | | | --CHO-- | | | |
| 1361 | GCAGTTTGCA<br>A  V  C  I | TTGCAGTCAA<br>A  V  N | CAGTCGAAGA<br>S  R  R | AGGTGTGGGC<br>R  C  G  Q | AGAAGAAAAA<br>K  K  K | GCTAGTGATC<br>L  V  I | AACAGTGGCA<br>N  S  G  N | ATGGAGCTGT<br>G  A  V |
| 1441 | GGAGGACAGA<br>E  D  R | AAGCCAAGTG<br>K  P  S  G | GACTCAACGG<br>D  L  N | AGAGGCCAGC<br>E  A  S | AAGTCTCAGG<br>K  S  Q  E | AAATGGTGCA<br>M  V  H | TTTGGTGAAC<br>L  V  N | AAGGAGTCGT<br>K  E  S  S |
| 1521 | CAGAAACTCC<br>Q  E  T  P | AGACCAGTTT<br>D  Q  F | ATGAGACAGC<br>M  T  A  D | GAACCTGCAG<br>N  L  Q | ATGTGGACA<br>N  V  D  M | AATGTGGACA<br>N  V  D  M | TGAAGATTGG<br>K  I  G | GGTGTAACAC<br>V  * |
| 1601 | CTACACCATT | ATCTTGGAAA | GAAACAACGT | TGGAAACATA | ACCATTACAG | GGGAGCTGGG | ACACTTAACA | GATGCAATGT |
| 1681 | GCTACTGATT | GTTTCATTTC | GAATCTATAA | TAGCATAAAA | TTTTCTACTC | TTTTTGTTTT | TTGTGTTTTG | TTCTTTAAAG |
| 1761 | TCAGGTCCAA | TTTGTAAAAA | CAGCATTGCT | TTCTGAAATT | AGGGCCCAAT | TAATAATCAG | CAAGAATTTT | GATCGTTTCA |
| 1841 | GTTCCCCACT | TGGAGGCCTT | TCATCCCCTCG | GGTGTGCTAT | TTCCTGAAATT | TAACAAAAAC | CTACCACATA | GTTATTCCTG |
| 1921 | ATCGCCAACC | TTGCCCCCCA | CCAGCTAAGG | ACATTTCCAG | GGCATTGCTT | GCCTGGTCCT | GGGAGGAAAT | TTGAATGGGT |
| 2001 | CATTTTGCCC | TTCCATTAGC | CTAATCCCTG | GGCATTGCTT | TCCACTGAGG | TTGGGGGTTG | GGGTGTACTA | GTTACACATC |
| 2081 | TTCAACAGAC | CCCCTCTAGA | AATTTTTCAG | ATGCTTCTGG | TGGATCAGTC | GAGACACCCA | AAGGGTAAGT | CTATTTATCT | GTAGTAAACT |
| 2161 | ATTTATCTGT | GTTTTTGAAA | TATTAAAACCC | CTTTTATTCA | TGGATCAGTC | CTTTTATTCA | GTATAATTTT | TTAAAGTTAC | TTTGTCAGAG |
| 2241 | GCACAAAAAG | GGTTTAAACT | GATTCATAAT | AAATATCTGT | ACCTTCTTCG | AAAAAAAAA | AAAAAAAA | | |

Transfected B cells expressing epithelial CD44 do not adhere to rat lymph node stromal cells in primary culture as do hematopoietic CD44 transfected lymphocytes. The epithelial CD44 is weakly expressed by normal epithelium but highly expressed by carcinomas. It is possible that an extracellular matrix receptor function of epithelial CD44 may promote tumor invasiveness.

The ability to interfere with the binding of epithelial CD44 with extracellular matrices can be useful in therapy or diagnostics. For example, interference of the epithelial CD44 binding to extracellular matrices can diminish the likelihood of metastasis in cancer patients. Soluble forms of CD44 can act to prevent metastatic cells from "homing" to lymph nodes.

EXAMPLE XVI

The Isolation and Molecular Cloning of cDNA Encoding CD53 Antigens

CD53, the antigen recognized by antibodies MEM-53 (Hadam, M. R. (1989) in *Leucocyte Typing IV,* Knapp, B. et al. (eds.) Oxford Univ. Press, p. 674), HD77, HI29 and HI36, and 63-5A3, is a glycoprotein widely distributed among, but strictly restricted to, nucleated cells of the hematopoietic lineages (Stevanova, I., et al., (1989) in *Leucocyte Typing IV,* Knapp, B. et al. (eds.) Oxford Univ. Press, p. 678). CD53 is expressed by monocytes and macrophages, by granulogytes, dendritic cells, osteoclasts and osteoblasts, and by T and B cells from every stage of differentiation.

To obtain a cDNA clone encoding CD53, cDNA libraries constructed from peripheral blood lymphocytes and the promyelocytic tumor cell line HL60 were transfected into COS cells by the DEAE-Dextran method, described supra. The cells were pooled 48 hours after transfection, incubated with monoclonal antibodies MEM-53, and panned as described in Seed and Aruffo, *Proc. Natl. Acad. Sci. USA* 84:3365–3369 (1987) and Aruffo and Seed, *Proc. Natl. Acad. Sci. USA* 84:8573–8577 (1987). After two subsequent rounds of enrichment following spheroplast fusion, plasmid DNA recovered from single colony isolates was transfected into COS cells, and scored for CD53 expression by immunofluorescence.

Two of eight transfectants were positive, each bearing an insert of about 1.5 kb. COS cells transfected with either clone reacted with each of the antibodies MEM-53, HI29, HI36 and 63-5A3.

To isolate CD53 from peripheral blood lymphocytes and transfected COS cells for purposes of comparison, the lymphocytes and transfected COS cells were surface labeled with $^{125}$I using lactoperoxidase and $H_2O_2$, and then lysed in a lysis buffer of 50 mM Tris-HCl pH 8.0 containing 1% NP40, 150 mM NaCl, 5 mM $MgCl_2$, 5 mM KCl, 20 mM iodoacetamide and 1 mM phenylmethylsulfonyl-fluoride. Cells were solubilized at a concentration of $2.5 \times 10^7$ cells/ml in lysis buffer for 45 minutes then centrifuged at 12,000 g. After preclearing with goat anti-mouse immunoglobulin beads (Cappel, Malvern, Pa.), immunoprecipitations were performed with monoclonal antibodies MEM53 or 63-5A3 and protein A-Sepharose CL-4B (Sigma, St. Louis, Mo.) as described by Schneider et al. (*J. Biol. Chem.* 257:10766 (1982)). Immunoprecipitates were eluted in SDS-sample buffer and analyzed on 12.5% acrylamide gels containing sodium dodecyl sulfate.

A broad band of radioiodinated protein ranging in mass from 34 kd to 42 kd was obtained from peripheral blood lymphocytes either with MEM-53 or 63-5A3 monoclonal antibodies, comparable to the band obtained from CD53-transfected COS cells, which extended from 36 kd to 46 kd. The higher molecular mass in COS cells is atypical, as cell surface proteins recovered from transfected COS cells usually display unchanged or lower molecular mass than those found on the cell from which the cDNA clone originated (Aruffo and Seed, *Proc. Natl. Acad. Sci. USA* 84:3365–3369 (1987)). Approximately 15 kd of mass are liberated from the glycoprotein by digestion with endoglycosidase F (N-glycanase), whereas treatment with neuraminidase and O-glycanase has no effect on the apparent molecular mass (Hadam, M. R. (1989) in *Leucocyte Typing IV,* Knapp, B. et al. (eds.) Oxford Univ. Press, p. 674; Stevanova et al., in *Leucocyte Typing IV,* Knapp, B. et al. (eds.) Oxford Univ. Press, p. 678). An additional faint band of 20 kd, possibly unglycosylated precursor, was detected in immunoprecipitates of transfected COS cells, but was absent from immunoprecipitates of peripheral blood lymphocytes.

Blot hybridization of genomic DNA from the T cell line PEER digested with several enzymes revealed a pattern consistent with a single copy gene. RNA blot analysis revealed a single 1.8 kb mRNA derived from B, T, and myeloid cell lines and from peripheral blood lymphocytes. The level of expression was comparable in the different cell lines except in THP1 cell line, which had little CD53 mRNA. CD53 transcripts are more abundant in peripheral blood lymphocytes than in cultivated cell lines, consistent with the higher surface expression of CD53 among these cells.

The nucleotide sequence of CD53 cDNA was determined by dideoxynucleotide chain termination as described, supra, using synthetic oligonucleotide primers. The sequence of the CD53 insert consists of 1452 nucleotides (Table 9), and terminates close to two overlapping AATAAA motifs (singly underlined). The 3' noncoding sequence contains three examples of the ATTTA sequence (indicated by quotation marks), which has been shown to mediate mRNA instability (Shaw and Kamen, *Cell* 46:659 (1986)).

TABLE 9

```
  1  CTCAAGGATA ATCACTAAAT TCTGCCGAAA GGACTGAGGA ACGGTGCCTG GAAAAGGGCA AGAATATCAC GGCATGGGCA
                                                                                   M  G  M

81  TGAGTAGCTT GAAACTGCTG AAGTATGTCC TGTTTTTCTT CAACTTGCTC TTTTGGATCT GTGGCTGCTG CATTTTGGGC
      S    L   K  L   L   K  Y   V  L   F  F   F    N  L   L    F  W   I  C    G  C   C    I  L   G

161  TTTGGGATCT ACCTGCTGAT CCACAACAAC TTCGGAGTGC TCTTCCATAA CCTCCCCTCC CTCACGCTGG GCAATGTGTT
      F  G   I  Y    L  L   I    H  N   N    F  G   V  L    F  H   N    L  P   S    L  T   L  G    N  V   F

241  TGTCATCGTG GGCTCTATTA TCATGGTAGT TGCCTTCCTG GGCTGCATGG GGTGACCTTG GCTCTATCAA GGAAAACAAG TGTCTGCTTA
      V  I   V   G  S   I  I   M  V   V    A  F   L    G  C   M  G       V  T   L    A  I   K    E  N   K    C  L   L   M

321  TGTCGTTCTT CATCCTGCTG CTGATTATCC TCCTTGCTGA GGTGACCTTG GCCATCCTGC TCTTTGTATA TGAACAGAAG
      S  F   F   I  L   L    L  I   I  L    L  A   E         V  T  L    A  I   L   L   F  V   Y    E    Q  K

401  CTGAATGAGT ATGTGGCTAA GGGTCTGACC ACCGTTACCA CTCAGACAAT AGCACCAAGG CAGCGGTGGA
      L  N   E  Y    V  A   K    G  L   T    R  Y   H    S  D   N    S  T  K    A  W   D

481  CTCCATCCAG TCATTTCTGC AGTGTTGTGG ACGAGTGATT GGACCAGTGG CCCACCAGCA TCTTGCCCCT
      S  I   Q   S  F   L   Q    C  C   G    T  S   D   W    T  S   G    P  P   A    S  C  P   S

561  CAGATCGAAA AGTGGAGGGT TGCTATGCGA AAGCAAGACT TATAAATGGC TGTATATCGG AATCATCACC
      D  R   K   V  E   G    C  Y   A   K    A  R   L    I  N   G    C  Y   I  G    I  I   T

641  ATCTGTGTAT GTGTGATTGA GGTGTTGGGG ATGTCCTTTG CACTGACCCT GAACTGCCAG ATTGACAAAA CCAGCCAGAC
      I  C   V    V  I   E    V  L   G    M  S   F   A    L  T  L    N  C   Q   I  D   K  T    S  Q   T

721  CATAGGGCTA TGATCTGCCAG TAGTTCTGTG GTGAAGAGAC TTGTTTCATC TCCGGAAATG CAAAAACCATT TATAGCATGA
      I  G   L   *
```

TABLE 9-continued

| | | | | | | | | |
|---|---|---|---|---|---|---|---|---|
| 801 | AGCCCTACAT | GATCACTGCA | GGATGATCCT | CCTCCCATCC | TTTCCCTTTT | TAGGTCCCTG | TCTTATACAA | CCAGAGAAGT |
| 881 | GGGTGTTGGC | CAGGCACATC | CCATCTCAGG | CAGCAAGACA | ATCTTTCACT | CACTGACGGC | AGCAGCCATG | TCTCTCAAAG |
| 961 | TGGTGAAACT | AATATCTGAG | CATCTTTTAG | ACAAGAGAGG | CAAAGACAAA | CTGGATTTAA | TGGCCCAACA | TCAAAGGGTG |
| 1041 | AACCCAGGAT | ATGAATTTTT | GCATCTTCCC | ATTGTCGAAT | TAGTCTCCAG | CCTCTAAATA | ATGCCCAGTC | TTCTCCCCAA |
| 1121 | AGTCAAGCAA | GAGACTAGTT | CTGGGGCCAG | GCTCACTGGA | AACCCTCTGT | TTCTCTTTGA |
| 1201 | CTAAGTGCCC | TGGCTACAGG | AATTACACAG | TTCTCTTTCT | CCAAAGGGCA | AGATCTCATT | TCAATTTCTT | TATTAGAGGG |
| 1281 | CCTTATTGAT | GTGTTCTAAG | TCTTTCCAGA | AAAAAACTAT | CCAGTGATTT | ATATCCTGAT | TTCAACCAGT | CACTTAGCTG |
| 1361 | ATAATCACAG | TAAGAAGACT | TCTGGTATTA | TCTCTCTATC | AGATAAGATT | TTGTTAAATGT | ACTATTTTAC | TCTTCAATAA |
| 1441 | ATAAAACAGT | TT | 1452 |

An open reading frame beginning at residue 74 encodes a protein of 219 amino acids with a predicted molecular weight of 24,340 kd. The predicted polypeptide is unusual in that it bears four major hydrophobic segments (doubly underlined), three of which fall in close proximity near the amino terminus of the molecule. The first hydrophobic segment is atypically long for either a signal sequence or a simple transmembrane alpha helix, and contains three cysteine residues and a glycine located in the middle. Both cysteine and glycine have been found to immediately precede the signal cleavage site (von Heijne, *Nucleic Acids Res.* 14:4683 (1986)), suggesting that the amino terminus of the mature protein begins in the middle of the first hydrophobic domain. Some support for this view is afforded by the finding that the size of the polypeptide backbone of ME491, a related type III integral membrane protein, discussed infra, is smaller than the size predicted from the cDNA sequence, possibly as a consequence of signal peptide excision. Because there are only two potential sites for N-linked glycan addition (indicated in Table 9 by —CHO— designations), located between the third and fourth hydrophobic segments, the carboxyl terminus must lie inside the cell, as well as the short hydrophilic portion between the second and third hydrophobic segments. If the amino terminus is not processed, it must likewise remain intracellular.

CD53 is a Type III integral membrane protein related to three other membrane proteins: ME491 antigen, a melanoma protein whose increased expression correlates well with tumor progression (Hotta et al., *Cancer Res.* 48:2955 (1988)); CD37, an extensively glycosylated antigen predominantly expressed on B cells, but not B cell lineage specific (Schwartz et al., *J. Immun.* 140:905 (1988); and S5.7, an unglycosylated antigen broadly expressed on cells of hematopoietic lineage (Pressano et al., *Cancer Res.* 43:4812 (1983)). In addition, CD53 is distantly related to *E. coli* lac Y permease, a type III integral membrane protein which ferries lactose into the bacterial cell. CD53 transcripts in peripheral blood lymphocytes increase in prevalence following mitogenic stimulation by PHA, suggesting that the protein may be involved in the transport of factors essential for cell proliferation.

Among the molecules with broad reactivity in the hemopoietic system, CD53 presently holds the widest reactivity as well as the strictest restriction to hematopoietic cells. Anti-CD53 antibodies are a useful tool for the identification of hematopoietic neoplasms, and may prove helpful for identifying morphologically poorly defined cells, for example in spleen or bone marrow primary cultures.

Equivalents

Those skilled in the art will recognize or be able to ascertain, using no more than routine experimentation, many equivalents to the specific embodiments of the invention described herein. Such equivalents are intended to be encompassed within the scope of this invention.

We claim:

1. A cloned cDNA encoding a human CD40 cell surface antigen or a functional derivative of said cDNA encoding at least 6 amino acids of human CD40.

2. Substantially pure cDNA comprising the nucleotide sequence shown in FIG. 16 or a functional derivative of at least 18 nucleotides thereof, wherein said derivative encodes at least 6 amino acids of human CD40.

* * * * *

UNITED STATES PATENT AND TRADEMARK OFFICE
CERTIFICATE OF CORRECTION

Page 1 of 2

PATENT NO. : 5,849,898

DATED : December 15, 1998

INVENTOR(S) : Seed et al.

It is certified that error appears in the above-identified patent and that said Letters Patent is hereby corrected as shown below:

Title page, Item [75], please delete "Janet Allen, Glasgow, Scotland;" and "David Camerini, Charlottesville, Va.; Leander Lauffer; Carmen Oquendo, both of Gladenbach, Germany; David Simmons, Headington, United Kingdom; Siegfried Stengelin, Eppstein, Germany; Martine Amiot, Nantes, France"

On the front page, second column, under "Other Publications", under "Hynes, R.O.", please delete "(2987) and replace with --(1987)--.

On page 2, first column, under "Other Publications", under "McMichael et al.", please delete "*Antigen,*" and replace with --*Antigens,*--.

On page 2, first column, under "Other Publications", under "Simmmons et al.", please delete "Simmmons" and replace with --Simmons--.

On page 2, first column, under "Other Publications", under "Bernstein et al.", please delete "*immunol.*" and replace with --*Immunol.*--.

On page 2, first column, under "Other Publications", under "Johnson et al.", please insert --47:-- right before "545-554" with no space between.

On page 2, second column, under "Other Publications", under "Weiss, A. et al.", please delete "*immunol.*" and replace with --*Immunol.*--.

In column 3, line 32, please delete "CD2LFA-3" and replace with --CD2/LFA-3--.

In column 7, line 58, please delete "(" before "HindIII);".

In column 10, line 48, please delete "Solution" and replace with --solution--.

In column 11, line 40, please delete "1 ul" and replace with --1 $\mu$l--.

In column 15, line 27, please delete "1000)/500%" and replace with --1000)/50%--.

In column 17, line 7, please delete "EDTA0.02%" and replace with --EDTA/0.02%--.

In column 19, line 17, please delete "y" between "oligonucleotides," and "giving".

In column 20, line 35, please delete "of" between "that" and "antigen".

In column 22, line 47, please delete "2 l" and replace with --2 L--.

In column 22, line 64, please insert a comma after "Thereafter".

In column 23, line 19, please delete "24 6 cm" and replace with --24 - 6 cm--.

In column 27, line 46, please delete "CD6, CD6," and replace with --CD6, CD7,--.

UNITED STATES PATENT AND TRADEMARK OFFICE
CERTIFICATE OF CORRECTION

PATENT NO.   : 5,849,898

DATED        : December 15, 1998

INVENTOR(S)  : Seed et al.

It is certified that error appears in the above-identified patent and that said Letters Patent is hereby corrected as shown below:

In column 31, line 18, please delete "MC1061p3" and replace with --MC1061/p3--.
In column 33, line 60, please delete "CD7+T cells" and replace with --CD7$^+$ T cells.
In column 33, line 62, please insert a --(-- before "1982)),".
In column 35, line 5, please delete "PBS/0.5" and replace with --PBS/0.5%--.
In column 35, line 12, please delete "PBS/0.50" and replace with --PBS/0.5%--.
In column 35, line 40, please delete "describe" and replace with --described--.
In column 36, line 67, please delete "(985)" and replace with --(1985)--.
In column 37, line 22, please insert --a-- in between "with" and "molecular".
In column 42, line 59, please delete "30)."
In column 44, line 14, please delete "8:298-3-3" and replace with --8:298-303--.
In column 46, line 46, please delete "glycosylaton" and replace with --glycosylation--.
In column 53, line 16, please delete "*Plasmodum*" and replace with --*Plasmodium*--.
In column 83, line 31, please delete "granulogytes," and replace with --granulocytes,--.

Signed and Sealed this

Eleventh Day of April, 2000

Attest:

Attesting Officer

Q. TODD DICKINSON

Director of Patents and Trademarks